(12) United States Patent
Heffernan et al.

(10) Patent No.: US 9,409,893 B2
(45) Date of Patent: Aug. 9, 2016

(54) HETEROARYL DERIVATIVES AND USES THEREOF

(71) Applicant: Jacobus Pharmaceutical Company, Inc., Princeton, NJ (US)

(72) Inventors: Gavin David Heffernan, Florence, NJ (US); David Penman Jacobus, Princeton, NJ (US); Kurt William Saionz, Cranford, NJ (US); Guy Alan Schiehser, Washington Crossing, PA (US); Hong-Ming Shieh, Newtown, PA (US); Wenyi Zhao, Monroe Township, NJ (US)

(73) Assignee: Jacobus Pharmaceutical Company, Inc., Princeton, NJ (US)

( * ) Notice: Subject to any disclaimer, the term of this patent is extended or adjusted under 35 U.S.C. 154(b) by 129 days.

(21) Appl. No.: 14/074,819

(22) Filed: Nov. 8, 2013

(65) Prior Publication Data

US 2014/0135320 A1    May 15, 2014

Related U.S. Application Data

(60) Provisional application No. 61/724,337, filed on Nov. 9, 2012.

(51) Int. Cl.

| | | |
|---|---|---|
| A61K 31/535 | (2006.01) |
| A61K 38/00 | (2006.01) |
| A61P 33/00 | (2006.01) |
| A01N 37/18 | (2006.01) |
| C07D 413/04 | (2006.01) |
| A61K 31/343 | (2006.01) |
| A61K 31/381 | (2006.01) |
| A61K 31/415 | (2006.01) |
| A61K 31/4418 | (2006.01) |
| A61K 31/4439 | (2006.01) |
| A61K 31/47 | (2006.01) |
| A61K 31/496 | (2006.01) |
| A61K 31/505 | (2006.01) |
| A61K 31/536 | (2006.01) |
| A61K 31/5377 | (2006.01) |
| A61K 45/06 | (2006.01) |
| C07D 213/38 | (2006.01) |
| C07D 213/64 | (2006.01) |
| C07D 213/73 | (2006.01) |
| C07D 215/14 | (2006.01) |
| C07D 231/12 | (2006.01) |
| C07D 239/26 | (2006.01) |
| C07D 307/81 | (2006.01) |
| C07D 333/28 | (2006.01) |
| C07D 333/58 | (2006.01) |
| C07D 213/84 | (2006.01) |
| C07D 217/16 | (2006.01) |
| C07D 401/10 | (2006.01) |
| C07D 241/12 | (2006.01) |
| C07D 213/36 | (2006.01) |
| C07D 213/61 | (2006.01) |
| C07D 213/65 | (2006.01) |
| C07D 307/80 | (2006.01) |

(52) U.S. Cl.
CPC ............ *C07D 413/04* (2013.01); *A61K 31/343* (2013.01); *A61K 31/381* (2013.01); *A61K 31/415* (2013.01); *A61K 31/4418* (2013.01); *A61K 31/4439* (2013.01); *A61K 31/47* (2013.01); *A61K 31/496* (2013.01); *A61K 31/505* (2013.01); *A61K 31/536* (2013.01); *A61K 31/5377* (2013.01); *A61K 45/06* (2013.01); *C07D 213/36* (2013.01); *C07D 213/38* (2013.01); *C07D 213/61* (2013.01); *C07D 213/64* (2013.01); *C07D 213/65* (2013.01); *C07D 213/73* (2013.01); *C07D 213/84* (2013.01); *C07D 215/14* (2013.01); *C07D 217/16* (2013.01); *C07D 231/12* (2013.01); *C07D 239/26* (2013.01); *C07D 241/12* (2013.01); *C07D 307/80* (2013.01); *C07D 307/81* (2013.01); *C07D 333/28* (2013.01); *C07D 333/58* (2013.01); *C07D 401/10* (2013.01)

(58) Field of Classification Search
None
See application file for complete search history.

(56) References Cited

U.S. PATENT DOCUMENTS

| | | | |
|---|---|---|---|
| 3,723,449 A | 3/1973 | Wirth | |
| 5,292,890 A | 3/1994 | Moshchitsky et al. | |
| 7,589,127 B2 | 9/2009 | Dorn | |
| 8,367,078 B2 | 2/2013 | Sayeski et al. | |
| 8,962,657 B2 * | 2/2015 | Heffernan et al. | ............ 514/317 |
| 2007/0072833 A1 | 3/2007 | Wendt | |

(Continued)

FOREIGN PATENT DOCUMENTS

| | | | |
|---|---|---|---|
| WO | WO 2004/000783 A1 | 12/2003 | |
| WO | WO 2004/072051 A1 | 8/2004 | |

(Continued)

OTHER PUBLICATIONS

Brown and Rampe, "Drug-Induced Long QT Syndrome: Is HERG the Root of all Evil", Pharmaceutical News, 2000, 7(4), 15-20.

(Continued)

*Primary Examiner* — Kortney L Klinkel
*Assistant Examiner* — Tori M Strong
(74) *Attorney, Agent, or Firm* — Baker & Hostetler LLP

(57) ABSTRACT

The present invention relates to antimalarial compounds and their use against protozoa of the genus *Plasmodium*, including drug-resistant Plasmodia strains. This invention further relates to compositions containing such compounds and a process for making the compounds.

22 Claims, No Drawings

(56) References Cited

U.S. PATENT DOCUMENTS

2014/0135360 A1    5/2014    Heffernan
2015/0080324 A1*   3/2015    Heffernan et al. .............. 514/24

FOREIGN PATENT DOCUMENTS

WO    WO 2006/094187 A2    9/2006
WO    WO 2014/074775       5/2014
WO    WO 2014/074778       5/2014

OTHER PUBLICATIONS

Burckhalter et al, "Aminoalkylphenols as Antimalarials. I. Simply substituted α Aminocresols", J. Am. Chem. Soc., 1946, 68, 1894-1901.
Burckhalter et al, "Aminoalkylphenols as Antimalarials. II. (Heterocyclic-amino)-α-amino-o-cresols. The Synthesis of Camoquin" J. Am. Chem. Soc., 1948, 70, 1363-1373.
Chen et al, "A Highly Highly Selective Pyrophosphate Sensor Based on ESIPT Turn-On in Water", Organic Letters, Mar. 18, 2011, 13(6), 1362-1365.
Childs, G. et al., Am. H. Trop. Med. Hyg. 1988, vol. 38, pp. 19-23.
Curran et al, "A Molecular Basis for Cardiac Arrhythmia: HERG Mutations Cause Long QT Syndrome", Cell, Mar. 10, 1995, 80(5), 795-803.
Duncan,W.G. and Henry, D.W., "2-(.omega.-Aminoalkyl)-4-tert-butyl-6-phenylphenols as antimalarial agents", J. Med. Chem., Jul. 1969, 12(4), 711-712.
Hung et al, "Camoform Analogs As Potential Agents Against Mefloquine Resistant Malaria", Eur. J. Med. Chem., Chimie Therapeutique, Editions Dimeo, Arcueil, FR, Jan. 1, 1983, 18(1), 61-66.
International Patent Application No. PCT/US2013/069056: International Search Report dated Mar. 21, 2014, 6 pages.
Ishiyama et al, "Palladium (0)-Catalyzed Cross-Coupling Reaction of Alkoxydiboronwith Haloarenes: A Direct Procedure for Arylboronic Esters", J. Org. Chem., 1985, 60, 7508-7510.
Ishiyama et al, "Synthesis of Arylboronates via the Palladium(0)-Catalyzed Cross-Coupling reaction of Tetra(alkoxo)diborons with Aryl Triflates", Tetrahedron Letters, 1997, 38(19), 3447-3450.
Karle, J.M., and Karle, I.L., "Crystal and Molecular Structure of the Antimalarial Agent 4-(tert-Butyl)-2-(tert-Butylaminomethyl)-6-(4-Chlorophenyl)Phenol Dihydrogen Phosphate (WR 194,965 Phosphate)", Antimicrobial Agents and Chemotherapy, Apr. 1988, 32(4), 540-546.
Peters, W. and Robinson, B.L., "The Chemotherapy of Rodent Malaria, XXXVII, The in vivo action of two mannich bases, WR 194,965 and WR 228,258 and an 8-aminoquinoline WR 225,448", Annals of Tropical Medicine and Parasitology, 1984, 78(6), 561-565.
Peters, W. and Robinson, B.L., "The Chemotherapy of Rodent Malaria, XXXVIII, Studies on the activity of three new antimalarials (WR 194,965, WR 228,258 and WR 225,448) against rodent and human malaria parasites (*Plasmodium berghei* and *P. falciparum*)", Annals of Tropical Medicine and Parasitology, 1984, 78(6), 567-579.
Powles, M.A., et al., "MK-4815, a Potential New Oral Agent for Treatment of Malaria" Antimicrobial Agents and Chemotherapy, Feb. 2012, 56(5), 2414-2419.
Sanguinetta et al, "A Mechanistic Link Between an Inherited and an Acquired Cardiac Arrhythmia: HERG Encodes the IKr Potassium Channel", Cell, Apr. 21, 1995, 81(2):299-307.
Schmidt, L.H., and Crosby, R. "Antimalarial Activities of WR-194,965, an a-Amino-o-Cresol Derivative", Antimicrobial Agents and Chemotherapy, Nov. 1978, 14(5), 672-679.
Silverman, R. "The Organic Chemistry of Drug Design and Drug Action," 2004, Elsevier, pp. 29-32.
Weirich, J. and Antoni, H., "Rate-Dependence of Antiarrhythmic and Proarrhythmic Properties of Class I and class III Antiarrhythmic Drugs", Basic res. Cardiol, 1998, 93 Suppl 1, 125-132.
Werbel et al, "Synthesis Antimalarial Activity and Quantitative Structure-Activity-Relationship of Tebuquine and a Series of Related 5-[(7-Chloro-4-quinolinyl)amino]-3-[(alkyl ami no)methyl][1,1' Biphenyl]-2-o1 s and N-Oxidesu", Journal of Medicinal Chemistry, American Chemical Society, Jan. 1, 1986, 29(6), 924-939.
Yao et al, "Predicting QT prolongation in humans during early drug development using hERG inhibition and an anaesthetized guinea-pig model", British Journal of Pharmacology 2008, 154, 1446-1456.
Yap and Camm, "Arrhythmogenic Mechanisms of Non-Sedating Antihistamines", Clin. Exp. Allergy, Jul. 1999, 29 Suppl 3,174-81.
Meanwell, "Synopsis of Some Recent Tactical Application of Bioisosteres in Drug Design", J. Med. Chem., Apr. 2011, 54(8), 2529-2591.
Gilchrist, "Aromatic Heterocycles", Heterocyclic Chemistry, Edinburgh, Longmans, 1992, $3^{rd}$ Edition, Chapter 2, 8-23.
Carey, "Alcohols and Alkyl Halides", Organic Chemistry, NY McGraw Hill, 2000, $4^{th}$ Edition, 129-131.

* cited by examiner

HETEROARYL DERIVATIVES AND USES THEREOF

CROSS REFERENCE TO RELATED APPLICATION

This application claims the benefit of U.S. Provisional Application No. 61/724,337, filed Nov. 9, 2012, the entirety of which is incorporated by reference herein.

TECHNICAL FIELD

The present invention relates to antimalarial compounds and their use against protozoa of the genus *Plasmodium*, including drug-resistant Plasmodia strains. This invention further relates to compositions containing such compounds and processes for making the compounds.

BACKGROUND

Malaria is an infectious febrile disease caused by the protozoa of the genus *Plasmodium*, which are parasitic in the red blood cells, and are transmitted by the bites of infected mosquitoes of the genus *Anopheles*. The disease is characterized by attacks of chills, fever, and sweating, occurring at intervals which depend on the time required for development of a new generation parasites in the body. After recovery from acute attack, the disease has a tendency to become chronic, with occasional relapses. There are four human species *Plasmodium falciparum* (*P. falciparum*), *Plasmodium vivax* (*P. vivax*), *Plasmodium malariae* (*P. malariae*) and *Plasmodium ovale* (*P. ovale*).

Among the various forms of human malaria, malaria caused by *P. falciparum*, characterized by severe constitutional symptoms and sometimes causing death, is responsible for the majority of the mortality in humans. *P. falciparum* is dangerous not only because it digests the red blood cell's hemoglobin, but also because it changes the adhesive properties of the cell it inhabits, which causes the cell to stick to the walls of blood vessels. This becomes dangerous when the infected blood cells stick to blood vessels, obstructing blood flow. The disease is prevalent in tropical and subtropical areas of the world including the Amazon region of Brazil, East and Southern Africa and Southeast Asia. According to the World Health Organization World Malaria Report 2011 there were 216 million cases of malaria in 2010 and 81% of these were in the WHO African Region. There were an estimated 655,000 malaria related deaths in 2010 with 86% of the victims being children under 5 years of age.

Malaria has been treated with various drugs throughout recent history including combinations of drugs. However, the emergence of drug resistant strains of malaria has become a significant problem in the treatment of malaria. The WHO recommends artemisinins in combination with other classes of antimalarials (artemisinin-based combination therapies (ACTs)) as the first line treatment for malaria caused by *P. falciparum*. The emergence of *P. falciparum* resistant to artemisinins, confirmed on the Cambodia-Thailand border in 2009 and suspected in parts of Myanmar and Vietnam, highlights the critical need for new malaria drugs from novel chemical classes.

Since the original work of Burckhalter (Burckhalter, J. H., et al., J. Am. Chem. Soc. 1946, 68, 1894-1901 and J. Am. Chem. Soc. 1948, 70, 1363-1373), aminoalkyl phenols have been studied extensively as antimalarial agents (See Wiselogle, F. Y., Ed.; Survey of Antimalarial Drugs, 1941-1945, Vols. I and II, Edwards Bros., Ann Arbor, Mich., and Duncan, W. G., et al., J. Med. Chem. 1969, 12, 711-712). Optimization of the original α-(dialkylamino)-o-cresol template led to the identification of WR-194,965 (Schmidt, L. H., et al., Antimicrobial Agents and Chemotherapy 1978, 14, 672-679, Peters, W., et al., Annals of Tropical Medicine & Parasitology 1984, 78, 561-565, and 1984, 78, 567-579) which was profiled in human clinical trials (Karle, J. M., et al., Antimicrobial Agents and Chemotherapy 1988, 32, 540-546). Further modifications involved addition of the known antimalarial 4-aminoquinoline moiety to the aminoalkyl phenol template and led to the identification of antimalarial compounds such as Amodiaquine (Burckhalter, J. H., et al., J. Am. Chem. Soc. 1948, 70, 1363-1373) and Tebuquine (Werbel, L. M., et al., J. Med. Chem. 1986, 29, 924-939). Recently, 3,5-disubstituted-2-aminoalkylphenols with antimalarial activity have been reported (U.S. Pat. No. 7,589,127, issued Sep. 15, 2009 and Powles, M. A., et al., Antimicrobial Agents and Chemotherapy 2012, 56, 2414-2419).

New antimalarial compounds with exceptional potency, high activity against resistant strains, and good safety profiles are still needed.

SUMMARY

The present invention relates to compounds and compositions for the treatment of malaria, including drug resistant malaria. The compounds of this invention are antiprotozoal agents effective in vitro and in vivo against protozoa of the genus *Plasmodium* (*P. falciparum, P. bergei*, etc.), the infectious agent responsible for malaria.

The present invention is directed to compounds of Formula I and Formula II:

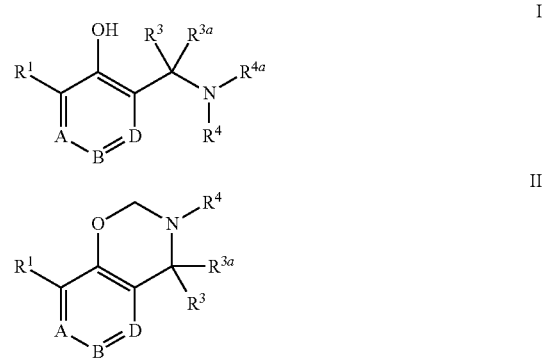

and pharmaceutically acceptable salts, enantiomers, and diastereoisomers thereof, wherein $R^1$ is heteroaryl attached through a carbon atom of the heteroaryl ring, optionally substituted with 1, 2, or 3 $R^5$;

A, B and D are independently are CH, $CR^2$ or N, provided that at least one of A, B, or D is $CR^2$;

$R^2$ is $C_{1-10}$ alkyl, $C_{1-10}$ haloalkyl, halo, cyano, $C_{3-10}$ cycloalkyl, $C_{1-6}$ alkylsulfonyl, $C_{6-10}$ aryl, optionally substituted with 1, 2, or 3 $R^5$, or heteroaryl attached through a carbon atom of the heteroaryl ring optionally substituted with 1, 2, or 3 $R^5$;

$R^3$ and $R^{3a}$ independently are hydrogen, $C_{1-10}$ alkyl, $C_{1-10}$ haloalkyl, or $C_{3-10}$ cycloalkyl;

$R^4$ and $R^{4a}$ independently are hydrogen, $C_{1-10}$ alkyl, $C_{1-10}$ haloalkyl, $C_{3-10}$ cycloalkyl, $C_{1-10}$alk$C_{3-10}$cycloalkyl, or $C_{1-10}$alkNR$^7$R$^{7a}$, wherein $R^7$ and $R^{7a}$ are independently H or $C_{1-10}$alkyl; or $R^4$ and $R^{4a}$, together with the nitrogen through which they are attached, form a heterocyclic ring of 4 to 7 ring atoms, where one carbon ring atom may be optionally replaced with $NR^6$, O, S, or $SO_2$, and where any carbon ring atom may be optionally substituted with $C_{1-6}$ alkyl, $C_{1-6}$ haloalkyl, $C_{1-6}$ alkoxy, or $C_{3-10}$ cycloalkyl;

each $R^5$ is independently halo, cyano, hydroxy, $C_{1-10}$ alkyl, $C_{1-10}$ haloalkyl, $C_{1-10}$ alkoxy, $C_{1-10}$ haloalkoxy, $C_{3-10}$ cycloalkyl, $C_{3-10}$ cycloalkoxy, amino, $C_{1-10}$ alkylamino, $C_{1-10}$ dialkylamino, $C_{3-10}$ cycloalkyamino, pyrrolidinyl, $C_{1-10}$ alkylsulfonyl, sulfamoyl, $C_{1-10}$ alkylsulfamoyl or $C_{1-10}$ dialkylsulfamoyl; and $R^6$ is $C_{1-10}$ alkyl, $C_{1-10}$ haloalkyl, $C_{3-10}$ cycloalkyl, or acetyl.

Methods of treating malaria using compounds of the invention, as well as methods of making the compounds of the invention, are also described.

DETAILED DESCRIPTION OF ILLUSTRATIVE EMBODIMENTS

It is to be understood that this invention is not limited to the specific products, methods, conditions or parameters described and/or shown herein, and that the terminology used herein is for the purpose of describing particular embodiments by way of example only and is not intended to be limiting of any claimed invention. Similarly, unless specifically stated otherwise, any description as to a possible mechanism or mode of action or reason for improvement is meant to be illustrative only, and the invention herein is not to be constrained by the correctness or incorrectness of any such suggested mechanism or mode of action or reason for improvement.

The present invention is directed to compounds of Formula I:

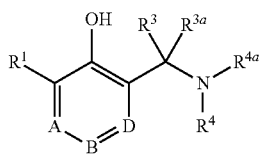

wherein $R^1$ is heteroaryl attached through a carbon atom of the heteroaryl ring, optionally substituted with 1, 2, or 3 $R^5$;

A, B and D are independently are CH, $CR^2$ or N, provided that at least one of A, B, or D is $CR^2$;

$R^2$ is $C_{1-10}$ alkyl, $C_{1-10}$ haloalkyl, halo, cyano, $C_{3-10}$ cycloalkyl, —$SO_2C_{1-10}$alkyl, $C_{6-10}$ aryl optionally substituted with 1, 2, or 3 $R^5$, or heteroaryl attached through a carbon atom of the heteroaryl ring optionally substituted with 1, 2, or 3 $R^5$;

$R^3$ and $R^{3a}$ independently are hydrogen, $C_{1-10}$ alkyl, $C_{1-10}$ haloalkyl, $C_{1-6}$ alkoxy, or $C_{3-10}$ cycloalkyl;

$R^4$ and $R^{4a}$ independently are hydrogen, $C_{1-10}$ alkyl, $C_{1-10}$haloalkyl, or $C_{3-10}$ cycloalkyl, or $R^4$ and $R^{4a}$ independently are hydrogen, $C_{1-10}$ alkyl, $C_{1-10}$ haloalkyl, $C_{3-10}$ cycloalkyl, $C_{1-10}$alk$C_{3-10}$cycloalkyl, or $C_{1-10}$alk$NR^7R^{7a}$, wherein $R^7$ and $R^{7a}$ are independently H or $C_{1-10}$alkyl; or $R^4$ and $R^{4a}$ together with the nitrogen through which they are attached, form a heterocyclic ring of 4 to 7 ring atoms, where one carbon ring atom may be optionally replaced with $NR^6$, O, S, or $SO_2$, and where any carbon ring atom may be optionally substituted with $C_{1-6}$ alkyl, $C_{1-6}$ haloalkyl, $C_{1-6}$ alkoxy, or $C_{3-10}$ cycloalkyl;

each $R^5$ is independently halo, cyano, hydroxy, $C_{1-10}$ alkyl, $C_{1-10}$ haloalkyl, $C_{1-10}$ alkoxy, $C_{1-10}$ haloalkoxy, $C_{3-10}$ cycloalkyl, $C_{3-10}$ cycloalkoxy, amino, $C_{1-10}$ alkylamino, $C_{1-10}$ dialkylamino, $C_{3-10}$ cycloalkyamino, pyrrolidinyl, $C_{1-10}$ alkylsulfonyl, sulfamoyl, $C_{1-10}$ alkylsulfamoyl, or $C_{1-10}$ dialkylsulfamoyl; and $R^6$ is $C_{1-10}$ alkyl, $C_{1-10}$ haloalkyl, or $C_{3-10}$ cycloalkyl or acetyl.

The pharmaceutically acceptable salts, enantiomers, and diastereoisomers of compounds of Formula I are also within the scope of the invention.

Examples of compounds of Formula I include compounds and pharmaceutically acceptable salts, enantiomers, or diastereoisomers thereof, wherein A and D are CH, and B is $CR^2$. In other embodiments, B and D are CH and A is $CR^2$. In yet other embodiments, A and B are CH and D is $CR^2$. In still other embodiments, one of A, B, and D is N and the others are CH or $CR^2$.

Examples of compounds of Formula I include compounds and pharmaceutically acceptable salts, enantiomers, or diastereoisomers thereof, wherein $R^3$ and $R^{3a}$ are each H. In some embodiments, $R^3$ is H and $R^{3a}$ is $C_{1-10}$alkyl, $C_{1-10}$ haloalkyl, $C_{1-6}$ alkoxy, or $C_{3-10}$ cycloalkyl. In yet other embodiments, $R^3$ is H and $R^{3a}$ is $C_{1-10}$alkyl, for example, methyl or ethyl, preferably methyl. In still other embodiments, $R^3$ is H and $R^{3a}$ is $C_{1-10}$ haloalkyl, for example, —$CF_3$. In other embodiments, $R^3$ is H and $R^{3a}$ is $C_{1-6}$ alkoxy, for example, methoxy, ethoxy, or propoxy. In some embodiments, $R^3$ is H and $R^{3a}$ is $C_{3-10}$ cycloalkyl, for example, cyclopropyl, cyclobutyl, cyclopentyl, or cyclohexyl.

Examples of compounds of Formula I include compounds and pharmaceutically acceptable salts, enantiomers, or diastereoisomers thereof, wherein $R^4$ is tert-butyl and $R^{4a}$ is H. In other embodiments, $R^4$ is $C_{1-10}$ alkyl, for example, methyl, ethyl, propyl, isopropyl, or butyl and $R^{4a}$ is H or $C_{1-10}$ alkyl, for example, methyl or ethyl. In yet other embodiments, $R^4$ is $C_{1-10}$ haloalkyl, for example trifluomethylpropyl, and $R^{4a}$ is H or $C_{1-10}$ alkyl, for example, methyl or ethyl. In still other embodiments, $R^4$ is $C_{3-10}$ cycloalkyl and $R^{4a}$ is H or $C_{1-10}$ alkyl, for example, methyl or ethyl. In yet other embodiments, $R^4$ is $C_{1-10}$alk$C_{3-10}$cycloalkyl and $R^{4a}$ is H or $C_{1-10}$ alkyl for example, methyl or ethyl. In yet other embodiments, $R^4$ is $C_{1-10}$alk$NR^7R^{7a}$ and $R^{4a}$ is H or $C_{1-10}$ alkyl, for example, methyl or ethyl, and wherein $R^7$ and $R^{7a}$ are independently H or $C_{1-10}$alkyl. Examples of $C_{1-10}$alk$NR^7R^{7a}$ include, for example, —$(CH_2)_xN(Et)_2$, —$(CH_2)_xN(Me)(Et)$, —$(CH_2)_xNH(Et)$, wherein x is 1-10, preferably 1-5, 1-4, 1-3, 1, or 2.

Examples of compounds of Formula I include compounds and pharmaceutically acceptable salts, enantiomers, or diastereoisomers thereof, wherein $R^2$ is $C_{1-10}$alkyl, preferably tert-butyl, $C_{6-10}$ aryl, or heteroaryl, wherein said aryl or heteroaryl is optionally substituted with 1, 2, or 3 $R^5$. Preferred $C_{6-10}$ aryl groups include phenyl and naphthyl optionally substituted with 1, 2, or 3 $R^5$. Preferred heteroaryl groups include 1-, 2-, or 3-pyridinyl, pyrimidinyl, and pyridazinyl.

When $R^2$ is $C_{6-10}$ aryl substituted with 1, 2, or 3 of $R^5$, each $R^5$ is halo, cyano, hydroxy, $C_{1-10}$ alkyl, $C_{1-10}$ haloalkyl, $C_{1-10}$ alkoxy, $C_{1-10}$haloalkoxy, $C_{3-10}$ cycloalkyl, $C_{3-10}$ cycloalkoxy, amino, $C_{1-10}$ alkylamino, $C_{1-10}$ dialkylamino, $C_{3-10}$ cycloalkyamino, pyrrolidinyl, $C_{1-10}$ alkylsulfonyl, sulfamoyl, $C_{1-10}$ alkylsulfamoyl, or $C_{1-10}$ dialkylsulfamoyl. Halo and $C_{1-10}$ haloalkyl, for example —$CF_3$, are particularly preferred limitations for $R^5$.

When $R^2$ is heteroaryl substituted with 1, 2, or 3 of $R^5$, each $R^5$ is halo, cyano, hydroxy, $C_{1-10}$ alkyl, $C_{1-10}$ haloalkyl, $C_{1-10}$ alkoxy, $C_{1-10}$ haloalkoxy, $C_{3-10}$ cycloalkyl, $C_{3-10}$ cycloalkoxy, amino, $C_{1-10}$ alkylamino, $C_{1-10}$ dialkylamino, $C_{3-10}$ cycloalkyamino, pyrrolidinyl, —$SO_2C_{1-10}$ alkyl, sulfamoyl, $C_{1-10}$ alkylsulfamoyl, or $C_{1-10}$ dialkylsulfamoyl. Halo and $C_{1-10}$ haloalkyl, for example —$CF_3$, are particularly preferred limitations for $R^5$.

In some embodiments, $R^4$ and $R^{4a}$ together with the nitrogen through which they are attached, form a heterocyclic ring of 4 to 7 ring atoms, for example, to form a piperidinyl, piperazinyl, pyrrolidinyl, or morpholinyl ring. In some embodiments, one carbon of the heterocyclic ring is replaced with $NR^6$, O, S, or $SO_2$, and any carbon ring atom may be optionally substituted with $C_{1-6}$ alkyl, $C_{1-6}$ haloalkyl, $C_{1-6}$ alkoxy, or $C_{3-10}$ cycloalkyl. Where one carbon of the heterocyclic ring is replace with $NR^6$, $R^6$ is preferably $C_{1-10}$ alkyl, $C_{1-10}$ haloalkyl, or $C_{3-10}$ cycloalkyl, or acetyl.

Examples of compounds of Formula I include compounds and pharmaceutically acceptable salts, enantiomers, or diastereoisomers thereof, wherein $R^1$ is a pyridyl, pyrimidinyl, pyrazinyl, or thienyl group. In certain embodiments, the pyridyl, pyrimidinyl, pyrazinyl, or thienyl group is substituted with 1, 2, or 3 $R^5$. In other embodiments, $R^1$ is quinolinyl, isoquinolinyl, benzothiophenyl, benzofuranyl, pyrazolyl, or methylpyrazolyl. In some embodiments, the quinolinyl, isoquinolinyl, benzothiophenyl, benzofuranyl, pyrazolyl, or methylpyrazolyl is substituted with 1, 2, or 3 $R^5$. In some embodiments, $R^1$ is a pyridyl, pyrimidinyl, pyrazinyl, thienyl, quinolinyl, isoquinolinyl, benzothiophenyl, benzofuranyl, pyrazolyl, or methylpyrazolyl group substituted with 1, 2, or 3 $R^5$. Preferred limitations for $R^5$, in these embodiments, are $C_{1-10}$haloalkyl, for example, —$CF_3$, halo, $C_{3-10}$cycloalkyl, for example cyclopropyl, $C_{1-10}$alkyl, for example, methyl, ethyl, propyl, isopropyl, butyl, and tert-butyl, —CN, $C_{1-10}$alkoxy, for example, methoxy, ethoxy and propoxy.

Preferred compounds of Formula I include compounds and pharmaceutically acceptable salts, enantiomers, or diastereoisomers thereof, wherein A and D are CH, and B is $CR^2$; $R^3$ and $R^{3a}$ are H; $R^4$ is tert-butyl and $R^{4a}$ is H; $R^2$ is tert-butyl, $C_{6-10}$ aryl, or heteroaryl, wherein said aryl or heteroaryl is optionally substituted with 1, 2, or 3 $R^5$; and $R^1$ is pyridyl, pyrimidinyl, pyrazinyl, or thienyl group optionally substituted with 1, 2, or 3 $R^5$.

Examples of compounds of Formula I include compounds and pharmaceutically acceptable salts, enantiomers, or diastereoisomers thereof, wherein A and D are CH, and B is $CR^2$; $R^3$ and $R^{3a}$ are H; $R^4$ is tert-butyl and $R^{4a}$ is H; $R^2$ is tert-butyl; and $R^1$ is pyridyl, pyrimidinyl, pyrazinyl, or thienyl group optionally substituted with 1, 2, or 3 $R^5$.

Preferred compounds of Formula I include compounds of formula IA:

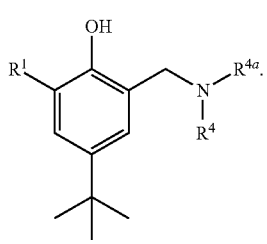

IA

Preferred compounds of Formula IA include those wherein $R^1$ is pyridyl, thiophenyl, quinolinyl, isoquinolinyl, benzofuranyl, benzothiophenyl, pyrazolyl, pyrazinyl, or pyrimidinyl, each optionally substituted with 1, 2, or 3 $R^5$.

Preferred compounds of Formula IA also include those wherein $R^1$ is thiophenyl, benzofuranyl, benzothiophenyl, pyrazolyl, pyrazinyl, or pyrimidinyl, each optionally substituted with 1, 2, or 3 $R^5$.

Other preferred compounds of Formula IA include those wherein $R^4$ and $R^{4a}$ are independently hydrogen or $C_{1-6}$ alkyl.

In some embodiments, of compounds of Formula IA, $R^4$ and $R^{4a}$ together with the nitrogen through which they are attached, form a heterocyclic ring of 4 to 7 ring atoms, for example, a piperidinyl, piperazinyl, pyrrolidinyl, or morpholinyl ring.

Exemplary compounds of Formula IA include:

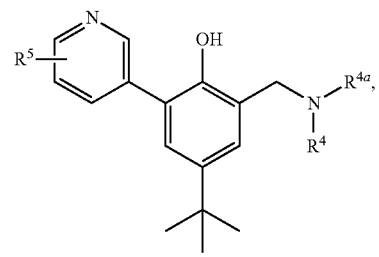

IA-1

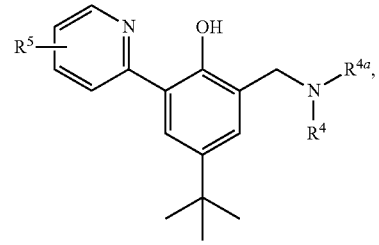

IA-2

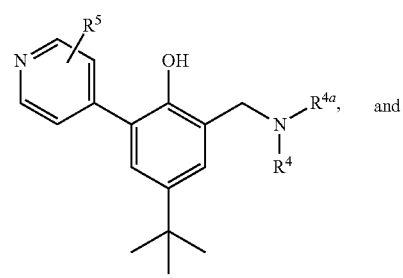

IA-3 and

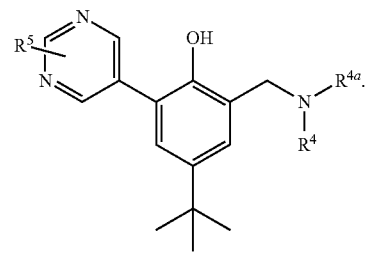

IA-4

Other exemplary compounds of formula IA include:

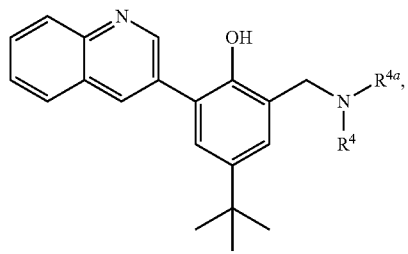
IA-4

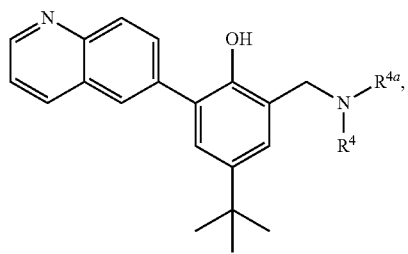
IA-5

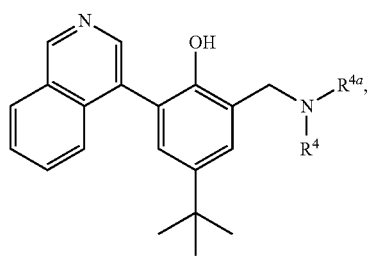
IA-6

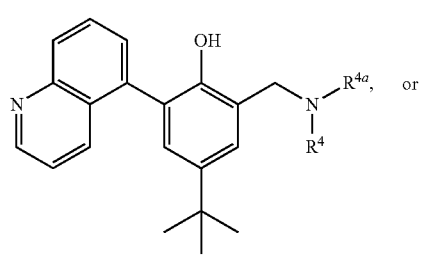
IA-7

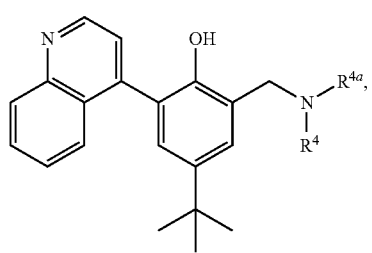
IA-8 wherein each quinolinyl or isoquinolinyl of IA-4, IA-5, IA-6, IA-7, or IA-8 is optionally substituted with 1, 2, or 3 $R^5$.

In other preferred embodiments of the compounds of Formula IA, $R^5$, when present, is —$CF_3$, F, Cl, Br, —$NH_2$, —$OC_{1-6}$alkyl, —CN, —$N(CH_3)_2$, $C_{1-10}$alkyl, $C_{1-10}$alkylsulfonyl,

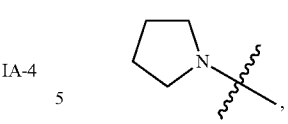

or —$C_{3-6}$cycloalkyl.

Examples of compounds of Formula I include:

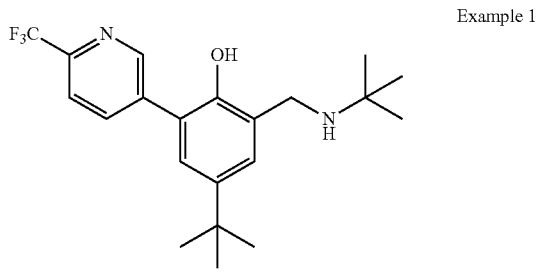
Example 1

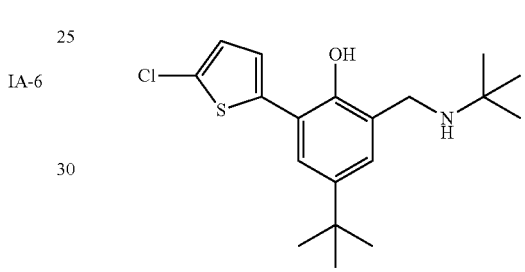
Example 2

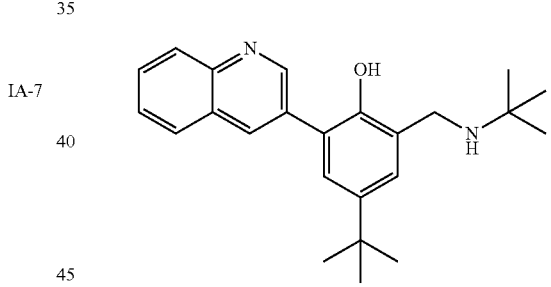
Example 3

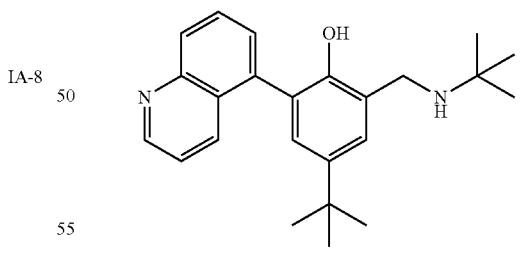
Example 4

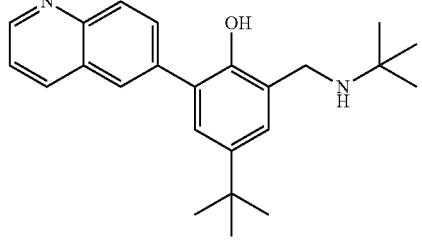
Example 5

Example 6
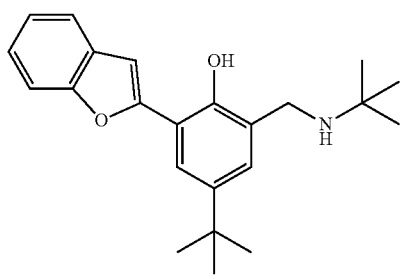
Example 7
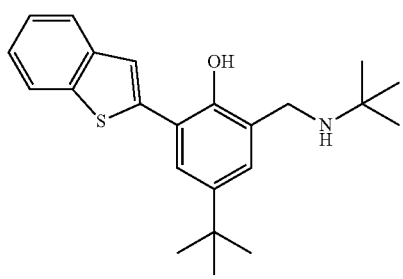
Example 8
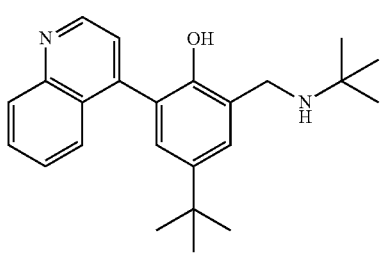
Example 9
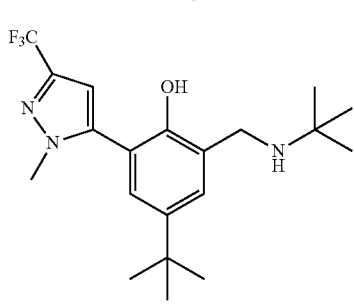
Example 10
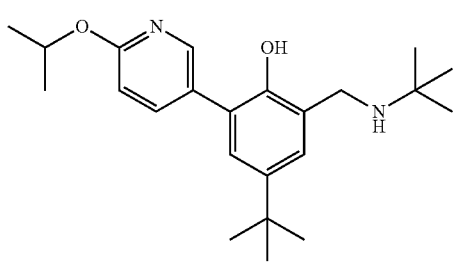
Example 11
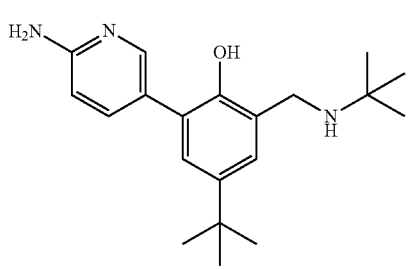
Example 12
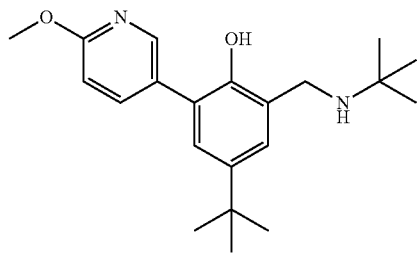
Example 13
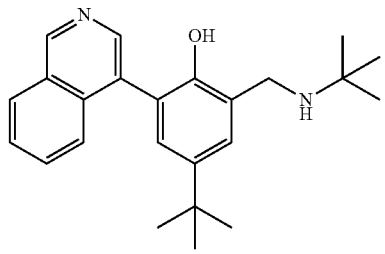
Example 14
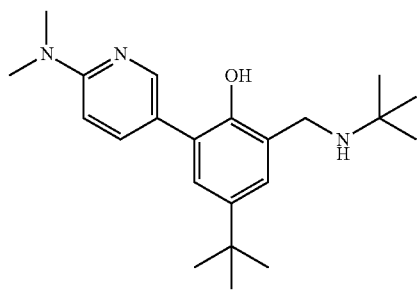
Example 15
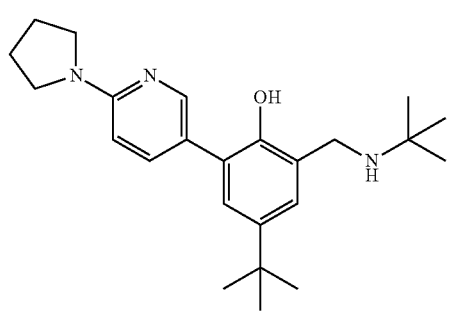
Example 16
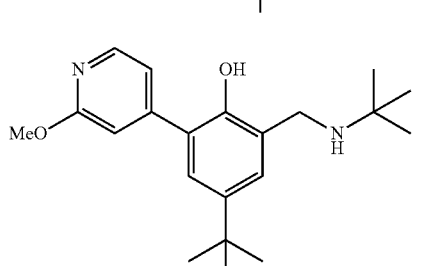
Example 17
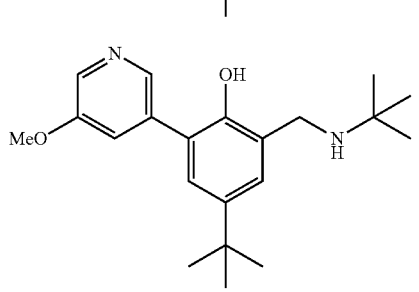

Example 18

Example 19

Example 20

Example 21

Example 22

Example 23

Example 24

Example 25

Example 26

Example 27

Example 28

Example 29

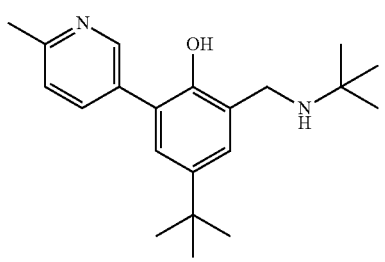
Example 30
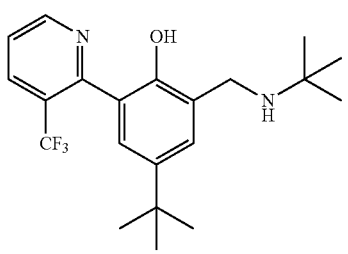
Example 31
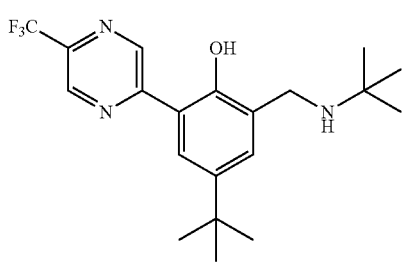
Example 32
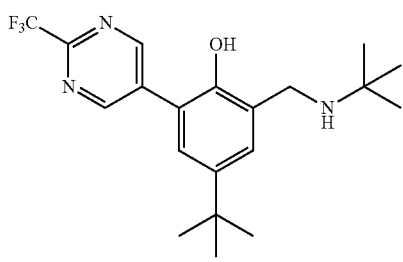
Example 33
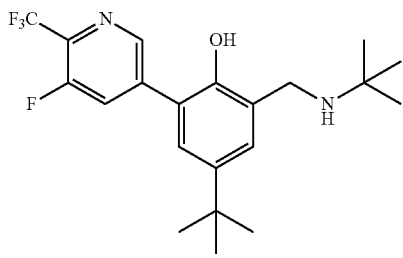
Example 34
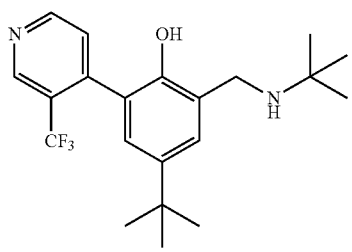
Example 35
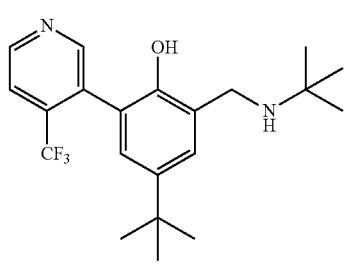
Example 36
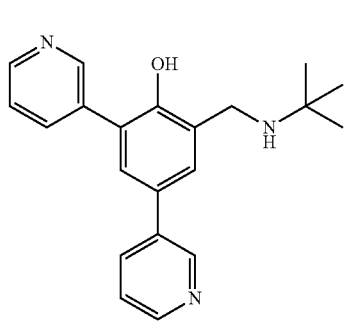
Example 37
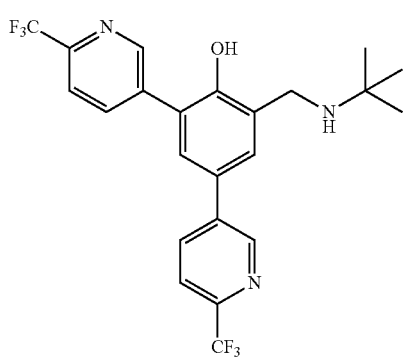
Example 38
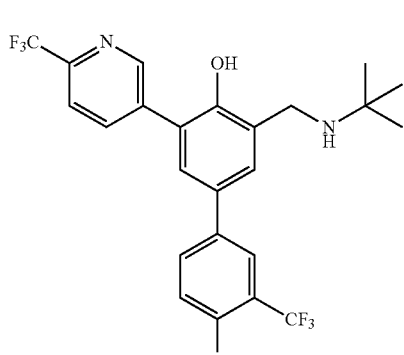
Example 39
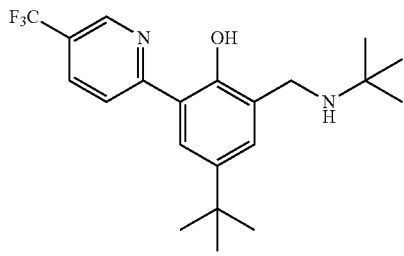
Example 40

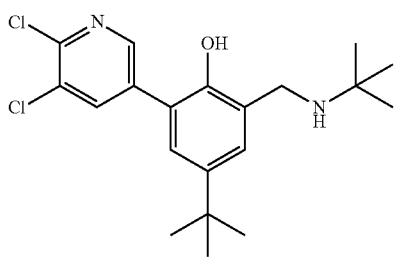
Example 41
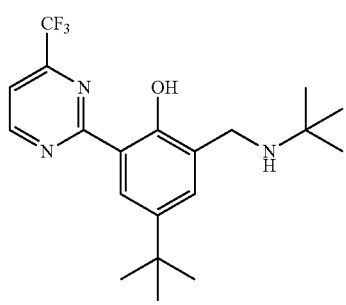
Example 46
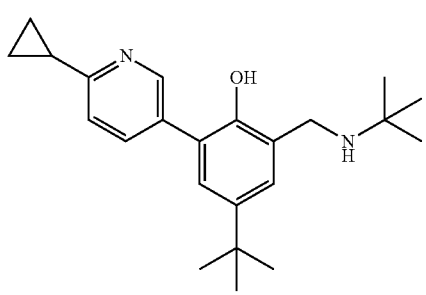
Example 42
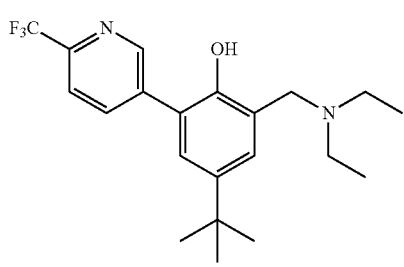
Example 47
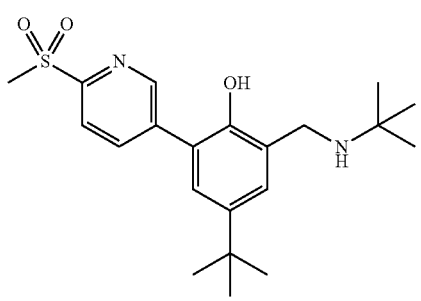
Example 43
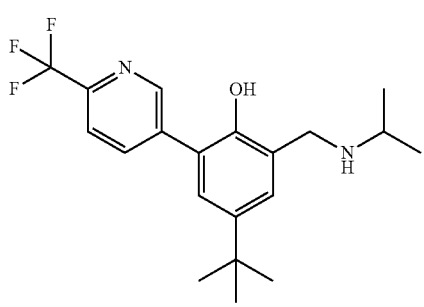
Example 48
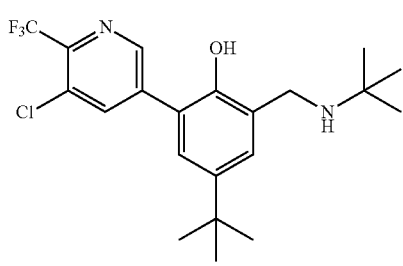
Example 44
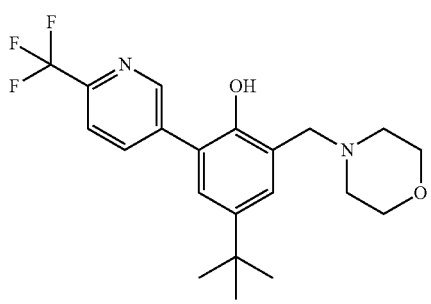
Example 49
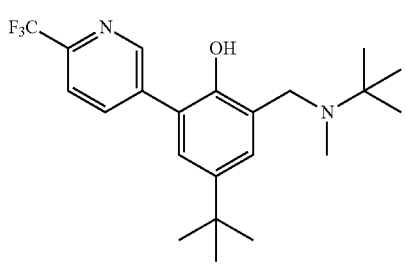
Example 45
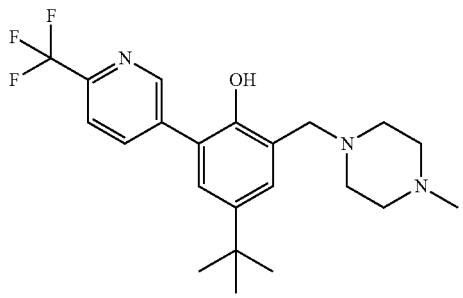
Example 50

-continued
Example 51
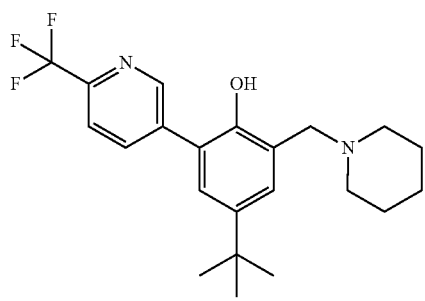
Example 52
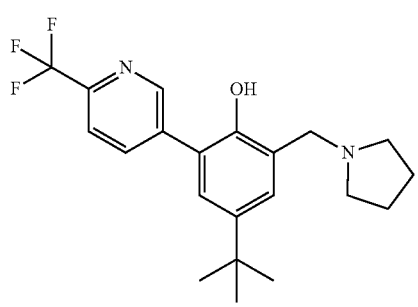
Example 53
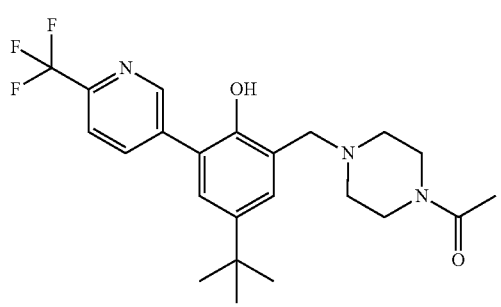
Example 54
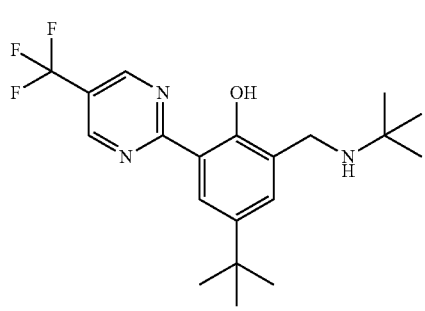
Example 55
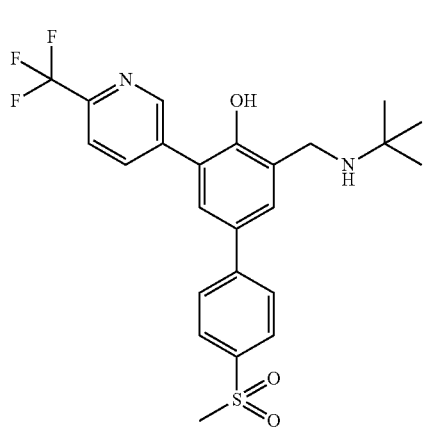
-continued
Example 56
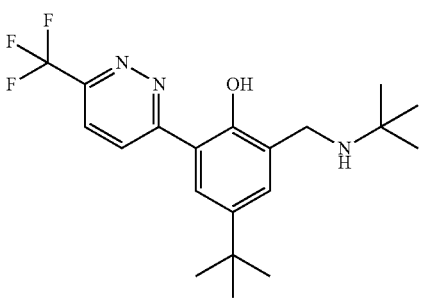
Example 57
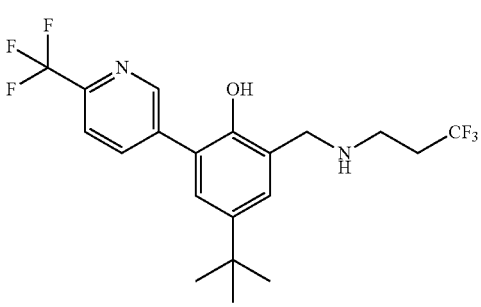
Example 58
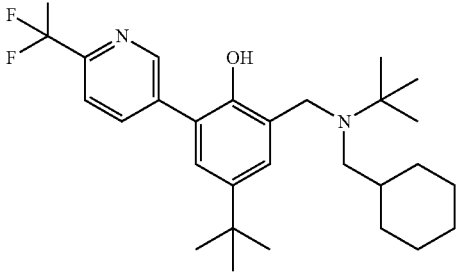
Example 59
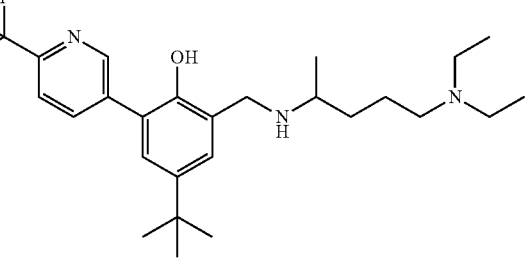
Example 60
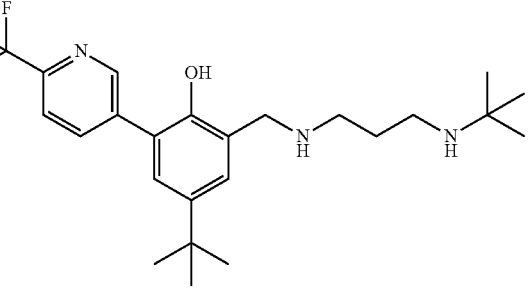

-continued

Example 61

Example 62

Example 63

Example 64

Example 65

Example 66

Example 67

Example 68

Example 69

Example 70

-continued

Example 71

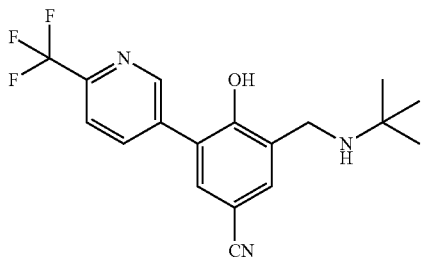

Example 72

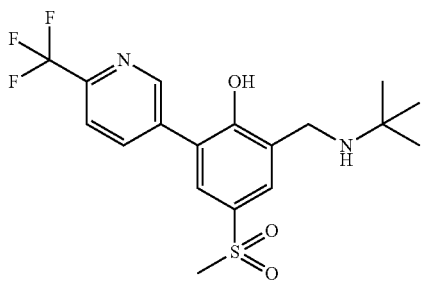

Example 73

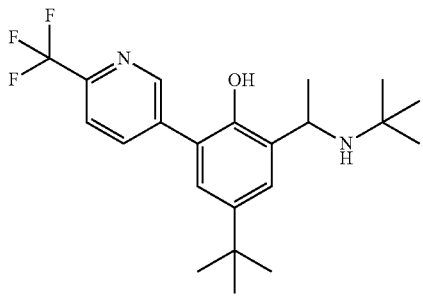

Example 74

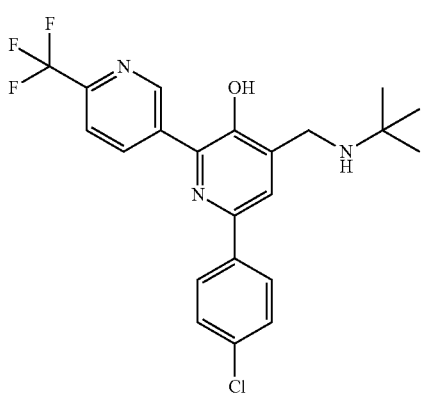

(1) 4-(tert-butyl)-2-((tert-butylamino)methyl)-6-(6-(trifluoromethyl)pyridin-3-yl)phenol
(2) 4-(tert-butyl)-2-((tert-butylamino)methyl)-6-(5-chlorothiophen-2-yl)phenol
(3) 4-(tert-butyl)-2-((tert-butylamino)methyl)-6-(quinolin-3-yl)phenol
(4) 4-(tert-butyl)-2-((tert-butylamino)methyl)-6-(quinolin-5-yl)phenol
(5) 4-(tert-butyl)-2-((tert-butylamino)methyl)-6-(quinolin-6-yl)phenol
(6) 2-(benzofuran-2-yl)-4-(tert-butyl)-6-((tert-butylamino)methyl)phenol
(7) 2-(benzo[b]thiophen-2-yl)-4-(tert-butyl)-6-((tert-butylamino)methyl)phenol
(8) 4-(tert-butyl)-2-((tert-butylamino)methyl)-6-(quinolin-4-yl)phenol
(9) 4-(tert-butyl)-2-((tert-butylamino)methyl)-6-(1-methyl-3-(trifluoromethyl)-1H-pyrazol-5-yl)phenol
(10) 4-(tert-butyl)-2-((tert-butylamino)methyl)-6-(6-isopropoxypyridin-3-yl)phenol
(11) 2-(6-aminopyridin-3-yl)-4-(tert-butyl)-6-((tert-butylamino)methyl)phenol
(12) 4-(tert-butyl)-2-((tert-butylamino)methyl)-6-(6-methoxypyridin-3-yl)phenol
(13) 4-(tert-butyl)-2-((tert-butylamino)methyl)-6-(isoquinolin-4-yl)phenol
(14) 4-(tert-butyl)-2-((tert-butylamino)methyl)-6-(6-(dimethylamino)pyridin-3-yl)phenol
(15) 4-(tert-butyl)-2-((tert-butylamino)methyl)-6-(6-(pyrrolidin-1-yl)pyridin-3-yl)phenol
(16) 4-(tert-butyl)-2-((tert-butylamino)methyl)-6-(2-methoxypyridin-4-yl)phenol
(17) 4-(tert-butyl)-2-((tert-butylamino)methyl)-6-(5-methoxypyridin-3-yl)phenol
(18) 4-(tert-butyl)-2-((tert-butylamino)methyl)-6-(5-(trifluoromethyl)pyridin-3-yl)phenol
(19) 5-(5-(tert-butyl)-3-((tert-butylamino)methyl)-2-hydroxyphenyl)picolinonitrile
(20) 4-(tert-butyl)-2-((tert-butylamino)methyl)-6-(2-(trifluoromethyl)pyridin-4-yl)phenol
(21) 4-(tert-butyl)-2-((tert-butylamino)methyl)-6-(5-chloropyridin-3-yl)phenol
(22) 4-(tert-butyl)-2-(6-(tert-butyl)pyridin-3-yl)-6-((tert-butylamino)methyl)phenol
(23) 4-(tert-butyl)-2-((tert-butylamino)methyl)-6-(6-chloropyridin-3-yl)phenol
(24) 4-(tert-butyl)-2-((tert-butylamino)methyl)-6-(pyrimidin-5-yl)phenol
(25) 4-(tert-butyl)-2-((tert-butylamino)methyl)-6-(5-methylpyridin-2-yl)phenol
(26) 4-(tert-butyl)-2-((tert-butylamino)methyl)-6-(5-fluoropyridin-2-yl)phenol
(27) 4-(tert-butyl)-2-((tert-butylamino)methyl)-6-(3-fluoropyridin-2-yl)phenol
(28) 4-(tert-butyl)-2-((tert-butylamino)methyl)-6-(4-(trifluoromethyl)pyridin-2-yl)phenol
(29) 4-(tert-butyl)-2-((tert-butylamino)methyl)-6-(6-(trifluoromethyl)pyridin-2-yl)phenol
(30) 4-(tert-butyl)-2-((tert-butylamino)methyl)-6-(6-methylpyridin-3-yl)phenol
(31) 4-(tert-butyl)-2-((tert-butylamino)methyl)-6-(3-(trifluoromethyl)pyridin-2-yl)phenol
(32) 4-(tert-butyl)-2-((tert-butylamino)methyl)-6-(5-(trifluoromethyl)pyrazin-2-yl)phenol
(33) 4-(tert-butyl)-2-((tert-butylamino)methyl)-6-(2-(trifluoromethyl)pyrimidin-5-yl)phenol
(34) 4-(tert-butyl)-2-((tert-butylamino)methyl)-6-(5-fluoro-6-(trifluoromethyl)pyridin-3-yl)phenol
(35) 4-(tert-butyl)-2-((tert-butylamino)methyl)-6-(3-(trifluoromethyl)pyridin-4-yl)phenol
(36) 4-(tert-butyl)-2-((tert-butylamino)methyl)-6-(4-(trifluoromethyl)pyridin-3-yl)phenol
(37) 2-((tert-butylamino)methyl)-4,6-di(pyridin-3-yl)phenol
(38) 2-((tert-butylamino)methyl)-4,6-bis(6-(trifluoromethyl)pyridin-3-yl)phenol
(39) 3-((tert-butylamino)methyl)-4'-chloro-3'-(trifluoromethyl)-5-(6-(trifluoromethyl)pyridin-3-yl)-[1,1'-biphenyl]-4-ol
(40) 4-(tert-butyl)-2-((tert-butylamino)methyl)-6-(5-(trifluoromethyl)pyridin-2-yl)phenol
(41) 4-(tert-butyl)-2-((tert-butylamino)methyl)-6-(5,6-dichloropyridin-3-yl)phenol

(42) 4-(tert-butyl)-2-((tert-butylamino)methyl)-6-(6-cyclopropylpyridin-3-yl)phenol
(43) 4-(tert-butyl)-2-((tert-butylamino)methyl)-6-(6-(methylsulfonyl)pyridin-3-yl)phenol
(44) 4-(tert-butyl)-2-((tert-butylamino)methyl)-6-(5-chloro-6-(trifluoromethyl)pyridin-3-yl)phenol
(45) 4-(tert-butyl)-2-((tert-butyl(methyl)amino)methyl)-6-(6-(trifluoromethyl)pyridin-3-yl)phenol
(46) 4-(tert-butyl)-2-((tert-butylamino)methyl)-6-(4-(trifluoromethyl)pyrimidin-2-yl)phenol
(47) 4-(tert-butyl)-2-((diethylamino)methyl)-6-(6-(trifluoromethyl)pyridin-3-yl)phenol
(48) 4-(tert-butyl)-2-((isopropylamino)methyl)-6-(6-(trifluoromethyl)pyridin-3-yl)phenol
(49) 4-(tert-butyl)-2-(morpholinomethyl)-6-(6-(trifluoromethyl)pyridin-3-yl)phenol
(50) 4-(tert-butyl)-2-((4-methylpiperazin-1-yl)methyl)-6-(6-(trifluoromethyl)pyridin-3-yl)phenol
(51) 4-(tert-butyl)-2-(piperidin-1-ylmethyl)-6-(6-(trifluoromethyl)pyridin-3-yl)phenol
(52) 4-(tert-butyl)-2-(pyrrolidin-1-ylmethyl)-6-(6-(trifluoromethyl)pyridin-3-yl)phenol
(53) 1-(4-(5-(tert-butyl)-2-hydroxy-3-(6-(trifluoromethyl)pyridin-3-yl)benzyl)piperazin-1-yl)ethanone
(54) 4-(tert-butyl)-2-((tert-butylamino)methyl)-6-(5-(trifluoromethyl)pyrimidin-2-yl)phenol
(55) 3-((tert-butylamino)methyl)-4'-(methylsulfonyl)-5-(6-(trifluoromethyl)pyridin-3-yl)-[1,1'-biphenyl]-4-ol
(56) 4-(tert-butyl)-2-((tert-butylamino)methyl)-6-(6-(trifluoromethyl)pyridazin-3-yl)phenol
(57) 4-(tert-butyl)-2-(6-(trifluoromethyl)pyridin-3-yl)-6-(3,3,3-trifluoropropyl)amino)methyl)phenol
(58) 4-(tert-butyl)-2-((tert-butyl(cyclohexylmethyl)amino)methyl)-6-(6-(trifluoromethyl)pyridin-3-yl)phenol
(59) 4-(tert-butyl)-2-(5-(diethylamino)pentan-2-yl)amino)methyl)-6-(6-(trifluoromethyl)pyridin-3-yl)phenol
(60) 4-(tert-butyl)-2-(3-(tert-butylamino)propyl)amino)methyl)-6-(6-(trifluoromethyl)pyridin-3-yl)phenol
(61) 4-(tert-butyl)-2-(3-(diethylamino)propyl)amino)methyl)-6-(6-(trifluoromethyl)pyridin-3-yl)phenol
(62) 2-(((3-aminopropyl)amino)methyl)-4-(tert-butyl)-6-(6-(trifluoromethyl)pyridin-3-yl)phenol
(63) 4-(tert-butyl)-2-(((2-(diethylamino)ethyl)amino)methyl)-6-(6-(trifluoromethyl)pyridin-3-yl)phenol
(64) 2-(aminomethyl)-4-(tert-butyl)-6-(6-(trifluoromethyl)pyridin-3-yl)phenol
(65) 2-(((1-aminopropan-2-yl)amino)methyl)-4-(tert-butyl)-6-(6-(trifluoromethyl)pyridin-3-yl)phenol
(66) 3-((tert-butylamino)methyl)-4'-fluoro-5-(6-(trifluoromethyl)pyridin-3-yl)-[1,1'-biphenyl]-4-ol
(67) 3-((tert-butylamino)methyl)-3'-fluoro-5-(6-(trifluoromethyl)pyridin-3-yl)-[1,1'-biphenyl]-4-ol
(68) 2-((tert-butylamino)methyl)-4-fluoro-6-(6-(trifluoromethyl)pyridin-3-yl)phenol
(69) 2-((tert-butylamino)methyl)-4-chloro-6-(6-(trifluoromethyl)pyridin-3-yl)phenol
(70) 3-((tert-butylamino)methyl)-4'-chloro-5-(6-(trifluoromethyl)pyridin-3-yl)-[1,1'-biphenyl]-4-ol
(71) 3-((tert-butylamino)methyl)-4-hydroxy-5-(6-(trifluoromethyl)pyridin-3-yl)benzonitrile
(72) 2-((tert-butylamino)methyl)-4-(methylsulfonyl)-6-(6-(trifluoromethyl)pyridin-3-yl)phenol
(73) 4-(tert-butyl)-2-(1-(tert-butylamino)ethyl)-6-(6-(trifluoromethyl)pyridin-3-yl)phenol
(74) 4-((tert-butylamino)methyl)-6-(4-chlorophenyl)-6'-(trifluoromethyl)-[2,3'-bipyridin]-3-ol
and pharmaceutically acceptable salts thereof.

The present invention is also directed to compounds of Formula II:

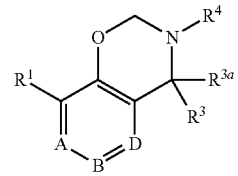

II wherein
$R^1$ is heteroaryl attached through a carbon atom of the heteroaryl ring, optionally substituted with 1, 2, or 3 $R^5$;
A, B and D are independently are CH, $CR^2$ or N, provided that at least one of A, B, or D is $CR^2$;
$R^2$ is $C_{1-10}$ alkyl, $C_{1-10}$ haloalkyl, halo, cyano, $C_{3-10}$ cycloalkyl, $-SO_2C_{1-10}$alkyl, $C_{6-10}$ aryl optionally substituted with 1, 2, or 3 $R^5$, or heteroaryl attached through a carbon atom of the heteroaryl ring optionally substituted with 1, 2, or 3 $R^5$;
$R^3$ and $R^{3a}$ independently are hydrogen, $C_{1-10}$ alkyl, $C_{1-10}$ haloalkyl, $C_{1-6}$ alkoxy, or $C_{3-10}$ cycloalkyl;
$R^4$ is hydrogen, $C_{1-10}$alkyl, $C_{1-10}$ haloalkyl, $C_{3-10}$ cycloalkyl, $C_{1-10}$alkC$_{3-10}$cycloalkyl, or $C_{1-10}$alkNR$^7$R$^{7a}$, wherein $R^7$ and $R^{7a}$ are independently H or $C_{1-10}$alkyl; and
each $R^5$ is independently halo, cyano, hydroxy, $C_{1-10}$ alkyl, $C_{1-10}$ haloalkyl, $C_{1-10}$ alkoxy, $C_{1-10}$ haloalkoxy, $C_{3-10}$ cycloalkyl, $C_{3-10}$ cycloalkoxy, amino, $C_{1-10}$ alkylamino, $C_{1-10}$ dialkylamino, $C_{3-10}$ cycloalkyamino, pyrrolidinyl, $C_{1-10}$alkylsulfonyl, sulfamoyl, $C_{1-10}$ alkylsulfamoyl, or $C_{1-10}$ dialkylsulfamoyl.

Examples of compounds of Formula II include compounds and pharmaceutically acceptable salts, enantiomers, or diastereoisomers thereof, wherein A and D are CH, and B is $CR^2$. In other embodiments, B and D are CH and A is $CR^2$. In yet other embodiments, A and B are CH and D is $CR^2$. In still other embodiments, one of A, B, and D is N and the others are CH or $CR^2$.

Examples of compounds of Formula II include compounds and pharmaceutically acceptable salts, enantiomers, or diastereoisomers thereof, wherein $R^3$ and $R^{3a}$ are each H. In some embodiments, $R^3$ is H and $R^{3a}$ is $C_{1-10}$alkyl, $C_{1-10}$ haloalkyl, $C_{1-6}$ alkoxy, or $C_{3-10}$ cycloalkyl. In yet other embodiments, $R^3$ is H and $R^{3a}$ is $C_{1-10}$alkyl, for example, methyl or ethyl, preferably methyl. In still other embodiments, $R^3$ is H and $R^{3a}$ is $C_{1-10}$ haloalkyl, for example, $-CF_3$. In other embodiments, $R^3$ is H and $R^{3a}$ is $C_{1-6}$ alkoxy, for example, methoxy, ethoxy, or propoxy. In some embodiments, $R^3$ is H and $R^{3a}$ is $C_{3-10}$ cycloalkyl, for example, cyclopropyl, cyclobutyl, cyclopentyl, or cyclohexyl.

Examples of compounds of Formula II include compounds and pharmaceutically acceptable salts, enantiomers, or diastereoisomers thereof, wherein $R^4$ is tert-butyl. In other embodiments, $R^4$ is $C_{1-10}$ alkyl, for example, methyl, ethyl, propyl, isopropyl, or butyl. In yet other embodiments, $R^4$ is $C_{1-10}$haloalkyl, for example trifluomethylpropyl. In still other embodiments, $R^4$ is $C_{3-10}$ cycloalkyl. In yet other embodiments, $R^4$ is $C_{1-10}$alkC$_{3-10}$cycloalkyl. In yet other embodiments, $R^4$ is $C_{1-10}$alkNR$^7$R$^{7a}$, wherein $R^7$ and $R^{7a}$ are independently H or $C_{1-10}$alkyl. Examples of $C_{1-10}$ alkNR$^7$R$^{7a}$ include, for example, $-(CH_2)_xN(Et)_2$, $-(CH_2)_xN(Me)(Et)$, $-(CH_2)_xNH(Et)$, wherein x is 1-10, preferably 1-5, 1-4, 1-3, 1, or 2.

Examples of compounds of Formula II include compounds and pharmaceutically acceptable salts, enantiomers, or diastereoisomers thereof, wherein $R^2$ is $C_{1-10}$alkyl, preferably tert-butyl, $C_{6-10}$ aryl, or heteroaryl, wherein said aryl or heteroaryl is optionally substituted with 1, 2, or 3 $R^5$. Preferred $C_{6-10}$ aryl groups include phenyl and naphthyl optionally substituted with 1, 2, or 3 $R^5$. Preferred heteroaryl groups include 1-, 2-, or 3-pyridinyl, pyrimidinyl, and pyridazinyl.

When $R^2$ is $C_{6-10}$ aryl substituted with 1, 2, or 3 of $R^5$, each $R^5$ is halo, cyano, hydroxy, $C_{1-10}$ alkyl, $C_{1-10}$ haloalkyl, $C_{1-10}$ alkoxy, $C_{1-10}$haloalkoxy, $C_{3-10}$ cycloalkyl, $C_{3-10}$ cycloalkoxy, amino, $C_{1-10}$ alkylamino, $C_{1-10}$ dialkylamino, $C_{3-10}$ cycloalkyamino, pyrrolidinyl, $C_{1-10}$ alkylsulfonyl, sulfamoyl, $C_{1-10}$ alkylsulfamoyl, or $C_{1-10}$ dialkylsulfamoyl. Halo and $C_{1-10}$ haloalkyl, for example —$CF_3$, are particularly preferred limitations for $R^5$.

When $R^2$ is heteroaryl substituted with 1, 2, or 3 of $R^5$, each $R^5$ is halo, cyano, hydroxy, $C_{1-10}$ alkyl, $C_{1-10}$ haloalkyl, $C_{1-10}$ alkoxy, $C_{1-10}$ haloalkoxy, $C_{3-10}$ cycloalkyl, $C_{3-10}$ cycloalkoxy, amino, $C_{1-10}$ alkylamino, $C_{1-10}$ dialkylamino, $C_{3-10}$ cycloalkyamino, pyrrolidinyl, —$SO_2C_{1-10}$ alkyl, sulfamoyl, $C_{1-10}$ alkylsulfamoyl, or $C_{1-10}$ dialkylsulfamoyl. Halo and $C_{1-10}$ haloalkyl, for example —$CF_3$, are particularly preferred limitations for $R^5$.

Examples of compounds of Formula II include compounds and pharmaceutically acceptable salts, enantiomers, or diastereoisomers thereof, wherein $R^1$ is a pyridyl, pyrimidinyl, pyrazinyl, or thienyl group. In certain embodiments, the pyridyl, pyrimidinyl, pyrazinyl, or thienyl group is substituted with 1, 2, or 3 $R^5$. In other embodiments, $R^1$ is quinolinyl, isoquinolinyl, benzothiophenyl, benzofuranyl, pyrazolyl, or methylpyrazolyl. In some embodiments, the quinolinyl, isoquinolinyl, benzothiophenyl, benzofuranyl, pyrazolyl, or methylpyrazolyl is substituted with 1, 2, or 3 $R^5$. In some embodiments, $R^1$ is a pyridyl, pyrimidinyl, pyrazinyl, thienyl, quinolinyl, isoquinolinyl, benzothiophenyl, benzofuranyl, pyrazolyl, or methylpyrazolyl group substituted with 1, 2, or 3 $R^5$. Preferred limitations for $R^5$, in these embodiments, are $C_{1-10}$haloalkyl, for example, —$CF_3$, halo, $C_{3-10}$cycloalkyl, for example cyclopropyl, $C_{1-10}$alkyl, for example, methyl, ethyl, propyl, isopropyl, butyl, and tert-butyl, —CN, $C_{1-10}$alkoxy, for example, methoxy, ethoxy and propoxy.

Preferred compounds of Formula II include compounds and pharmaceutically acceptable salts, enantiomers, or diastereoisomers thereof, wherein A and D are CH, and B is $CR^2$; $R^3$ and $R^{3a}$ are H; $R^4$ is tert-butyl and $R^{4a}$ is H; $R^2$ is tert-butyl, $C_{6-10}$ aryl, or heteroaryl, wherein said aryl or heteroaryl is optionally substituted with 1, 2, or 3 $R^5$; and $R^1$ is pyridyl, pyrimidinyl, pyrazinyl, or thienyl group optionally substituted with 1, 2, or 3 $R^5$.

Examples of compounds of Formula II include compounds and pharmaceutically acceptable salts, enantiomers, or diastereoisomers thereof, wherein A and D are CH, and B is $CR^2$; $R^3$ and $R^{3a}$ are H; $R^4$ is tert-butyl and $R^{4a}$ is H; $R^2$ is tert-butyl; and $R^1$ is pyridyl, pyrimidinyl, pyrazinyl, or thienyl group optionally substituted with 1, 2, or 3 $R^5$.

Preferred compounds of Formula II include compounds of formula IIA:

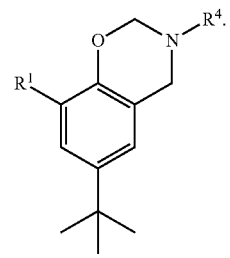

IIA

Preferred compounds of Formula IIA include those wherein $R^1$ is pyridyl, thiophenyl, quinolinyl, isoquinolinyl, benzofuranyl, benzothiophenyl, pyrazolyl, pyrazinyl, or pyrimidinyl, each optionally substituted with 1, 2, or 3 $R^5$.

Preferred compounds of Formula IIA also include those wherein $R^1$ is thiophenyl, benzofuranyl, benzothiophenyl, pyrazolyl, pyrazinyl, or pyrimidinyl, each optionally substituted with 1, 2, or 3 $R^5$.

Other preferred compounds of Formula IIA include those wherein $R^4$ and $R^{4a}$ are independently hydrogen or $C_{1-6}$ alkyl.

Exemplary compounds of Formula IIA include:

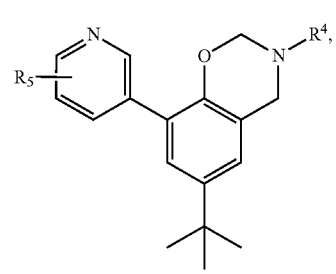

IIA-1

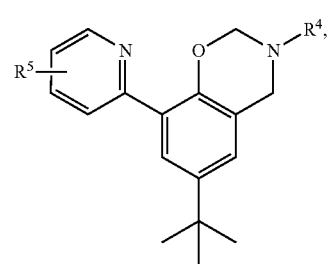

IIA-2

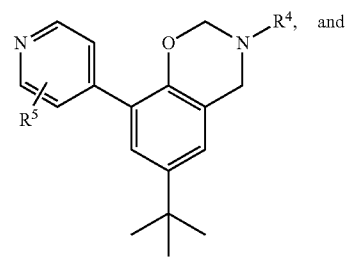

IIA-3 and

-continued

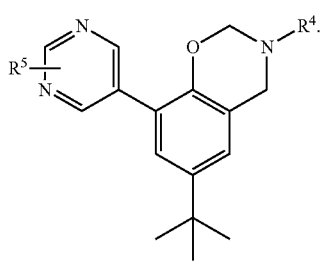
IIA-4

Other exemplary compounds of formula IIA include:

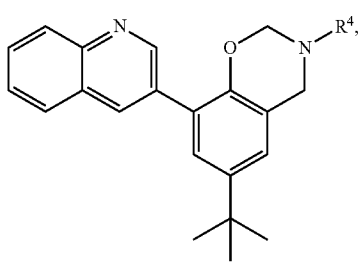
IIA-4

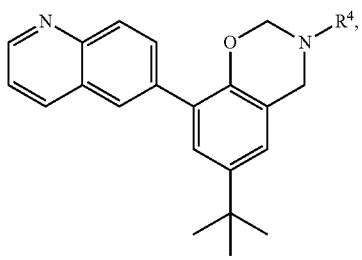
IIA-5

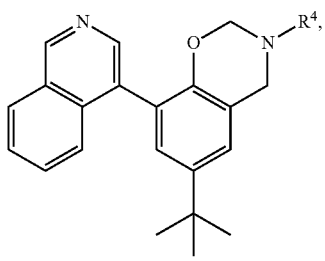
IIA-6

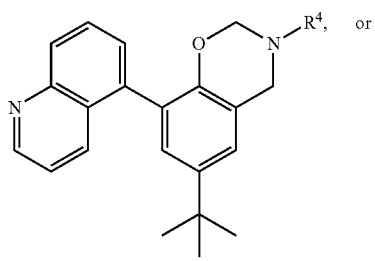
IIA-7

-continued

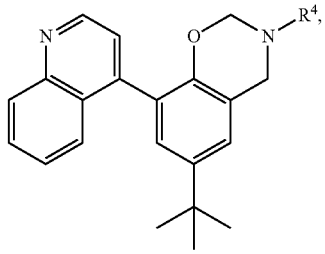
IIA-8 wherein each quinolinyl or isoquinolinyl of IIA-4, IIA-5, IA-6, IIA-7, or IIA-8 is optionally substituted with 1, 2, or 3 $R^5$.

In other preferred embodiments of the compounds of Formula IIA, $R^5$, when present, is
—$CF_3$, F, Cl, Br, —$NH_2$, —$OC_{1-6}$alkyl, —CN, —$N(CH_3)_2$, $C_{1-10}$alkyl, $C_{1-10}$alkylsulfonyl,

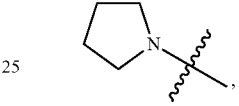

or —$C_{3-6}$cycloalkyl.

A particularly preferred compound of Formula II is

Example 75

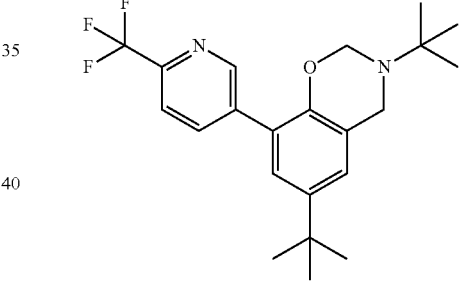

(75) 3,6-di-tert-butyl-8-(6-(trifluoromethyl)pyridin-3-yl)-3,4-dihydro-2H-benzo[e][1,3]oxazine and pharmaceutically acceptable salts thereof.

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Finally, while an embodiment may be described as part of a series of steps or part of a more general structure, each said step may also be considered an independent embodiment in itself.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are described herein.

As employed above and throughout the disclosure, the following terms, unless otherwise indicated, shall be understood to have the following meanings.

The terms "*Plasmodium falciparum*" and "*P. falciparum*" are interchangeably used herein and refer to the parasite that is transmitted to human and animal hosts, resulting in the host showing one or more symptoms of malaria. More specifically, *P. falciparum* is a protozoan that causes malaria.

As used herein, "alkyl" includes a saturated, straight or branched hydrocarbon having from about 1 to about 20 carbon atoms (and all combinations and subcombinations of ranges and specific numbers of carbon atoms therein). The term "lower alkyl" herein refers to those alkyl groups having from about 1 to about 10 carbon atoms, these being preferred. Alkyl groups include, but are not limited to, methyl, ethyl, n-propyl, isopropyl, cyclopropyl, n-butyl, isobutyl, t-butyl, cyclobutyl, n-pentyl, cyclopentyl, isopentyl, neopentyl, n-hexyl, isohexyl, cyclohexyl, cycloheptyl, cyclooctyl, decahydronaphthalenyl, adamantyl, 3-methylpentyl, 2,2-dimethylbutyl, and 2,3-dimethylbutyl. Alkyl groups can be substituted or unsubstituted.

As used herein, "halogen" or "halo" includes fluoro, chloro, bromo, and iodo.

As used herein, "haloalkyl" includes an alkyl group substituted with one or more halo groups selected from —F or —Cl. An example of a haloalkyl group is —$CF_3$. Other examples are
—$CH_2$—$CH_2$—$CH_2$—$CF_3$ and —$CH_2$—CHF—$CH_3$.

As used herein, "alkoxy" includes an alkyl-O— moiety, wherein "alkyl" is defined as above.

As used herein, "haloalkoxy" includes an alkoxy group substituted with one or more halo groups selected from —F and —Cl. An example of a haloalkoxy group is —$OCF_3$. Other examples are —$CH_2$—$CH_2$—$CH_2$—$OCF_3$ and —$CH_2$—CH($OCF_3$)—$CH_3$.

As used herein, "cycloalkyl" includes an alkyl group having one or more rings in their structures, for example, cyclopropyl, cyclobutyl, cyclopentyl, and cyclohexyl. Multi-ring structures may be bridged or fused ring structures. The term "lower cycloalkyl" herein refers to those cycloalkyl groups having from about 3 to about 10 carbon atoms.

As used herein, "alk" refers to an alkylene moiety, for example, —$CH_2$—, $CH_2CH_2$—, and the like.

As used herein, "alkcycloalkyl" includes an alkylene moiety substituted by a cycloalkyl group. An example of an alkcycloalkyl group is —$CH_2$-cyclohexyl.

As used herein, "aryl" includes a mono-, di-, tri-, or other multicyclic aromatic ring system having from about 5 to about 30 carbon atoms (and all combinations and subcombinations of ranges and specific numbers of carbon atoms therein), with from about 6 to about 14 carbons being preferred. Non-limiting examples include phenyl, naphthyl, anthracenyl, and phenanthrenyl. Aryl groups can be substituted or unsubstituted.

As used herein, "heteroaryl" includes a mono-, di-, tri-, or other multicyclic aromatic ring system that includes at least one, and preferably from about 1 to about 4 heteroatom ring members, each heteroatom ring member independently being sulfur, oxygen, or nitrogen. Heteroaryl groups can have, for example, from about 3 to about 50 carbon atoms (and all combinations and subcombinations of ranges and specific numbers of carbon atoms therein), with from about 4 to about 10 carbons being preferred. Heteroaryl groups of $R^1$ within the scope of Formula I are attached to through a carbon atom, not a heteroatom. Non-limiting examples include, for example, monocyclic heteroaryl groups such as pyrrolyl, furyl, pyridyl, 1,2,4-thiadiazolyl, pyrimidyl, isothiazolyl, thiazolyl, triazolyl, imidazolyl, tetrazolyl, pyrazinyl, thienyl, pyrazolyl, oxazolyl, and isoxazolyl, and the fused bicyclic moieties formed by fusing one of these monocyclic groups with a phenyl ring or with any of the heteroaromatic monocyclic groups to form a bicyclic group such as indolyl, indazolyl, benzimidazolyl, benzotriazolyl, benzothienyl, benzofuryl, isobenzofuryl, benzothiazolyl, quinolyl, isoquinolyl, purinyl, pyrazolopyridyl, quinazolinyl, quinoxalinyl, and the like. Heteroaryl groups can be substituted or unsubstituted.

Typically, substituted chemical moieties include one or more substituents that replace hydrogen. Exemplary substituents include, for example, halo (e.g., —F, —Cl, —Br), (provided that when halo is —Br, the —Br is attached to an sp2 carbon such as on a carbon of an alkenyl or a ring carbon of aryl or heteroaryl group), alkoxy, haloalkoxy, —$OCF_3$, alkylthio, monohaloalkylthio, polyhaloalkylthio, —$SCF_3$, alkyl, —$CF_3$, haloalkyl, lower alkyl, spiroalkyl, alkenyl, alkynyl, aralkyl, aryl, heteroaryl, heterocyclyl, hydroxyl (—OH), nitro (—$NO_2$), cyano (—CN), sulfonyl (—$SO_2$R), sulfamoyl (—$SO_2NR^aR^b$), —$NR^aSO_2R^b$, —SR, amino (—$NH_2$, —NHR, —$NR^aR^b$), —$CO_2$R, —COR, —CH(OH)R, —C(OH)$R^aR^b$, —$CONR^aR^b$, —NHCOR, —$NR^aCOR^b$, and the like.

As used herein, "pharmaceutically acceptable" includes those compounds, materials, compositions, and/or dosage forms that are, within the scope of sound medical judgment, suitable for contact with the tissues of human beings and animals without excessive toxicity, irritation, allergic response, or other problem complications commensurate with a reasonable benefit/risk ratio.

As used herein, "pharmaceutically acceptable salts" includes derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. Thus, the term "acid addition salt" includes the corresponding salt derivative of a parent compound that has been prepared by the addition of an acid. The pharmaceutically acceptable salts include the conventional salts or the quaternary ammonium salts of the parent compound formed, for example, from inorganic or organic acids. For example, such conventional salts include, but are not limited to, those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

Certain acidic or basic compounds of the present invention may exist as zwitterions. All forms of the compounds, including free acid, free base, and zwitterions, are contemplated to be within the scope of the present invention.

All forms of the compounds, including free acid, free base, and zwitterions, isomorphic crystalline forms, all chiral and racemic forms, hydrates, solvates, and acid salt hydrates, are contemplated to be within the scope of the present invention.

"Patient" includes an animal, including a mammal, preferably a human.

It is believed the chemical formulas and names used herein correctly and accurately reflect the underlying chemical compounds. However, the nature and value of the present invention does not depend upon the theoretical correctness of these formulae, in whole or in part. Thus it is understood that the formulas used herein, as well as the chemical names attributed to the correspondingly indicated compounds, are not intended to limit the invention in any way, including restricting it to any specific tautomeric form or to any specific optical or geometric isomer.

When any variable occurs more than one time in any constituent or in any formula, its definition in each occurrence is independent of its definition at every other occurrence. Thus, for example, if an $R^1$ group is shown to be substituted with, for example, 1 to 5 of —CN, —OCF$_3$, haloalkoxy, —SCF$_3$, haloalkylthio, —SR$^4$, —NR$^5$R$^6$, —SO$_2$R$^4$, —SO$_2$NR$^5$R$^{6a}$, heteroaryl, or heterocyclyl, then the $R^1$ group may optionally be substituted with up to five of the above mentioned substituents, and the substituent at each occurrence is selected independently from the above defined list of possible substituents. Combinations of substituents and/or variables are permissible only if such combinations result in stable compounds. It is further understood that, while certain substituents are minimally required, such as, for example in the $R^1$ moiety, the moiety may be further substituted with the same substituent(s), another substituent(s) from the group of required substituents, or other substituent(s) not from the group of required substituents.

Compounds of the present invention may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

In certain embodiments, the invention is directed to compositions, each composition comprising at least one compound of Formula I or II or a pharmaceutically acceptable salt thereof; and at least one pharmaceutically acceptable carrier.

Such compositions are prepared in accordance with acceptable pharmaceutical procedures, such as described in *Remington's Pharmaceutical Sciences,* 17th edition, ed. Alfonoso R. Gennaro, Mack Publishing Company, Easton, Pa. (1985). Pharmaceutically acceptable carriers include those that are compatible with the other ingredients in the formulation and biologically acceptable.

The water solubility of the hydrochloride salts and most other salts of the parent compounds may be limited, so when aqueous solutions are prepared it may be preferable to add solubilizing agents to the water, such as non-aqueous solvents. Alternatively, a more soluble salt may be used or a very dilute solution prepared.

The compounds of this invention may be administered orally or parenterally, neat or in combination with conventional pharmaceutical carriers. Applicable solid carriers can include one or more substances that may also act as flavoring agents, lubricants, solubilizers, suspending agents, fillers, glidants, compression aids, binders or tablet-disintegrating agents or an encapsulating material. In powders, the carrier is a finely divided solid that is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Oral formulations are preferred and this invention has the advantage over related products of being readily absorbed by mammals at sufficient levels to make the compounds of the present invention orally active as therapeutic agents. Formulations for oral or injected use are based on sufficient solubility as to allow the therapeutic agent to enter solution in the stomach or in an injectable medium. Suitable drug formulations include, but are not limited to, tablets, pills, capsules, sachets, granules, powders, chewing gums, suspensions, emulsions, suppositories, and solutions. Preferred embodiments for oral use are tablets and capsules of all varieties. Preferred embodiments for injection or infusion are microbe-free solutions. Where appropriate and necessary the formulations may include diluents, binding agents, dispersing agents, surfaceactive agents, lubricating agents, coating materials, flavoring agents, coloring agents, controlled release formulations, sweeteners or any other pharmaceutically acceptable additives, for example, gelatin, sodium starch glycolate, lactose, starch, talc, magnesium stearate, microcrystalline cellulose, Povidone, hydrogenated or unsaturated oils, polyglycols, syrups or other aqueous solutions. Where the formulations are tablets or capsules and the like the formulations may be presented as premeasured unit doses or in multidose containers from which the appropriate unit dose may be withdrawn.

Liquid carriers may be used in preparing formulations including solutions, suspensions, emulsions, syrups, and elixirs. Compounds of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration. Liquid pharmaceutical compositions, which are sterile solutions or suspensions, can be administered by, for example, intramuscular, intraperitoneal or subcutaneous injection.

Sterile solutions can also be administered intravenously. Oral administration may be either liquid or solid composition form. The injectable form may be an aqueous or nonaqueous solution, suspension or emulsion in a pharmaceutically acceptable liquid, e.g. sterile pyrogen-free water or parenterally acceptable oils or mixture of liquids which may contain bacteriostatic agents, antioxidants or other preservatives and stabilizers, buffers (preferably but not limited to a physiological pH range of 6.5-7.7, solutes to render the solution isotonic with the blood, thickening agents, suspending agents or other pharmaceutically acceptable additives. Such forms will be presented in unit dose form such as ampules or disposable injection devices or in multi-dose forms such as a bottle from which the appropriate dose may be withdrawn, or as a solid form or concentrate that can be used to quickly prepare an injectable formulation. All formulations for injection are preferable as sterile and pyrogen free. Suppositories containing the compound will also contain suitable carriers, e.g. cocoa butter, polyglycols or other state-of-the-art carriers.

Preferably, compositions of the invention are in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

In addition to standard pharmaceutical additives there may be included within formulations of the invention other therapeutic agents, particularly including other antimalarial agents and antiinfective agents.

The compounds of the present invention may be prepared in a number of ways well known to those skilled in the art of which the following generally applicable multi-step processes are preferred. These multi-step processes typically utilize readily available starting materials. Intermediate products, if commercially available, may simplify or obviate some of the process steps. The compounds can be synthesized, for example, by the methods described below, or variations thereon as appreciated by the skilled artisan. All processes disclosed in association with the present invention are contemplated to be practiced on any scale, including milligram, gram, multigram, kilogram, multikilogram or commercial industrial scale.

As will be readily understood, functional groups present may contain protecting groups during the course of synthesis. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups can be employed with the present invention. Protecting groups that may be employed in accordance with the present invention may be described in Wuts, P. G. M. and Greene, T. W., Greene's Protective Groups in Organic Synthesis 4$^{th}$ Ed., Wiley & Sons, 2007.

Compounds of the invention can be prepared using well known synthetic techniques. One exemplary synthetic route to compounds of the invention is set forth below in Scheme 1.

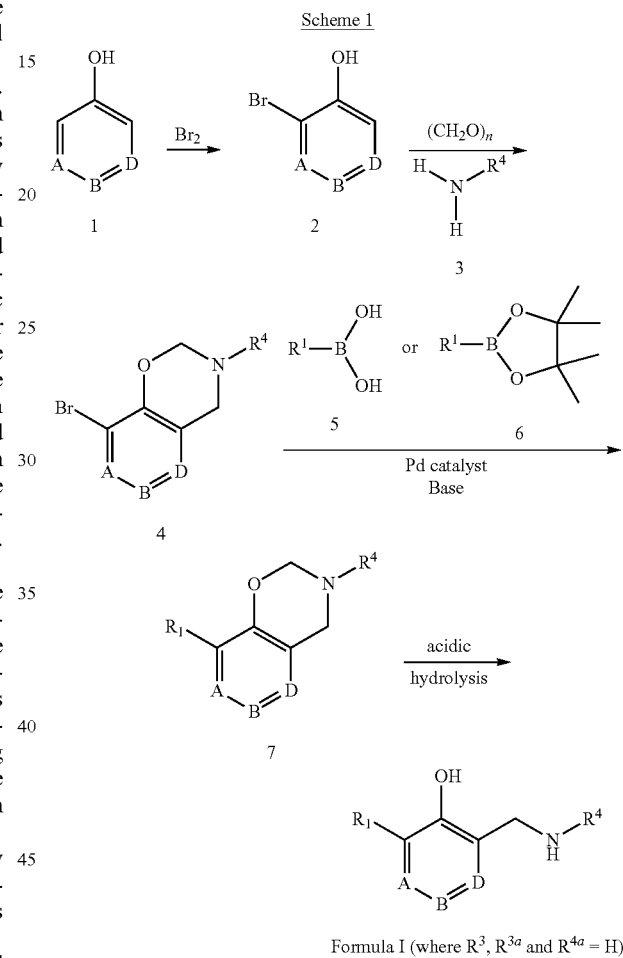

Selective ortho-bromination of a substituted phenol of general formula 1 gives the 2-bromophenol of general formula 2. Any conventional method for brominating a phenol can be utilized. In accordance with the preferred embodiment of this invention, a solution of phenol of general formula 1 in chlorinated solvent is treated with one equivalent of bromine at 0° C. to about 40° C. to give the 2-bromophenol of general formula 2. The next step involves a Mannich reaction of the 2-bromophenol of general formula 2 with excess paraformaldehyde and primary amine of general formula 3 to give the 8-bromo-3,4-dihydro-2H-benzo[e][1,3]oxazine of general formula 4. The reaction may be conducted at a variety of temperatures which depend on the chemical reactivity of the 2-bromophenol, and the imine formed from reaction of the primary amine 3 with paraformaldehyde. In accordance with the preferred embodiment of this invention, the 2-bromophenol of general formula 2 is treated with 5 equivalents of paraformaldehyde and 5 equivalents of primary amine of general formula 3 in isopropanol as solvent at about 80° C. The initially formed 2-aminomethylphenol reacts with additional imine to give the 8-bromo-3,4-dihydro-2H-benzo[e][1,3]oxazine of general formula 4. The next step involves a Suzuki reaction of the 8-bromo-3,4-dihydro-2H-benzo[e][1,3]oxazine of general formula 4 with either a heteroarylboronic acid of general formula 5 or heteroarylboronic ester of general formula 6 in the presence of a palladium catalyst and base in a suitable solvent to give the 8-heteroaryl-3,4-dihydro-2H-benzo[e][1,3]oxazine of general formula 7. A wide variety of catalyst systems can be utilized with the optimal catalyst, base and solvent dependant on the chemical composition of the bromide and boronic acid or ester coupling partners. Non-limiting examples of suitable palladium catalysts include tetrakis(triphenylphosphine)palladium (0), dichloro[1,1'-bis(diphenylphosphino)ferrocene]palladium (II) dichloromethane adduct, and trans-dichlorobis(triphenylphosphine)palladium (II). Potential bases include potassium carbonate, sodium carbonate, cesium carbonate, potassium acetate, potassium phosphate and triethylamine. A wide variety of solvents can be utilized including dimethoxyethane, tetrahydrofuran, dioxane, toluene and water. The reaction may be conducted at a variety of temperatures that range from ambient temperature to about 120° C. In accordance with the preferred embodiment of this invention, the 8-bromo-3,4-dihydro-2H-benzo[e][1,3]oxazine of general formula 4 is treated with one equivalent of heteroarylboronic acid of general formula 5 or heteroarylboronic ester of general formula 6 and 1.5 equivalents of potassium carbonate in the presence of catalytic (tetrakistriphenylphosphine)palladium (0) in a solvent mixture of dimethoxyethane and water at about 80° C. to give the 8-heteroaryl-3,4-dihydro-2H-benzo[e][1,3]oxazine of general formula 7. The final step in the synthesis of the compounds of Formula I is the hydrolysis of the 8-heteroaryl-3,4-dihydro-2H-benzo[e][1,3]oxazine intermediate of general formula 7 to give compounds of Formula I ($R^3$, $R^{3a}$, $R^{4a}$=H). The hydrolysis is generally conducted under acidic conditions in the presence of a mineral acid such as aqueous hydrochloric or sulfuric acid. A co-solvent such as an alcohol is usually added to the reaction mixture and the reaction is conducted at temperatures between ambient temperature and about 100° C. for periods of a few hours to a few days.

In some instances it may be advantageous to reverse the coupling partners in the Suzuki reaction and an alternative synthesis of the intermediate 8-heteroaryl-3,4-dihydro-2H-benzo[e][1,3]oxazine of general formula 7 is shown in Scheme 2.

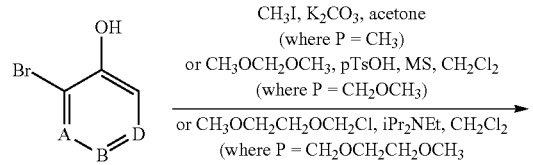

Scheme 2

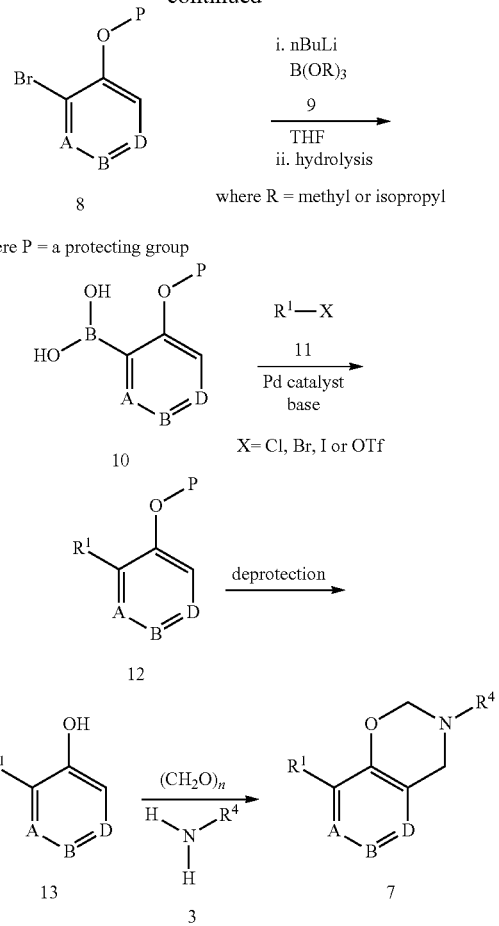

In order to allow for the use of an alkyl lithium in the synthetic route the 2-bromophenol of general formula 2 is protected. A large variety of phenol protecting groups that are stable in the presence of alkyl lithiums could be employed, for example those described in Wuts, P. G. M. and Greene, T. W., Greene's Protective Groups in Organic Synthesis 4$^{th}$ Ed., Wiley & Sons, 2007. In accordance with the preferred embodiment of this invention, the 2-bromophenol of general formula 2 is protected as a methyl ether, methoxymethyl ether (MOM ether) or methoxyethoxymethyl ether (MEM ether). Reaction conditions to achieve the desired phenol protection are described in Wuts, P. G. M. and Greene, T. W., Greene's Protective Groups in Organic Synthesis 4$^{th}$ Ed., Wiley & Sons, 2007. In accordance with the preferred embodiment of this invention, the methyl ether of general formula 8 (where P=$CH_3$) is prepared by treatment of the 2-bromophenol of general formula 2 with potassium carbonate and iodomethane or dimethylsulfate in acetone at temperatures ranging between ambient temperature and the reflux temperature of the solvent. Alternatively, to prepare the methoxymethyl ether of general formula 8 (where P=MOM), the 2-bromophenol of general formula 2 is treated with dimethoxymethane and para-toluenesulfonic acid in chlorinated solvent, in the presence of molecular sieves to absorb methanol, at temperatures ranging between ambient temperature and the reflux temperature of the solvent. To prepare the methoxyethoxymethyl ether of general formula 8 (where P=MEM), the 2-bromophenol of general formula 2 is treated 2-methoxyethoxymethyl chloride and diisopropylethylamine in a chlorinated solvent at temperatures ranging from about 0° C. to the reflux temperature of the solvent. The next step involves a halogen metal exchange reaction of the bromide of general formula 8 with an alkyl lithium to give an aryl lithium which is reacted directly with a trialkyl borate of general formula 9 to give a boronic acid of general formula 10 after aqueous hydrolysis. In accordance with the preferred embodiment of this invention, a solution bromide of general formula 8 and trimethyl or triisopropyl borate in tetrahydrofuran at −78° C. under inert atmosphere is treated with butyllithium solution in hexanes. The reaction is allowed to warm to about −10° C. then quenched with water to give the boronic acid of general formula 10. The next step involves a Suzuki reaction of the boronic acid of general formula 10 with a heteroaryl chloride, bromide, iodide or trifluoromethanesulfonate of general formula 11 (X=Cl, Br, I, or OTf) in the presence of a palladium catalyst and base in a suitable solvent to give a compound of general formula 12. A wide variety of catalyst systems can be utilized with the optimal catalyst, base and solvent dependant on the chemical composition of the boronic acid 10 and heteroaryl chloride, bromide, iodide or trifluoromethanesulfonate 11 coupling partners. Non-limiting examples of suitable palladium catalysts include tetrakis(triphenylphosphine)palladium (0), dichloro[1,1'-bis(diphenylphosphino)ferrocene]palladium(II) dichloromethane adduct, and trans-dichlorobis(triphenylphosphine)palladium (II). Potential bases include potassium carbonate, sodium carbonate, cesium carbonate, potassium acetate, potassium phosphate and triethylamine. A wide variety of solvents can be utilized including dimethoxyethane, tetrahydrofuran, dioxane, toluene and water. The reaction may be conducted at a variety of temperatures that range from ambient temperature to about 120° C. The next step involves removal of the preferred methyl, methoxymethyl (MOM) or methoxyethoxymethyl (MEM) protecting group. Reaction conditions to achieve the desired phenol deprotection are described in Wuts, P. G. M. and Greene, T. W., Greene's Protective Groups in Organic Synthesis 4$^{th}$ Ed., Wiley & Sons, 2007. In accordance with the preferred embodiment of this invention, a solution of the methyl ether of general formula 12 (where P=CH$_3$) in chlorinated solvent is treated with boron tribromide at temperatures ranging between 0° C. and the reflux temperature of the solvent for several hours to several days to give the 2-heteroarylphenol of general formula 13. To deprotect the MEM ether, a solution of the MEM ether of general formula 12 (where P=MEM) in methanol or ethanol and 1.0 M aqueous hydrochloric acid is stirred at temperatures ranging between 0° C. and the reflux temperature of the solvent for several hours to several days to give the 2-heteroarylphenol of general formula 13. The final step in the alternative synthesis of intermediate 8-heteroaryl-3,4-dihydro-2H-benzo[e][1,3]oxazine of general formula 7 involves a Mannich reaction of the 2-heteroarylphenol of general formula 13 with excess paraformaldehyde and primary amine of general formula 3. The reaction may be conducted at a variety of temperatures that depend on the chemical reactivity of the phenol 13, and the imine formed from reaction of the primary amine 3 with paraformaldehyde. In accordance with the preferred embodiment of this invention, the 2-heteroarylphenol of general formula 13 is treated with 5 equivalents of paraformaldehyde and 5 equivalents of primary amine in isopropanol as solvent at about 80° C. The initially formed 2-aminomethylphenol reacts with additional imine to give the 8-heteroaryl-3,4-dihydro-2H-benzo[e][1,3]oxazine of general formula 7.

An alternative synthesis of the 8-bromo-3,4-dihydro-2H-benzo[e][1,3]oxazine of general formula 4 (where A and D=CH, B=CR$^2$ and R$^2$=aryl or heteroaryl) is shown in Scheme 3.

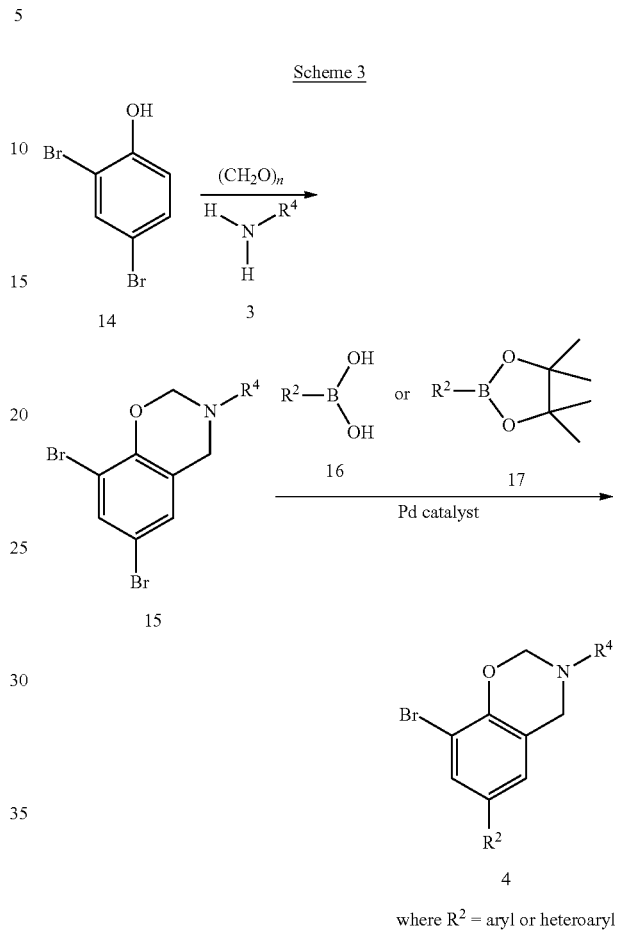

Mannich reaction of 2,4-dibromophenol 14 with excess paraformaldehyde and primary amine of general formula 3 gives a 6,8-dibromo-3,4-dihydro-2H-benzo[e][1,3]oxazine of general formula 15. The reaction may be conducted at a variety of temperatures which depend on the relative reactivity of the phenol 14, and the imine formed from reaction of the primary amine 3 with paraformaldehyde. In accordance with the preferred embodiment of this invention, 2,4-dibromophenol 14 is treated with 5 equivalents of paraformaldehyde and 5 equivalents of primary amine of general formula 3 in isopropanol as solvent at about 80° C. The initially formed 2-aminomethylphenol reacts with additional imine to give the 6,8-dibromo-3,4-dihydro-2H-benzo[e][1,3]oxazine of general formula 15. The next step involves a preferential Suzuki reaction of the more reactive 6-bromide of the 6,8-dibromo-3,4-dihydro-2H-benzo[e][1,3]oxazine of general formula 15 with either a heteroaryl or arylboronic acid of general formula 16 or heteroaryl or arylboronic ester of general formula 17 in the presence of a palladium catalyst and base in a suitable solvent to give the 8-bromo-3,4-dihydro-2H-benzo[e][1,3]oxazine of general formula 4. A wide variety of catalyst systems can be utilized with the optimal catalyst, base and solvent dependant on the chemical composition of the bromide and boronic acid or ester coupling partners. Suitable palladium catalysts include, but are not limited to, tetrakis(triphenylphosphine)palladium (0), dichloro[1,1'-bis(diphenylphosphino)ferrocene]palladium(II) dichloromethane adduct, and trans-dichlorobis(triphenylphosphine)palladium (II). Potential bases include potassium carbonate, sodium carbonate, cesium carbonate, potassium acetate, potassium phosphate and triethylamine A wide variety of solvents can be utilized including dimethoxyethane, tetrahydrofuran, dioxane, toluene, 2-propanol and water. The reaction may be conducted at a variety of temperatures that range from ambient temperature to about 120° C. In accordance with the preferred embodiment of this invention, the 6,8-dibromo-3,4-dihydro-2H-benzo[e][1,3]oxazine of general formula 15 is treated 1.05 equivalents of heteroaryl or arylboronic acid of general formula 16 or heteroaryl or arylboronic ester of general formula 17 and 1.5 equivalents of potassium carbonate in the presence of catalytic (tetrakistriphenylphosphine)palladium (0) in a solvent mixture of 2-propanol and water at about 70° C. to give the 8-bromo-3,4-dihydro-2H-benzo[e][1,3] oxazine of general formula 4 (where $R^2$=aryl or heteroaryl).

An alternative synthesis of 8-heteroaryl-3,4-dihydro-2H-benzo[e][1,3]oxazine of general formula 7 (where A and D=CH, B=$CR^2$ and $R^1$ and $R^2$ are the same heteroaryl) is shown in Scheme 4.

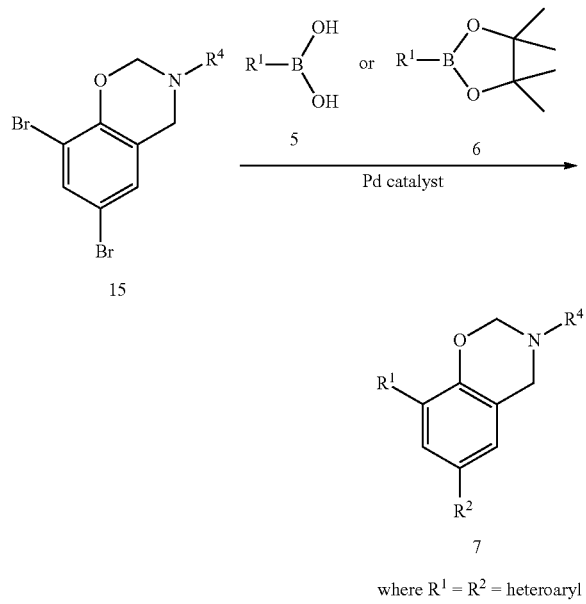

Suzuki reaction of 6,8-dibromo-3,4-dihydro-2H-benzo[e][1,3]oxazine of general formula 15 with excess of either a heteroarylboronic acid of general formula 5 or heteroarylboronic ester of general formula 6 in the presence of a palladium catalyst and base in a suitable solvent gives the 8-heteroaryl-3,4-dihydro-2H-benzo[e][1,3]oxazine of general formula 7 (where $R^1$ and $R^2$ are the same heteroaryl). A wide variety of catalyst systems can be utilized with the optimal catalyst, base and solvent dependant on the chemical composition of the bromide and boronic acid or ester coupling partners. Non-limiting examples of suitable palladium catalysts include tetrakis(triphenylphosphine)palladium (0), dichloro [1,1'-bis(diphenylphosphino)ferrocene]palladium(II) dichloromethane adduct, and trans-dichlorobis(triphenylphosphine)palladium (II). Potential bases include potassium carbonate, sodium carbonate, cesium carbonate, potassium acetate, potassium phosphate and triethylamine A wide variety of solvents can be utilized including dimethoxyethane, tetrahydrofuran, dioxane, toluene, 2-propanol and water. The reaction may be conducted at a variety of temperatures that range from ambient temperature to about 120° C. In accordance with the preferred embodiment of this invention, the 6,8-dibromo-3,4-dihydro-2H-benzo[e][1,3]oxazine of general formula 15 is treated three equivalents of heteroarylboronic acid of general formula 16 or heteroarylboronic ester of general formula 17 and eight equivalents of potassium carbonate in the presence of catalytic (tetrakistriphenylphosphine)palladium (0) in a solvent mixture of 2-propanol and water at around 70° C. to give the 8-heteroaryl-3,4-dihydro-2H-benzo[e][1,3]oxazine of general formula 7 (where $R^1$ and $R^2$ are the same heteroaryl).

Another exemplary synthesis of the compounds of Formula I ($R^3$, $R^{3a}$=H) is shown in Scheme 5.

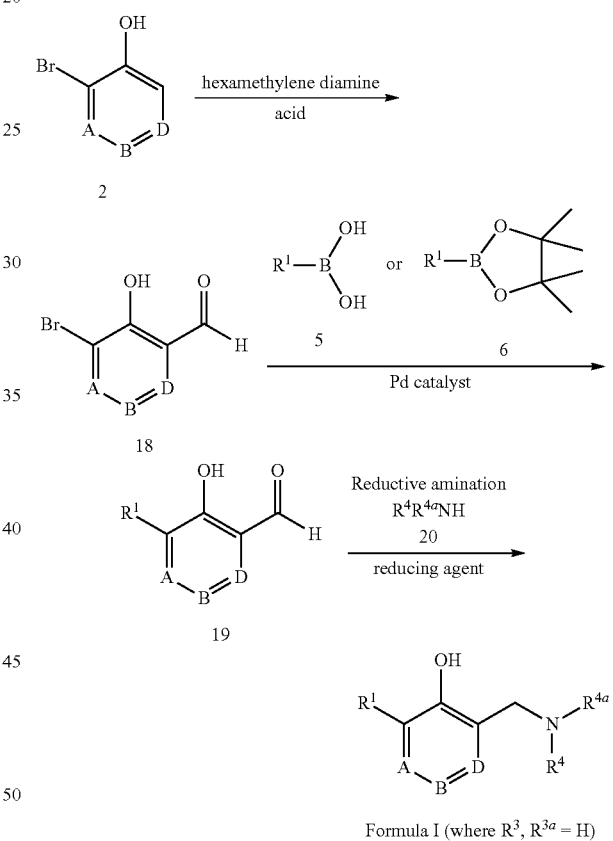

Ortho-formylation of a 2-bromophenol of general formula 2 gives the 3-bromo-2-hydroxybenzaldehyde of general formula 18. A number of reactions are available to accomplish this transformation including the Reimer-Tiemann reaction of a phenol with chloroform in the presence of a strong base (for a review see Wynberg, H. and Meijer, E. W. *Org. React.* 1982, 28, 2) or Duff reaction of a phenol with hexamethylenetetramine in the presence of acid. In accordance with the preferred embodiment of this invention, a solution of 2-bromophenol of general formula 2 and excess hexamethylenetetratramine in trifluoroacetic acid is refluxed under an inert atmosphere for a period of several hours to several days to give the 3-bromo-2-hydroxybenzaldehyde of general formula 18. The next step involves a Suzuki reaction of the 3-bromo-2-hydroxybenzaldehyde of general formula 18 with either a heteroarylboronic acid of general formula 5 or heteroarylboronic ester of general formula 6 in the presence of a palladium catalyst and base in a suitable solvent to give the 3-heteroaryl-2-hydroxybenzaldehyde of general formula 19. A wide variety of catalyst systems can be utilized with the optimal catalyst, base and solvent dependant on the chemical composition of the bromide and boronic acid or ester coupling partners. Non-limiting examples of suitable palladium catalysts include tetrakis(triphenylphosphine)palladium (0), dichloro[1,1'-bis(diphenylphosphino)ferrocene]palladium (II) dichloromethane adduct, and trans-dichlorobis(triphenylphosphine)palladium (II). Potential bases include potassium carbonate, sodium carbonate, cesium carbonate, potassium acetate, potassium phosphate and triethylamine A wide variety of solvents can be utilized including dimethoxyethane, tetrahydrofuran, dioxane, toluene, 2-propanol and water. The reaction may be conducted at a variety of temperatures that range from ambient temperature to about 120° C. In accordance with the preferred embodiment of this invention, the 3-bromo-2-hydroxybenzaldehyde of general formula 18 is treated with 1.1 equivalents of heteroarylboronic acid of general formula 5 or heteroarylboronic ester of general formula 6 and 2.5 equivalents of potassium carbonate in the presence of catalytic (tetrakistriphenylphosphine)palladium (0) in a solvent mixture of dimethoxyethane and water at about 80° C. to give the 3-heteroaryl-2-hydroxybenzaldehyde of general formula 19. Reductive amination of the 3-heteroaryl-2-hydroxybenzaldehyde of general formula 19 with an amine of general formula 20 in the presence of a reducing agent in a suitable solvent such as methanol, ethanol, tetrahydrofuran or dichloroethane gives the compounds of Formula I ($R^3$, $R^{3a}$=H). Examples of reducing agents include hydrogen in the presence of a hydrogenation catalyst, for example palladium or platinum on carbon, sodium cyanoborohydride (for a review see Lane, C. F., *Synthesis* 1975, 135) or sodium triacetoxyborohydride (Abdel-Magid, A. F. et al. *J. Org. Chem.* 1996, 61, 3849). Alternatively, when the amine of general formula 20 is a primary amine the intermediate imine can be preformed then reduced in situ with sodium borohydride (Abdel-Magid, A. F. et al. *J. Org. Chem.* 1996, 61, 3849). In accordance with the preferred embodiment of this invention, the 3-heteroaryl-2-hydroxybenzaldehyde of general formula 19 is treated with 1 to 4 equivalents of an amine of general formula 20, 1 to 3 equivalents of sodium triacetoxyborohydride and 0 to 2 equivalents of acetic acid in dichloroethane to give the compounds of Formula I ($R^3$, $R^{3a}$=H). When the amine of general formula 20 is a primary amine, a solution of 3-heteroaryl-2-hydroxybenzaldehyde of general formula 19 in methanol is treated with an amount in the range of about 1 to about 4 equivalents of primary amine of general formula 20 for a period of time in the range of a few hours to a few days to preform the intermediate imine. Addition of sodium borohydride then gives the compounds of Formula I ($R^3$, $R^{3a}$=H).

In some instances it may be advantageous to reverse the couplings partners in the Suzuki reaction and an alternative synthesis of the 3-heteroaryl-2-hydroxybenzaldehyde of general formula 19 is shown in Scheme 6.

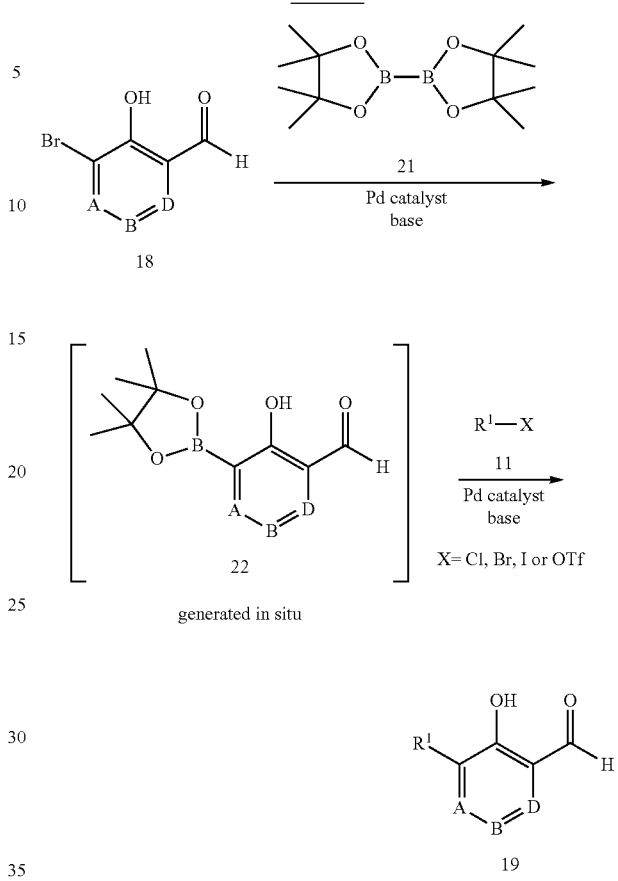

Scheme 6

The Miyaura borylation reaction (Ishiyama, T. et al., *J. Org. Chem.* 1995, 60, 7508) of the 3-bromo-2-hydroxybenzaldehyde of general formula 18 with bis(pincaloto)diboron 21 in the presence of a suitable palladium catalyst such as [1,1'-bis(diphenylphosphino)ferrocene]dichloropalladium (II) complex with dichloromethane, base such as potassium acetate and solvent such as dioxane or dimethylsulfoxide gives the boronic ester of general formula 22. The boronic ester can be isolated or reacted directly in the subsequent Suzuki reaction (Ishiyama, T. et al., *Tetr. Lett.* 1997, 38, 7508). Suzuki reaction of the boronic ester of general formula 22 with a heteroaryl chloride, bromide, iodide or trifluoromethanesulfonate of general formula 11 (X=Cl, Br, I, or OTf) in the presence of a palladium catalyst and base in a suitable solvent gives the 3-heteroaryl-2-hydroxybenzaldehyde of general formula 19. Non-limiting examples of suitable palladium catalysts include tetrakis(triphenylphosphine)palladium (0), dichloro[1,1'-bis(diphenylphosphino)ferrocene]palladium(II) dichloromethane adduct, and trans-dichlorobis(triphenylphosphine)palladium (II). Potential bases include potassium carbonate, sodium carbonate, cesium carbonate, potassium acetate, potassium phosphate and triethylamine A wide variety of solvents can be utilized including dimethoxyethane, tetrahydrofuran, dioxane, toluene, 2-propanol and water.

An alternative synthesis of protected 2-heteroarylphenols of general formula 12 is shown in Scheme 7.

Scheme 7

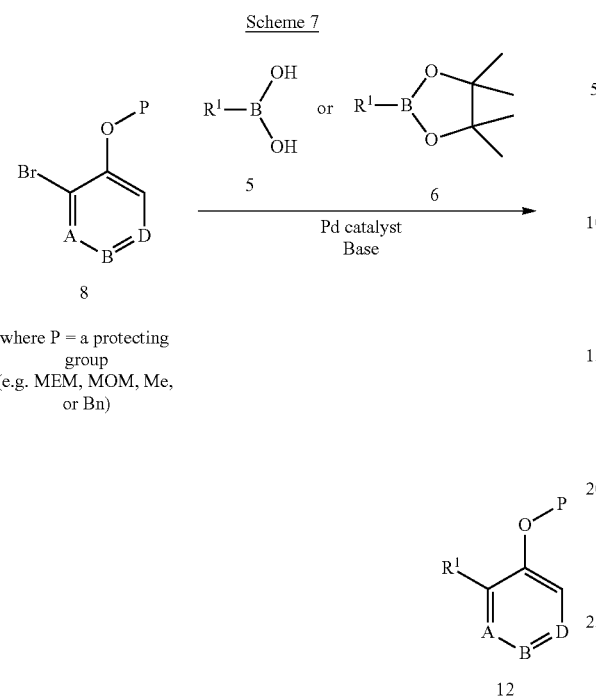

where P = a protecting group
(e.g. MEM, MOM, Me, or Bn)

Scheme 8

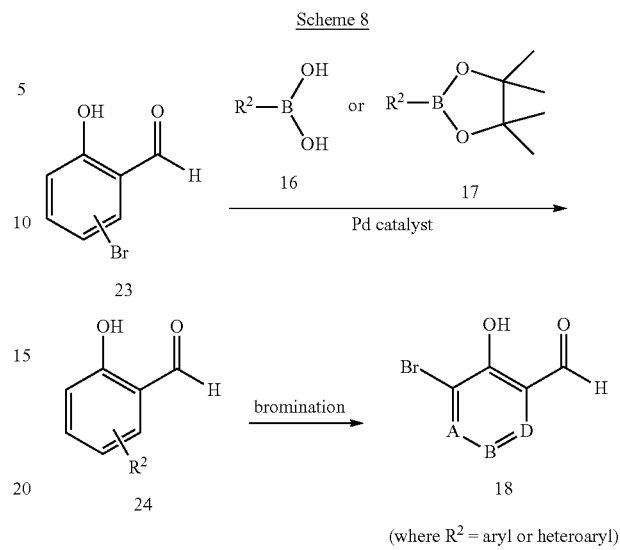

(where $R^2$ = aryl or heteroaryl)

A Suzuki reaction of a protected 2-bromophenol of general formula 8 with either a heteroarylboronic acid of general formula 5 or heteroarylboronic ester of general formula 6 in the presence of a palladium catalyst and base in a suitable solvent gives the protected 2-heteroarylphenols of general formula 12. A wide variety of catalyst systems can be utilized with the optimal catalyst, base and solvent dependant on the chemical composition of the bromide and boronic acid or ester coupling partners. Non-limiting examples of suitable palladium catalysts include tetrakis(triphenylphosphine)palladium (0), dichloro[1,1'-bis(diphenylphosphino)ferrocene]palladium(II) dichloromethane adduct, and trans-dichlorobis(triphenylphosphine)palladium (II). Potential bases include potassium carbonate, sodium carbonate, cesium carbonate, potassium acetate, potassium phosphate and triethylamine A wide variety of solvents can be utilized including dimethoxyethane, tetrahydrofuran, dioxane, toluene and water. The reaction may be conducted at a variety of temperatures that range from ambient temperature to about 120° C. In accordance with the preferred embodiment of this invention, the protected 2-bromophenol of general formula 8 is treated with 1.3 equivalents of heteroarylboronic acid of general formula 5 or heteroarylboronic ester of general formula 6 and 1.5 equivalents of potassium carbonate in the presence of catalytic (tetrakistriphenylphosphine)palladium (0) in a solvent mixture of dimethoxyethane and water at about 80° C. to give the of protected 2-heteroarylphenols of general formula 12.

An alternative synthesis of 3-bromo-2-hydroxybenzaldehydes of general formula 18 ($R^2$=aryl or heteroaryl) is shown in Scheme 8.

Suzuki reaction of a bromo-2-hydroxybenzaldehyde of general formula 23 with either an aryl or heteroarylboronic acid of general formula 16 or aryl or heteroarylboronic ester of general formula 17 in the presence of a palladium catalyst and base in a suitable solvent gives an aryl or heteroaryl-2-hydroxybenzaldehyde of general formula 24. A wide variety of catalyst systems can be utilized with the optimal catalyst, base and solvent dependant on the chemical composition of the bromide and boronic acid or ester coupling partners. Non-limiting examples of suitable palladium catalysts include tetrakis(triphenylphosphine)palladium (0), dichloro[1,1'-bis(diphenylphosphino)ferrocene]palladium(II) dichloromethane adduct, and trans-dichlorobis(triphenylphosphine)palladium (II). Potential bases include potassium carbonate, sodium carbonate, cesium carbonate, potassium acetate, potassium phosphate and triethylamine A wide variety of solvents can be utilized including dimethoxyethane, tetrahydrofuran, dioxane, toluene, 2-propanol and water. The reaction may be conducted at a variety of temperatures that range from ambient temperature to about 120° C. In accordance with the preferred embodiment of this invention, the bromo-2-hydroxybenzaldehyde of general formula 23 is treated with one equivalent of aryl or heteroarylboronic acid of general formula 16 or aryl or heteroarylboronic ester of general formula 17 and 2.5 equivalents of potassium carbonate in the presence of catalytic (tetrakistriphenylphosphine)palladium (0) in a solvent mixture of dimethoxyethane and water at about 80° C. to give the aryl or heteroaryl-2-hydroxybenzaldehyde of general formula 24. Selective ortho-bromination of the aryl or heteroaryl-2-hydroxybenzaldehyde of general formula 24 gives the 3-bromo-2-hydroxybenzaldehyde of general formula 18. Any conventional method for brominating a phenol can be utilized. In accordance with the preferred embodiment of this invention, a solution of phenol of general formula 24 and sodium acetate in acetic acid and optionally a chlorinated co-solvent is treated with one equivalent of bromine at 0° C. to about 40° C. to give the 3-bromo-2-hydroxybenzaldehyde of general formula 18 ($R^2$=aryl or heteroaryl).

An alternative synthesis of the compounds of Formula I ($R^3$ and $R^{3a}$=H, $R^{4a}$=$CH_2R$) is shown in Scheme 9.

Scheme 9

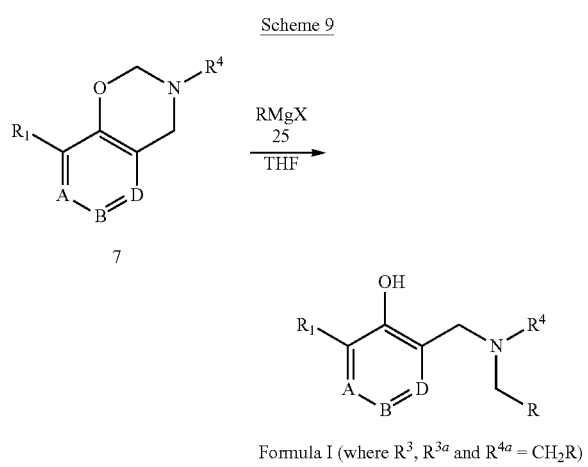

Addition of a Grignard reagent of general formula RMgX 25 (R=alkyl, cylcoalkyl or haloalkyl) to a 8-heteroaryl-3,4-dihydro-2H-benzo[e][1,3]oxazine of general formula 7 gives a compound of general Formula I. Reaction conditions to achieve the desired transformation have been described by Cimarelli (Cimarelli, C. et al.; *Tetrahedron*, 2001, 57(28), 6089). In accordance with the preferred embodiment of this invention, a slight excess of a solution of Grignard reagent of general formula 25 is added to a solution of 8-heteroaryl-3,4-dihydro-2H-benzo[e][1,3]oxazine of general formula 7 in tetrahydrofuran or diethyl ether at 0° C. to about 40° C. to give compounds of general Formula I ($R^3$ and $R^{3a}$=H, $R^{4a}$=CH$_2$R).

A synthesis of primary amines of Formula I ($R^3$, $R^{3a}$, $R^4$ and $R^{4a}$=H) is shown in Scheme 10.

Scheme 10

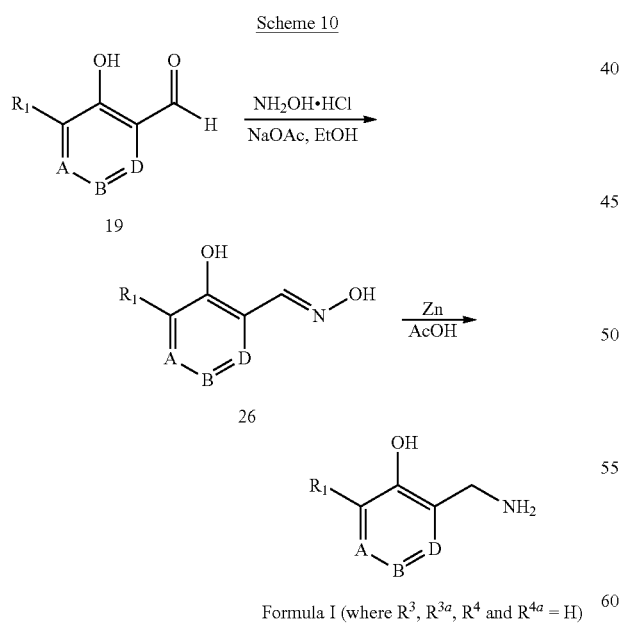

Addition of hydroxylamine to a 3-heteroaryl-2-hydroxybenzaldehyde of general formula 19 gives an oxime of general formula 26. Reduction of the oxime then gives a primary amine of general Formula I ($R^3$, $R^{3a}$, $R^4$ and $R^{4a}$=H). A number of reducing reagents can be utilized to reduce the oxime including lithium aluminium hydride, zinc in acetic acid and borane. In accordance with the preferred embodiment of this invention, a slight excess of hydroxylamine is added to a solution of 3-heteroaryl-2-hydroxybenzaldehyde of general formula 19 and sodium acetate in ethanol at 0° C. to about 40° C. to give the oxime of general formula 26. Addition of zinc, nine equivalents, to a solution of the oxime of general formula 26 in acetic acid at a temperature ranging from 40° C. to about 100° C. then gives the compound of general Formula I ($R^3$, $R^{3a}$, $R^4$ and $R^{4a}$=H).

A synthesis of the compounds of general Formula I ($R^{3a}$=H) is shown in Scheme 11.

Scheme 11

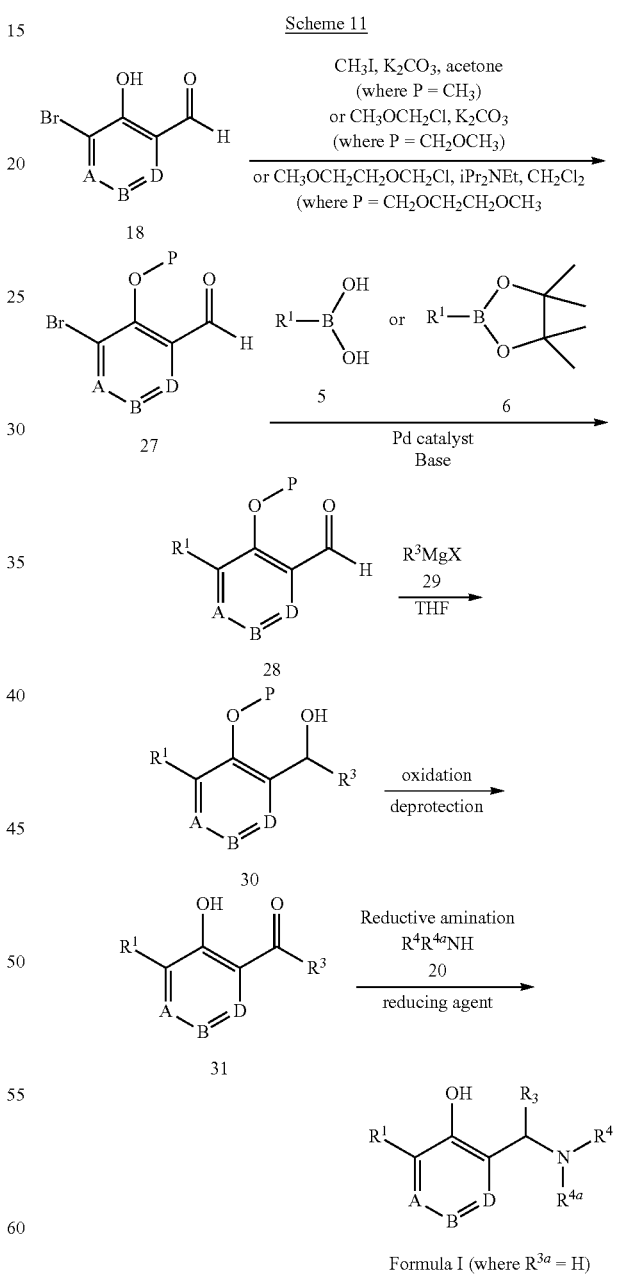

In order to improve the aryl-aryl coupling yield and to allow for both a Grignard addition and subsequent oxidation, the 3-bromo-2-hydroxybenzaldehyde of general formula 18 is protected. A large variety of phenol protecting groups that are stable in the presence of Grignard reagents could be employed, for example those described in Wuts, P. G. M. and Greene, T. W., Greene's Protective Groups in Organic Synthesis 4th Ed., Wiley & Sons, 2007. In accordance with the preferred embodiment of this invention, the 3-bromo-2-hydroxybenzaldehyde of general formula 18 is protected as either a methyl ether, methoxymethyl ether (MOM ether) or methoxyethoxymethyl ether (MEM ether). Reaction conditions to achieve the desired phenol protection are described in Wuts, P. G. M. and Greene, T. W., Greene's Protective Groups in Organic Synthesis 4th Ed., Wiley & Sons, 2007. In accordance with the preferred embodiment of this invention, the methyl ether of general formula 27 (where P=CH$_3$) is prepared by treatment of the 3-bromo-2-hydroxybenzaldehyde of general formula 18 with potassium carbonate and iodomethane or dimethylsulfate in acetone at temperatures ranging between ambient temperature and the reflux temperature of the solvent. Alternatively, to prepare the methoxymethyl ether of general formula 27 (where P=MOM), the 3-bromo-2-hydroxybenzaldehyde of general formula 18 is treated with chloromethyl methyl ether (MOM-chloride) and potassium carbonate in a polar aprotic solvent at temperatures ranging between ambient temperature and the reflux temperature of the solvent. To prepare the methoxyethoxymethyl ether of general formula 27 (where P=MEM), the 3-bromo-2-hydroxybenzaldehyde of general formula 18 is treated with diisopropylethylamine and 2-methoxyethoxymethyl chloride in halogenated solvents at temperatures ranging from 0° C. to the reflux temperature of the solvent. The next step involves a Suzuki reaction of the protected 3-bromo-2-hydroxybenzaldehyde of general formula 27 with either a heteroarylboronic acid of general formula 5 or heteroarylboronic ester of general formula 6 in the presence of a palladium catalyst and base in a suitable solvent to give the protected 3-heteroaryl-2-hydroxybenzaldehyde of general formula 28. A wide variety of catalyst systems can be utilized with the optimal catalyst, base and solvent dependant on the chemical composition of the bromide and boronic acid or ester coupling partners. Non-limiting examples of suitable palladium catalysts include tetrakis(triphenylphosphine)palladium (0), dichloro[1,1'-bis(diphenylphosphino)ferrocene]palladium(II) dichloromethane adduct, and trans-dichlorobis(triphenylphosphine)palladium (II). Potential bases include potassium carbonate, sodium carbonate, cesium carbonate, potassium acetate, potassium phosphate and triethylamine A wide variety of solvents can be utilized including dimethoxyethane, tetrahydrofuran, dioxane, toluene and water. The reaction may be conducted at a variety of temperatures that range from ambient temperature to about 120° C. In accordance with the preferred embodiment of this invention, the protected 3-bromo-2-hydroxybenzaldehyde of general formula 27 is treated with one equivalent of heteroarylboronic acid of general formula 5 or heteroarylboronic ester of general formula 6 and 1.5 equivalents of potassium carbonate in the presence of catalytic (tetrakistriphenylphosphine)palladium (0) in a solvent mixture of dimethoxyethane and water at around 80° C. to give the protected 3-heteroaryl-2-hydroxybenzaldehyde of general formula 28. Introduction of the benzyl substituent is accomplished by addition of a Grignard reagent, R$^3$MgX 29 (R$^3$=alkyl, cylcoalkyl or haloalkyl), at −78° C. in tetrahydrofuran to give an alcohol of general formula 30. In accordance with the preferred embodiment of this invention, the benzylic alcohol of general formula 30 is oxidized to the ketone of general formula 31 using the Dess Martin periodinane and sodium bicarbonate in methylene chloride. The next step involves removal of the preferred methyl, methoxymethyl (MOM) or methoxyethoxymethyl (MEM) protecting group.

Reaction conditions to achieve the desired phenol deprotection are described in Wuts, P. G. M. and Greene, T. W., Greene's Protective Groups in Organic Synthesis 4th Ed., Wiley & Sons, 2007. Reductive amination of the ketone of general formula 31 with an amine of general formula 20 in the presence of a reducing agent in a suitable solvent such as methanol, ethanol, tetrahydrofuran of dichloroethane gives compounds of Formula I (R$^{3a}$=H). Examples of reducing agents include hydrogen in the presence of a hydrogenation catalyst, for example palladium or platinum on carbon, sodium cyanoborohydride (for a review see Lane, C. F., *Synthesis* 1975, 135) or sodium triacetoxyborohydride (Abdel-Magid, A. F. et al. *J. Org. Chem.* 1996, 61, 3849). Alternatively, when the amine of general formula 20 is a primary amine the intermediate imine can be preformed then reduced in situ with sodium borohydride (Abdel-Magid, A. F. et al. *J. Org. Chem.* 1996, 61, 3849). In accordance with the preferred embodiment of this invention, a solution of ketone of general formula 31 in excess primary amine of general formula 20 is stirred at a temperature ranging from 40° C. to about 100° C. for a period of a few hours to a few days to form the intermediate imine. The imine is then reduced by the addition of excess sodium borohydride to give the compounds of Formula I (R$^{3a}$=H).

An exemplary synthesis of pyridyl compounds of Formula I (A=N, R$^3$, R$^{3a}$, R$^{4a}$=H) is shown in Scheme 12.

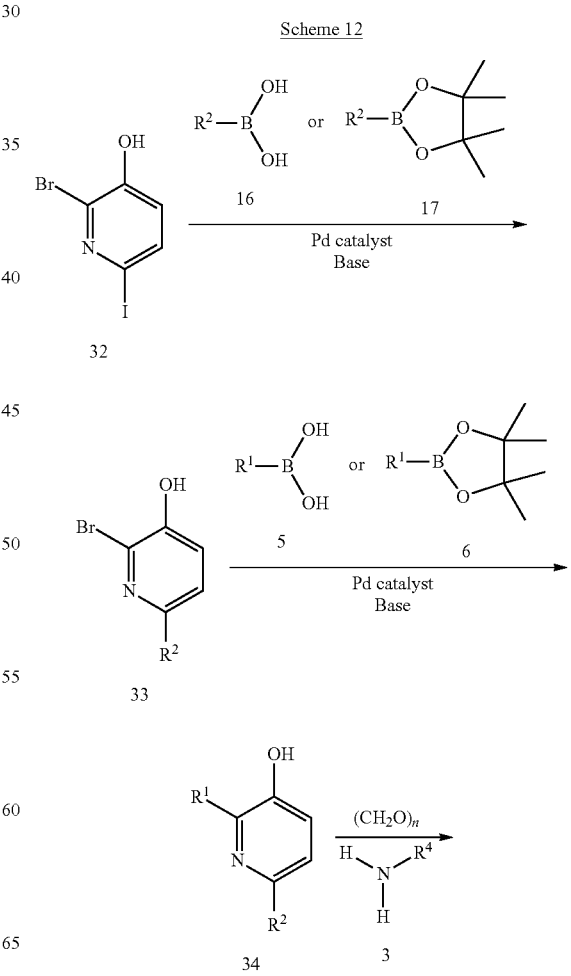

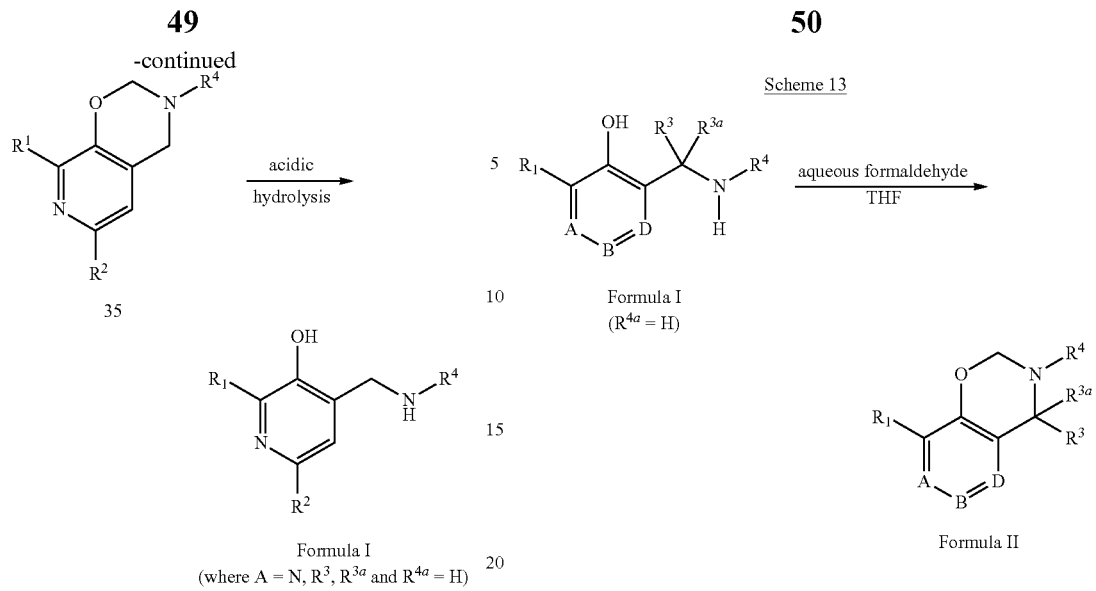

Scheme 13

Formula I
($R^{4a}$ = H)

Formula II

A preferential Suzuki reaction of the more reactive 6-iodo group of 2-bromo-6-iodopyridin-3-ol 32 with either a heteroaryl or arylboronic acid of general formula 16 or heteroaryl or arylboronic ester of general formula 17 in the presence of a palladium catalyst and base in a suitable solvent gives the 2-bromo-pyridin-3-ol of general formula 33. Non-limiting examples of suitable palladium catalysts include tetrakis(triphenylphosphine)palladium (0), dichloro[1,1'-bis (diphenylphosphino)ferrocene]palladium(II) dichloromethane adduct, and trans-dichlorobis(triphenylphosphine)palladium (II). Potential bases include potassium carbonate, sodium carbonate, cesium carbonate, potassium acetate, potassium phosphate and triethylamine A wide variety of solvents can be utilized including dimethoxyethane, tetrahydrofuran, dioxane, toluene and water. The reaction may be conducted at a variety of temperatures that range from ambient temperature to about 120° C. A second Suzuki reaction then occurs at the bromide of 2-bromo-pyridin-3-ol of general formula 33 with a heteroarylboronic acid of general formula 5 or heteroarylboronic ester of general formula 6 in the presence of a palladium catalyst and base in a suitable solvent to give the 2-heteroaryl-pyridin-3-ol of general formula 34. Non-limiting examples of suitable palladium catalysts include tetrakis(triphenylphosphine)palladium (0), dichloro[1,1'-bis(diphenylphosphino)ferrocene] palladium(II) dichloromethane adduct, and trans-dichlorobis (triphenylphosphine)palladium (II). Potential bases include potassium carbonate, sodium carbonate, cesium carbonate, potassium acetate, potassium phosphate and triethylamine A wide variety of solvents can be utilized including dimethoxyethane, tetrahydrofuran, dioxane, toluene and water. The reaction may be conducted at a variety of temperatures that range from ambient temperature to about 120° C. A Mannich reaction of the 2-heteroaryl-pyridin-3-ol of general formula 34 with excess paraformaldehyde and primary amine of general formula 3 followed by hydrolysis of the intermediate 3,4-dihydro-2H-pyrido[4,3-e][1,3]oxazine 35 then gives the pyridyl compounds of Formula I (A=N, $R^3$, $R^{3a}$, $R^{4a}$=H).

A synthesis of 3,4-dihydro-2H-benzo[e][1,3]oxazines of Formula II is shown in Scheme 13.

A solution of a compound of Formula I ($R^{4a}$=H) in a water miscible solvent, such as tetrahydrofuran, is treated with a slight excess of 37% aqueous formaldehyde solution and the mixture stirred at a temperature ranging from 0° C. to the reflux temperature of the solvent for a period of a few hours to a few days to give a compound of Formula II (Cimarelli, C. et al., *Tetrahedron* 2001, 57, 6089).

Another aspect of the invention includes methods for the treatment of malaria. In some embodiments methods for the treatment of malaria comprise administering to a patient in need of such treatment a compound of Formula I or II. Such treatment may also comprise administration of a pharmaceutical composition comprising a compound of Formula I or II.

In some embodiments methods for treatment of malaria comprise coadministration of one or more anti-malarial agents with a compound of Formula I or II. Anti-malarial agents suitable for co-administration with a compound of Formula I or II include, for example, Amodiaquine, Arteether, Arteflene, Artemether, Artemisinin, Artesunate, Atovaquone, Chloroquine, Clindamycin, Dihydroartemisinin, Doxycycline, Halofantrine, Lumefantrine, Mefloquine, Pamaquine, Piperaquine, Primaquine, Proguanil, Pyrimethamine, Pyronaridine, Quinine, and Tafenoquine, and combinations thereof.

EXAMPLES

The following examples are illustrative of how to prepare exemplary compounds of the invention. These examples are merely illustrative and should not be construed as limiting the scope of the invention. All substituents are as defined above unless indicated otherwise.

General Procedures

The HPLC/MS analyses were performed using a Hewlett Packard 1100 mass spectrometer coupled to a Hewlett Packard 1100 series HPLC utilizing a Phenomenex Kinetex XB-C18 50×4.60 mm column eluting a 1 mL/min with a solvent gradient of 70:30 A:B for 1.0 min, then 70:30 to 10:90 A:B over 6.5 min, then 10:90 A:B for 2.0 min, then 10:90 to 70:30 A:B over 0.5 min: solvent A=0.05% formic acid in water, solvent B=acetonitrile.

Proton NMR spectra were obtained with a 400 MHz Varian Unity Inova Spectrometer in chloroform-d, methanol-$d_4$ or dimethyl sulfoxide-$d_6$ and chemical shifts are reported as δ using the deuterium solvent as a standard and coupling constants are reported in hertz.

Intermediate 1

8-Bromo-3,6-di-tert-butyl-3,4-dihydro-2H-benzo[e][1,3]oxazine

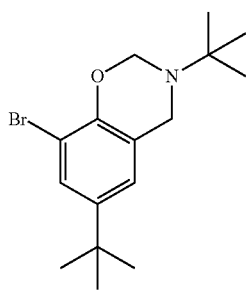 [SMILES: CC(C)(C)c1cc(Br)c2c(c1)CN(C(C)(C)C)CO2]

Step 1: 2-Bromo-4-(tert-butyl)phenol

A solution of bromine (7.18 mL, 0.14 mol) in chloroform (25 mL) was added dropwise over 2 hours to a solution of 4-tert-butyl-phenol (20 g, 0.133 mol) in 1:1 v/v chloroform:carbon tetrachloride (64 mL) at 0° C. under nitrogen until a slight red coloration persisted (approximately 1 mL of bromine solution remained). The reaction mixture was then purged with nitrogen overnight. The resulting tan solution was diluted with dichloromethane (50 mL), washed with 1% aqueous sodium thiosulfate solution (100 mL) and saturated brine (100 mL), dried (MgSO$_4$), filtered and concentrated under reduced pressure to give 2-bromo-4-(tert-butyl)phenol (30.5 g, quantitative yield) as a colorless oil.

Step 2: 8-Bromo-3,6-di-tert-butyl-3,4-dihydro-2H-benzo[e][1,3]oxazine

A mixture of paraformaldehyde (19.99 g, 0.666 mol) and tert-butylamine (70.26 mL, 0.666 mol) in isopropanol (260 mL) was heated to gentle reflux under nitrogen for 75 minutes. A solution of 2-bromo-4-(tert-butyl)phenol (30.5 g, 0.133 mol) in isopropanol (40 mL) was then added and the mixture refluxed for a further 20 hours. The cooled reaction mixture was then concentrated to afford a yellow solid. The crude product was re-crystallized from methanol (100 mL) to give 8-bromo-3,6-di-tert-butyl-3,4-dihydro-2H-benzo[e][1,3]oxazine (36.74 g, 85% yield) as a cream crystalline solid.

Analysis calculated for C$_{16}$H$_{24}$BrNO: C, 58.90; H, 7.41; N, 4.29; Br, 24.49. found: C, 59.02; H, 7.42; N, 4.26; Br, 24.87.

Intermediate 2

3-(Trifluoromethyl)pyridine-5-boronic acid

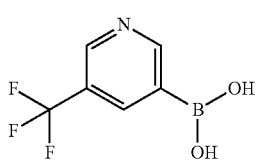

To a solution of 3-bromo-5-(trifluoromethyl)pyridine (2.5 g, 11.06 mmol) and triisopropylborate (3.06 mL, 13.27 mmol) in anhydrous tetrahydrofuran (20 mL) at −78° C. under nitrogen was added dropwise a solution of n-butyl lithium in hexane (2.5 M, 4.9 mL, 12.17 mmol) The reaction was stirred at −78° C. for 3 hours then allowed to warm slowly to −10° C. The reaction mixture was then quenched by the addition of water (20 mL) and the tetrahydrofuran removed under reduced pressure. The resulting aqueous phase was diluted with water (40 mL) and washed with ether (2×40 mL). The aqueous phase was then acidified to pH 5 by the addition of acetic acid and the resulting suspension extracted with ethyl acetate (80 mL). The organic phase was separated, dried (MgSO$_4$), filtered and concentrated under reduced pressure to give 3-(trifluoromethyl)pyridine-5-boronic acid (2.022 g, 96% yield) as a tan solid.

HPLC/MS R$_t$=1.47 min, m/z 192.1 (M+H$^+$).

Intermediate 3

2-(Trifluoromethyl)pyridine-4-boronic acid

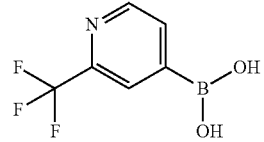 [SMILES: OB(O)c1ccnc(C(F)(F)F)c1]

To a solution of 4-iodo-2-(trifluoromethyl)pyridine [purchased from Matrix Scientific] (2.5 g, 9.16 mmol) and triisopropylborate (2.54 mL, 10.99 mmol) in anhydrous tetrahydrofuran (20 mL) at −78° C. under nitrogen was added dropwise a solution of n-butyl lithium in hexane (2.5 M, 4.03 mL, 10.07 mmol). The reaction was stirred at −78° C. for 2½ hours then allowed to warm slowly to −10° C. over 1 hour. The reaction mixture was then quenched by the addition of water (20 mL) and the tetrahydrofuran removed under reduced pressure. The resulting aqueous phase was diluted with water (40 mL) and washed with ether (2×40 mL). The aqueous phase was then acidified to pH 5 by the addition of acetic acid and the resulting oily suspension extracted with ether (100 mL). The organic phase was separated, washed with saturated brine (2×50 mL), dried (MgSO$_4$), filtered and concentrated under reduced pressure to give an off-white foam. Ether (12 mL) and hexanes (24 mL) were added and the resulting suspension stirred vigorously for 30 minutes then filtered to give 2-(trifluoromethyl)pyridine-4-boronic acid (1.163 g, 67% yield) as a cream solid.

HPLC/MS R$_t$=1.54 min, m/z 192.1 (M+H$^+$).

Intermediate 4

2-(tert-Butyl)pyridine-5-boronic acid

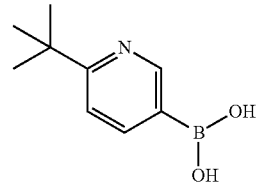

Step 1: 5-Bromo-2-(tert-butyl)pyridine

To a suspension of copper cyanide (1.791 g, 20 mmol) in dry tetrahydrofuran (40 mL) at −78° C. under nitrogen was added dropwise a solution of tert-butylmagnesium chloride in tetrahydrofuran (1.0 M, 40 mL, 40 mmol) over 20 minutes. A solution of 5-bromo-2-iodopyridine (5.68 g, 20 mmol) in dry tetrahydrofuran (20 mL) was then added via cannula and the reaction mixture stirred at −78° C. for 1 hour then allowed to warm slowly to room temperature. The reaction was quenched by the addition of 25% aqueous ammonium hydroxide solution (28-30%, 100 mL) and the mixture partitioned between ethyl acetate (500 mL) and 25% aqueous ammonium hydroxide solution (28-30%, 400 mL). The organic phase was separated, washed with water (400 mL) and saturated brine (100 mL), dried ($MgSO_4$), filtered and concentrated under reduced pressure to give a brown oil. The crude product was purified by chromatography on silica eluting with a solvent gradient of 0 to 10% ethyl acetate in hexanes to give 5-bromo-2-(tert-butyl)pyridine (1.6186 g, 38% yield) as a colorless oil.

HPLC/MS $R_t$=6.27 min, m/z 214.1 and 216.1 ($M+H^+$).

Step 2: 2-(tert-Butyl)pyridine-5-boronic acid

To a solution of 5-bromo-2-(tert-butyl)pyridine (1 g, 4.67 mmol) and triisopropylborate (1.29 mL, 5.60 mmol) in anhydrous tetrahydrofuran (10 mL) at −78° C. under nitrogen was added dropwise a solution of n-butyl lithium in hexane (2.5 M, 2.06 mL, 5.14 mmol). The reaction was stirred at −78° C. for 2½ hours then allowed to warm slowly to −10° C. over 1 hour. The reaction was quenched by the addition of water (10 mL) and the tetrahydrofuran removed under reduced pressure. The resulting aqueous suspension was diluted with water (30 mL) and washed with ether (30 mL). The aqueous phase was acidified to pH 6 by the addition of acetic acid and the resulting milky suspension extracted with ether (2×20 mL). The combined organic extracts were washed with saturated brine (2×50 mL), dried ($MgSO_4$), filtered and concentrated under reduced pressure to give a white foam. Ether (5 mL) and hexanes (40 mL) were added and the resulting suspension stirred vigorously for 30 minutes then filtered to give 2-(tert-butyl)pyridine-5-boronic acid (0.5093 g, 61% yield) as a white solid.

HPLC/MS $R_t$=0.93 min, m/z 180.1 ($M+H^+$).

Intermediate 5

(5-(tert-Butyl)-2-methoxyphenyl)boronic acid

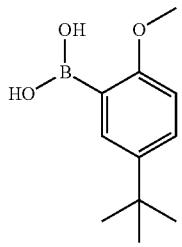

Step 1: 2-Bromo-4-(tert-butyl)-1-methoxybenzene

Iodomethane (10.0 mL, 0.161 mol) was added to a mixture of 2-bromo-4-(tert-butyl)phenol [Intermediate 1, Step 1] (29.5 g, 0.129 mol) and potassium carbonate (42.7 g, 0.309 mol) in dry acetone (400 mL) and the reaction mixture refluxed under nitrogen for 22 hours. The cooled reaction mixture was then concentrated and the residue partitioned between ethyl acetate (400 mL) and 0.3 M aqueous sodium hydroxide solution (300 mL). The organic phase was separated, washed with water (300 mL) and saturated brine (300 mL), dried ($MgSO_4$), filtered and concentrated under reduced pressure to give 2-bromo-4-(tert-butyl)-1-methoxybenzene (32.09 g, 100% yield) as a light yellow oil.

HPLC/MS $R_t$=7.47 min.

Step 2: (5-(tert-Butyl)-2-methoxyphenyl)boronic acid n-Butyllithium in hexane (2.5 M, 18.1 mL, 45.24 mmol) was added dropwise to a solution of 2-bromo-4-(tert-butyl)-1-methoxybenzene (10.0 g, 41.13 mmol) and triisopropyl borate (11.39 mL, 49.35 mmol) in tetrahydrofuran (90 mL) at −78° C. under nitrogen. The reaction mixture was stirred at −78° C. for 3 hours then allowed to warm slowly to 0° C. over 90 minutes. The reaction was then quenched by the addition of water (90 mL) and the tetrahydrofuran removed under reduced pressure. The resulting aqueous suspension was partitioned between diethyl ether (80 mL) and 1.0 M aqueous sodium hydroxide solution (100 mL). The aqueous phase was separated, cooled to 0° C. then acidified to pH 1 by the addition of concentrated hydrochloric acid. The resulting white suspension was stood at 0° C. for 15 minutes then filtered washing the solid product with water and cold hexane to give (5-(tert-butyl)-2-methoxyphenyl)boronic acid (6.349 g, 74% yield) as a white crystalline solid.

HPLC/MS $R_t$=5.04 min, m/z 209.1 ($M+H^+$).

Intermediate 6

6,8-Dibromo-3-(tert-butyl)-3,4-dihydro-2H-benzo[e][1,3]oxazine

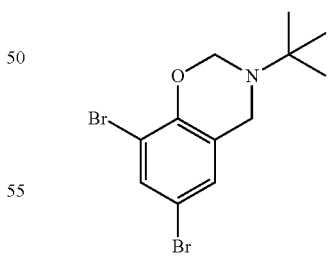

tert-Butylamine (16.1 g, 0.22 mol) was added to a mixture of 2,4-dibromophenol (11.1 g, 0.044 mol) and paraformaldehyde (6.61 g, 0.22 mol) in 2-propanol (110 mL) and the reaction mixture refluxed under nitrogen overnight. The cooled reaction mixture was filtered and the wet cake was rinsed with 2-propanol. The wet cake was dried by suction to give 6,8-dibromo-3-(tert-butyl)-3,4-dihydro-2H-benzo[e][1,3]oxazine (12.66 g, 82.8% yield) as a solid.

HPLC/MS $R_t$=3.78 min, m/z 336.0 (M+H$^+$ hydrolysed product).

Intermediate 7

(5-(tert-Butyl)-2-((2-methoxyethoxy)methoxy)phenyl)boronic acid

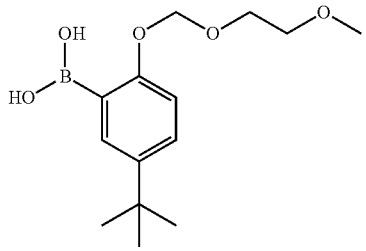 [SMILES: COCCOCOc1ccc(C(C)(C)C)cc1B(O)O]

Step 1: 2-Bromo-4-(tert-butyl)-1-((2-methoxyethoxy)methoxy)benzene

To a solution of 2-bromo-4-(tert-butyl)phenol [Intermediate 1, Step 1] (5.0 g, 21.8 mmol) and triethylamine (4.4 g, 43.5 mmol) in anhydrous dichloromethane (20 mL) at room temperature under nitrogen was added dropwise 2-methoxyethoxymethyl chloride (2.5 mL, 21.9 mmol) and the reaction mixture stirred overnight. The reaction mixture was poured into water (100 mL), the organic phase separated, dried (MgSO$_4$), filtered and concentrated under reduced pressure to give 2-bromo-4-(tert-butyl)-1-((2-methoxyethoxy)methoxy)benzene (5.0 g, 72% yield).

MS m/z 317 and 319 (M+H$^+$).

Step 2: (5-(tert-Butyl)-2-((2-methoxyethoxy)methoxy)phenyl)boronic acid n-Butyllithium in hexane (2.5 M, 4.2 mL, 10.5 mmol) was added dropwise to a solution of give 2-bromo-4-(tert-butyl)-1-((2-methoxyethoxy)methoxy)benzene (3.0 g, 9.46 mmol) and trimethyl borate (1.2 mL, 10.76 mmol) in anhydrous tetrahydrofuran (20 mL) at −78° C. under nitrogen. The reaction mixture was stirred at −78° C. for 20 minutes then at 0° C. for an additional 20 minutes. The reaction was then quenched by the addition of water (20 mL) and the mixture extracted with ether (100 mL). The organic layer was separated, dried (MgSO$_4$), filtered and concentrated under reduced pressure to give (5-(tert-butyl)-2-((2-methoxyethoxy)methoxy)phenyl)boronic acid (2.61 g, 98% yield).

MS m/z 283 (M+H$^+$).

Intermediate 8

3-Bromo-5-(tert-butyl)-2-hydroxybenzaldehyde

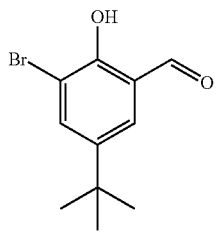

A mixture of 2-bromo-4-(tert-butyl)phenol [Intermediate 1, Step 1] (6.87 g, 30 mmol) and hexamethylenetetramine (20 g, 143 mmol) in trifluoroacetic acid (60 mL) was heated at 90° C. under nitrogen for 22 hours. The hot reaction mixture was poured into 1M aqueous hydrochloric acid (200 mL) and the mixture stirred vigorously for 6 hours. The resulting suspension was filtered to give 3-bromo-5-(tert-butyl)-2-hydroxybenzaldehyde (6.79 g, 88% yield) as a yellow solid.

HPLC/MS $R_t$=6.92 min, m/z 257.0 and 259.0 (M+H$^+$).

Example 1

4-(tert-Butyl)-2-((tert-butylamino)methyl)-6-(6-(trifluoromethyl)pyridin-3-yl)phenol hydrochloride

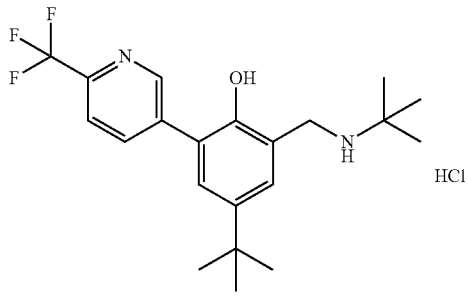 [SMILES: CC(C)(C)NCc1cc(C(C)(C)C)cc(-c2ccc(C(F)(F)F)nc2)c1O ; Cl]

A mixture of 8-bromo-3,6-di-tert-butyl-3,4-dihydro-2H-benzo[e][1,3]oxazine (Intermediate 1) (2.0 g, 6.13 mmol), 2-(trifluoromethyl)pyridine-5-boronic acid [purchased from Frontier Scientific] (1.17 g, 6.13 mmol) and potassium carbonate (1.27 g, 9.20 mmol) in dimethoxyethane (15 mL) and water (5 mL) was purged with nitrogen for 20 minutes. Tetrakis(triphenylphosphine)palladium(0) (354.2 mg, 0.31 mmol) was then added and the mixture heated at 80° C. in a sealed vial for 24 hours. The cooled reaction mixture was then partitioned between ethyl acetate (80 mL) and 1M aqueous sodium hydroxide (80 mL). The organic phase was separated, washed with water (80 mL) and saturated brine (80 mL), dried (MgSO$_4$), filtered and concentrated under reduced pressure to give an orange syrup. The product was purified using flash chromatography on silica eluting with a solvent gradient of 0 to 30% ethyl acetate in hexanes to give the intermediate 3,4-dihydro-2H-benzo[e][1,3]oxazine (1.875 g, 78% yield) as a yellow syrup. The 3,4-dihydro-2H-benzo[e][1,3]oxazine (1.875 g, 4.78 mmol) was dissolved in ethanol (135 mL), 1.0 M aqueous hydrochloric acid (45 mL) added and the reaction mixture stirred at room temperature for 4 days. The reaction mixture was then concentrated under reduced pressure and the residue partitioned between ethyl acetate (100 mL) and 10% w/v aqueous sodium carbonate solution (100 mL). The organic phase was separated, washed with water (100 mL) and saturated brine (100 mL), dried (MgSO$_4$), filtered and concentrated under reduced pressure to give a yellow syrup. The product was purified using flash chromatography on silica eluting with a solvent gradient of 0 to 30% ethyl acetate in hexanes to give the product as a yellow syrup that partially crystallized (1.435 g). The product was dissolved in absolute ethanol (50 mL), 1.0 M aqueous hydrochloric acid (15.1 mL, 15.1 mmol) added, the mixture stood for 20 minutes then concentrated under reduced pressure and the product azeotroped with absolute ethanol (3×60 mL) to give a cream solid. Diethyl ether (50 mL) and absolute ethanol (10 mL) were added and the resulting suspension stirred vigorously overnight then filtered to afford 4-(tert-butyl)-2-((tert-butylamino)methyl)-6-(6-(trifluoromethyl)pyridin-3-yl)phenol hydrochloride (1.083 g, 54% yield) as a white solid.

HPLC/MS $R_t$=2.89 min, m/z 381.1 (M+H$^+$); analysis calculated for $C_{21}H_{27}F_3N_2O\cdot HCl$: C, 60.50; H, 6.77; N, 6.72; Cl, 8.50. found: C, 60.71; H, 6.56; N, 6.60; Cl, 8.56.

Example 2

4-(tert-Butyl)-2-((tert-butylamino)methyl)-6-(5-chlorothiophen-2-yl)phenol hydrochloride

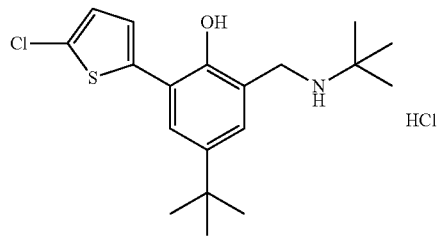 [SMILES: CC(C)(C)NCc1cc(C(C)(C)C)cc(-c2ccc(Cl)s2)c1O ; Cl]

The title compound was prepared as a white solid using the procedure described in Example 1 from 8-bromo-3,6-di-tert-butyl-3,4-dihydro-2H-benzo[e][1,3]oxazine (Intermediate 1) and 5-chlorothiophene-2-boronic acid [purchased from Frontier Scientific].

HPLC/MS $R_t$=3.82 min, m/z 352.1 and 354.1 (M+H$^+$).

Example 3

4-(tert-Butyl)-2-((tert-butylamino)methyl)-6-(quinolin-3-yl)phenol dihydrochloride

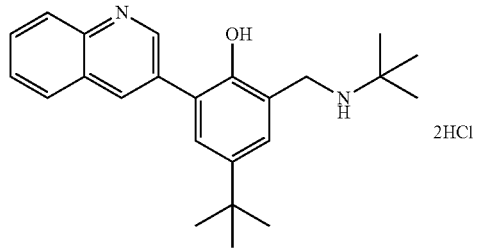 [SMILES: CC(C)(C)NCc1cc(C(C)(C)C)cc(-c2cnc3ccccc3c2)c1O ; "2HCl"]

The title compound was prepared as a hygroscopic yellow solid using the procedure described in Example 1 from 8-bromo-3,6-di-tert-butyl-3,4-dihydro-2H-benzo[e][1,3]oxazine (Intermediate 1) and quinoline-3-boronic acid [purchased from Frontier Scientific].

HPLC/MS $R_t$=1.64 min, m/z 363.3 (M+H$^+$); analysis calculated for $C_{24}H_{30}N_2O\cdot 2HCl\cdot 1.3H_2O$: C, 62.82; H, 7.60; N, 6.11; Cl, 15.45. found: C, 62.72; H, 7.61; N, 5.98; Cl, 15.54.

Example 4

4-(tert-Butyl)-2-((tert-butylamino)methyl)-6-(quinolin-5-yl)phenol dihydrochloride

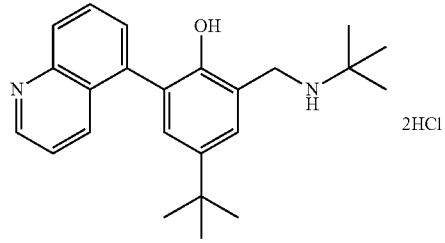 [SMILES: CC(C)(C)NCc1cc(C(C)(C)C)cc(-c2cccc3ncccc23)c1O ; "2HCl"]

The title compound was prepared as a hygroscopic cream solid using the procedure described in Example 1 from 8-bromo-3,6-di-tert-butyl-3,4-dihydro-2H-benzo[e][1,3]oxazine (Intermediate 1) and quinoline-5-boronic acid [purchased from Frontier Scientific].

HPLC/MS $R_t$=1.20 min, m/z 363.3 (M+H$^+$); analysis calculated for $C_{24}H_{30}N_2O\cdot 2HCl\cdot 1H_2O$: C, 63.57; H, 7.56; N, 6.18; Cl, 15.64. found: C, 63.41; H, 7.34; N, 6.02; Cl, 15.64.

Example 5

4-(tert-Butyl)-2-((tert-butylamino)methyl)-6-(quinolin-6-yl)phenol dihydrochloride

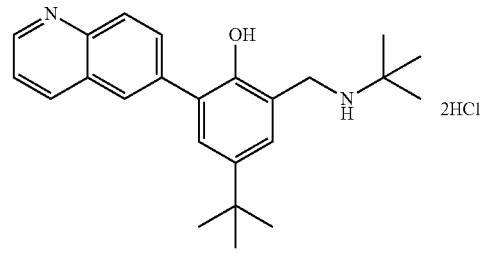 [SMILES: CC(C)(C)NCc1cc(C(C)(C)C)cc(-c2ccc3ncccc3c2)c1O ; "2HCl"]

The title compound was prepared as a hygroscopic cream solid using the procedure described in Example 1 from 8-bromo-3,6-di-tert-butyl-3,4-dihydro-2H-benzo[e][1,3]oxazine (Intermediate 1) and quinoline-6-boronic acid [purchased from Frontier Scientific].

HPLC/MS $R_t$=1.23 min, m/z 363.3 (M+H$^+$).

Example 6

2-(Benzofuran-2-yl)-4-(tert-butyl)-6-((tert-butylamino)methyl)phenol hydrochloride

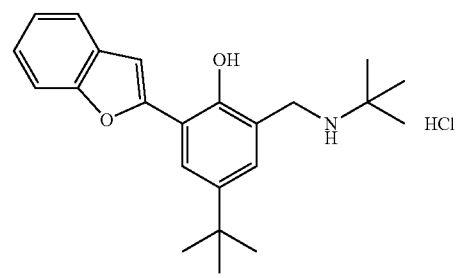 [SMILES: CC(C)(C)NCc1cc(C(C)(C)C)cc(-c2cc3ccccc3o2)c1O ; Cl]

The title compound was prepared as a white solid using the procedure described in Example 1 from 8-bromo-3,6-di-tert-butyl-3,4-dihydro-2H-benzo[e][1,3]oxazine (Intermediate 1) and benzofuran-2-boronic acid [purchased from Frontier Scientific].

HPLC/MS $R_t$=3.88 min, m/z 352.3 (M+H$^+$); analysis calculated for $C_{23}H_{29}NO_2\cdot HCl$: C, 71.21; H, 7.79; N, 3.61; Cl, 9.14. found: C, 71.42; H, 7.97; N, 3.63; Cl, 9.18.

Example 7

2-(Benzo[b]thiophen-2-yl)-4-(tert-butyl)-6-((tert-butylamino)methyl)phenol hydrochloride

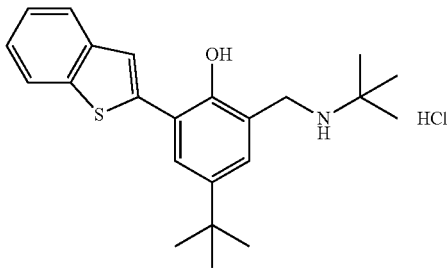 [SMILES: CC(C)(C)NCc1cc(C(C)(C)C)cc(-c2cc3ccccc3s2)c1O ; Cl]

The title compound was prepared as a white solid using the procedure described in Example 1 replacing 2-(trifluoromethyl)pyridine-5-boronic acid with benzothiophene-2-boronic acid [purchased from Frontier Scientific].

HPLC/MS $R_f$=4.11 min, m/z 368.1 (M+H$^+$); analysis calculated for $C_{23}H_{29}NOS$ HCl: C, 68.38; H, 7.48; N, 3.47; Cl, 8.78. found: C, 68.58; H, 7.55; N, 3.43; Cl, 8.85.

Example 8

4-(tert-Butyl)-2-((tert-butylamino)methyl)-6-(quinolin-4-yl)phenol dihydrochloride

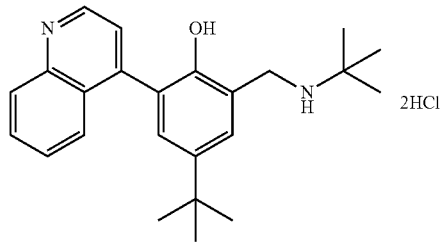 [SMILES: CC(C)(C)NCc1cc(C(C)(C)C)cc(-c2ccnc3ccccc23)c1O ; "2HCl"]

The title compound was prepared as a hygroscopic white solid using the procedure described in Example 1 from 8-bromo-3,6-di-tert-butyl-3,4-dihydro-2H-benzo[e][1,3]oxazine (Intermediate 1) and quinoline-4-boronic acid [purchased from Frontier Scientific].

HPLC/MS $R_f$=1.22 min, m/z 363.3 (M+H$^+$); analysis calculated for $C_{24}H_{30}N_2O$ 2HCl 0.2H$_2$O: C, 65.66; H, 7.44; N, 6.38; Cl, 16.15. found: C, 65.68; H, 7.32; N, 6.36; Cl, 15.96.

Example 9

4-(tert-Butyl)-2-((tert-butylamino)methyl)-6-(1-methyl-3-(trifluoromethyl)-1H-pyrazol-5-yl)phenol hydrochloride

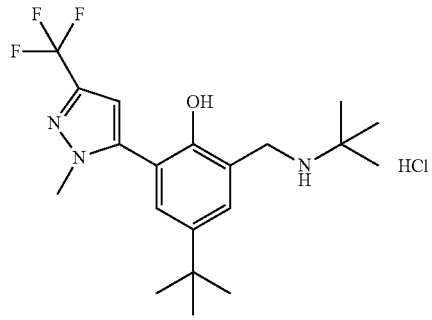 [SMILES: Cn1nc(C(F)(F)F)cc1-c1cc(C(C)(C)C)cc(CNC(C)(C)C)c1O ; Cl]

The title compound was prepared as a white solid using the procedure described in Example 1 from 8-bromo-3,6-di-tert-butyl-3,4-dihydro-2H-benzo[e][1,3]oxazine (Intermediate 1) and 1-methyl-3-trifluoromethyl-pyrazole-5-boronic acid [purchased from Frontier Scientific].

HPLC/MS $R_f$=3.93 min, m/z 384.2 (M+H$^+$); analysis calculated for $C_{20}H_{28}F_3N_3O$ HCl: C, 57.21; H, 6.96; N, 10.01; Cl, 8.44. found: C, 56.78; H, 6.73; N, 9.76; Cl, 8.39.

Example 10

4-(tert-Butyl)-2-((tert-butylamino)methyl)-6-(6-isopropoxypyridin-3-yl)phenol dihydrochloride

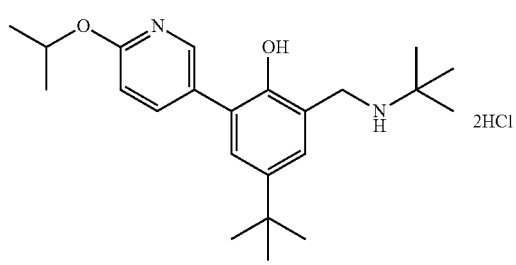 [SMILES: CC(C)Oc1ccc(-c2cc(C(C)(C)C)cc(CNC(C)(C)C)c2O)cn1 ; "2HCl"]

The title compound was prepared as a white hygroscopic solid using the procedure described in Example 1 from 8-bromo-3,6-di-tert-butyl-3,4-dihydro-2H-benzo[e][1,3]oxazine (Intermediate 1) and 2-isopropoxy-pyridine-5-boronic acid [purchased from Combi-Blocks].

HPLC/MS $R_f$=4.11 min, m/z 371.2 (M+H$^+$); analysis calculated for $C_{23}H_{34}N_2O_2$ 2HCl 0.6H$_2$O: C, 60.81; H, 8.25; N, 6.17; Cl, 15.61. found: C, 61.06; H, 8.16; N, 6.10; Cl, 15.21.

Example 11

2-(6-Aminopyridin-3-yl)-4-(tert-butyl)-6-((tert-butylamino)methyl)phenol dihydrochloride

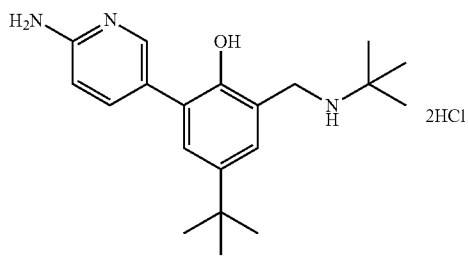 [SMILES: CC(C)(C)NCc1cc(C(C)(C)C)cc(-c2ccc(N)nc2)c1O ; "2HCl"]

The title compound was prepared as a white hygroscopic solid using the procedure described in Example 1 from 8-bromo-3,6-di-tert-butyl-3,4-dihydro-2H-benzo[e][1,3]oxazine (Intermediate 1) and 2-aminopyridine-5-boronic acid pinacol ester [purchased from Combi-Blocks].

HPLC/MS $R_f$=0.94 min, m/z 328.3 (M+H$^+$); analysis calculated for $C_{20}H_{29}N_3O$ 2HCl 0.25H$_2$O: C, 59.33; H, 7.84; N, 10.38; Cl, 17.51. found: C, 59.60; H, 7.90; N, 10.11; Cl, 17.16.

Example 12

4-(tert-Butyl)-2-((tert-butylamino)methyl)-6-(6-methoxypyridin-3-yl)phenol dihydrochloride

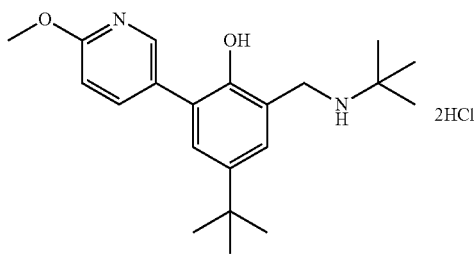 [SMILES: COc1ccc(-c2cc(C(C)(C)C)cc(CNC(C)(C)C)c2O)cn1 ; "2HCl"]

The title compound was prepared as a white hygroscopic solid using the procedure described in Example 1 replacing 2-(trifluoromethyl)pyridine-5-boronic acid with 2-methoxypyridine-5-boronic acid [purchased from Frontier Scientific].

HPLC/MS $R_f$=3.04 min, m/z 343.2 (M+H$^+$); analysis calculated for $C_{21}H_{30}N_2O_2$ 2HCl 1.25H$_2$O: C, 57.60; H, 7.94; N, 6.40; Cl, 16.19. found: C, 57.66; H, 7.98; N, 6.38; Cl, 15.96.

Example 13

4-(tert-Butyl)-2-((tert-butylamino)methyl)-6-(isoquinolin-4-yl)phenol dihydrochloride

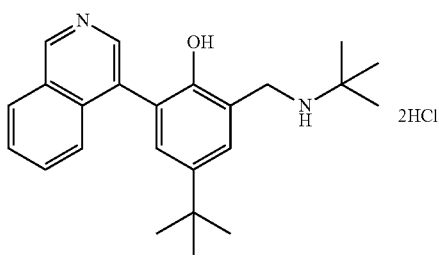 [SMILES: CC(C)(C)NCc1cc(C(C)(C)C)cc(-c2cncc3ccccc23)c1O ; "2HCl"]

The title compound was prepared as a white hygroscopic solid using the procedure described in Example from 8-bromo-3,6-di-tert-butyl-3,4-dihydro-2H-benzo[e][1,3]oxazine (Intermediate 1) and isoquinoline-4-boronic acid pinacol ester [purchased from Combi-Blocks].

HPLC/MS $R_f$=1.65 min, m/z 363.3 (M+H$^+$); analysis calculated for $C_{24}H_{30}N_2O$ 2HCl 1.75H$_2$O: C, 61.73; H, 7.66; N, 6.00; Cl, 15.18. found: C, 61.38; H, 7.62; N, 5.90; Cl, 15.32.

Example 14

4-(tert-Butyl)-2-((tert-butylamino)methyl)-6-(6-(dimethylamino)pyridin-3-yl)phenol dihydrochloride

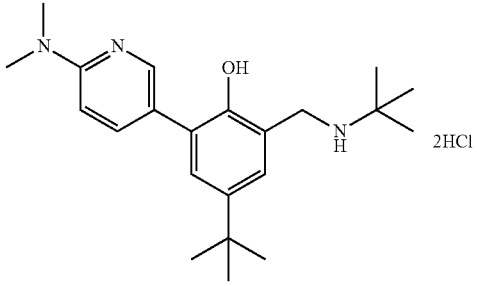 [SMILES: CN(C)c1ccc(-c2cc(C(C)(C)C)cc(CNC(C)(C)C)c2O)cn1 ; "2HCl"]

The title compound was prepared as a white hygroscopic solid using the procedure described in Example 1 from 8-bromo-3,6-di-tert-butyl-3,4-dihydro-2H-benzo[e][1,3]oxazine (Intermediate 1) and 2-(dimethylamino)pyridine-5-boronic acid [purchased from Combi-Blocks].

HPLC/MS $R_f$=0.89 min, m/z 356.3 (M+H$^+$); analysis calculated for $C_{22}H_{33}N_3O$ 2HCl 0.4H$_2$O: C, 60.65; H, 8.28; N, 9.65; Cl, 16.28. found: C, 60.63; H, 7.95; N, 9.52; Cl, 16.38.

Example 15

4-(tert-Butyl)-2-((tert-butylamino)methyl)-6-(6-(pyrrolidin-1-yl)pyridin-3-yl)phenol dihydrochloride

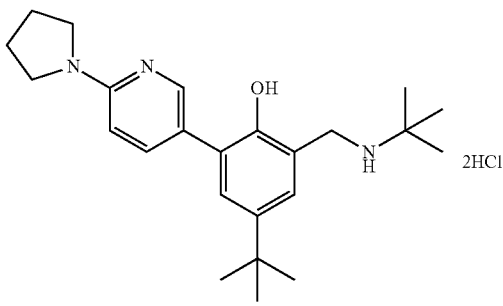 [SMILES: CC(C)(C)NCc1cc(C(C)(C)C)cc(-c2ccc(N3CCCC3)nc2)c1O ; "2HCl"]

The title compound was prepared as a white hygroscopic solid using the procedure described in Example 1 replacing 2-(trifluoromethyl)pyridine-5-boronic acid with 6-(pyrrolidin-1-yl)pyridine-3-boronic acid [purchased from Combi-Blocks].

HPLC/MS $R_f$=1.00 min, m/z 382.3 (M+H$^+$); analysis calculated for $C_{24}H_{35}N_3O$ 2HCl 0.4H$_2$O: C, 62.44; H, 8.25; N, 9.10; Cl, 15.36. found: C, 62.58; H, 7.93; N, 9.03; Cl, 15.49.

Example 16

4-(tert-Butyl)-2-((tert-butylamino)methyl)-6-(2-methoxypyridin-4-yl)phenol dihydrochloride

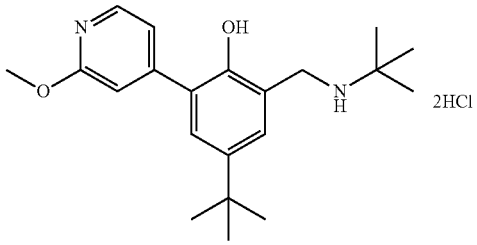 [SMILES: COc1cc(-c2cc(C(C)(C)C)cc(CNC(C)(C)C)c2O)ccn1 ; "2HCl"]

The title compound was prepared as a white solid using the procedure described in Example 1 from 8-bromo-3,6-di-tert-butyl-3,4-dihydro-2H-benzo[e][1,3]oxazine (Intermediate 1) and 2-methoxypyridine-4-boronic acid [purchased from Combi-Blocks].

HPLC/MS $R_f$=1.70 min, m/z 343.2 (M+H$^+$); analysis calculated for $C_{21}H_{30}N_2O_2$ 2HCl: C, 60.72; H, 7.76; N, 6.74; Cl, 17.07. found: C, 60.66; H, 7.72; N, 6.64; Cl, 17.02.

Example 17

4-(tert-Butyl)-2-((tert-butylamino)methyl)-6-(5-methoxypyridin-3-yl)phenol dihydrochloride

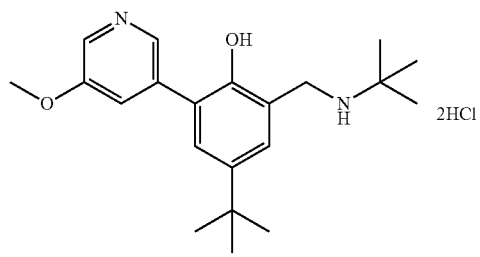 [SMILES: COc1cncc(-c2cc(C(C)(C)C)cc(CNC(C)(C)C)c2O)c1 ; "2HCl"]

The title compound was prepared as a white solid using the procedure described in Example 1 from 8-bromo-3,6-di-tert-butyl-3,4-dihydro-2H-benzo[e][1,3]oxazine (Intermediate 1) and 5-methoxypyridine-3-boronic acid [purchased from Combi-Blocks].

HPLC/MS $R_f$=1.23 min, m/z 343.2 (M+H$^+$); analysis calculated for $C_{21}H_{30}N_2O_2$ 2HCl: C, 60.72; H, 7.76; N, 6.74; Cl, 17.07. found: C, H, N, Cl.

Example 18

4-(tert-Butyl)-2-((tert-butylamino)methyl)-6-(5-(trifluoromethyl)pyridin-3-yl)phenol 1.4 hydrochloride

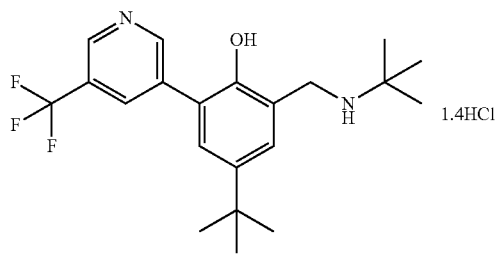

The title compound was prepared as a white solid using the procedure described in Example 1 from 8-bromo-3,6-di-tert-butyl-3,4-dihydro-2H-benzo[e][1,3]oxazine (Intermediate 1) and 3-(trifluoromethyl)pyridine-5-boronic acid [Intermediate 2].

HPLC/MS $R_f$=3.28 min, m/z 381.1 (M+H$^+$); analysis calculated for $C_{21}H_{27}F_3N_2O$ 1.4HCl: C, 58.45; H, 6.63; N, 6.49; Cl, 11.50. found: C, 58.11; H, 7.05; N, 6.35; Cl, 11.15.

Example 19

5-(5-(tert-Butyl)-3-((tert-butylamino)methyl)-2-hydroxyphenyl)picolinonitrile hydrochloride

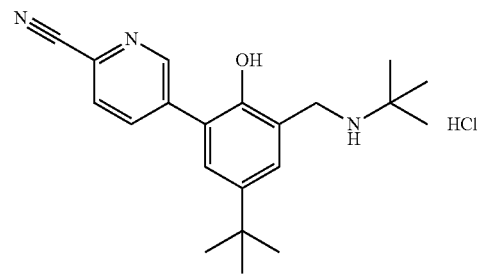 [SMILES: CC(C)(C)NCc1cc(C(C)(C)C)cc(-c2ccc(C#N)nc2)c1O ; Cl]

The title compound was prepared as a white solid using the procedure described in Example 1 from 8-bromo-3,6-di-tert-butyl-3,4-dihydro-2H-benzo[e][1,3]oxazine (Intermediate 1) and 2-cyanopyridine-5-boronic acid pinacol ester [purchased from Frontier Scientific].

Example 20

4-(tert-Butyl)-2-((tert-butylamino)methyl)-6-(2-(trifluoromethyl)pyridin-4-yl)phenol hydrochloride

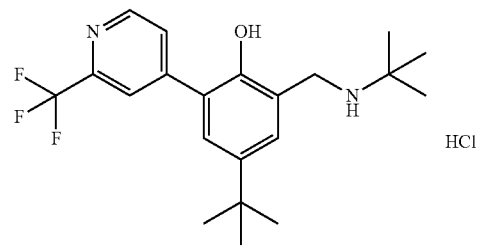 [SMILES: CC(C)(C)NCc1cc(C(C)(C)C)cc(-c2ccnc(C(F)(F)F)c2)c1O ; Cl]

The title compound was prepared as a white solid using the procedure described in Example 1 from 8-bromo-3,6-di-tert-butyl-3,4-dihydro-2H-benzo[e][1,3]oxazine (Intermediate 1) and 2-(trifluoromethyl)pyridine-4-boronic acid [Intermediate 3].

HPLC/MS $R_f$=3.52 min, m/z 381.1 (M+H$^+$); analysis calculated for $C_{21}H_{27}F_3N_2O$ HCl: C, 60.50; H, 6.77; N, 6.72; Cl, 8.50. found: C, 60.29; H, 6.79; N, 6.71; Cl, 8.82.

Example 21

4-(tert-Butyl)-2-((tert-butylamino)methyl)-6-(5-chloropyridin-3-yl)phenol dihydrochloride

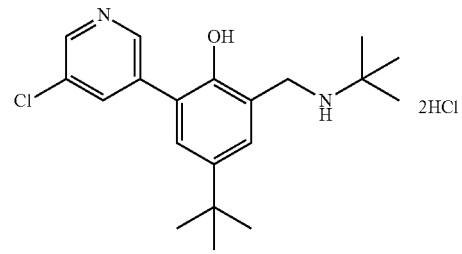 [SMILES: CC(C)(C)NCc1cc(C(C)(C)C)cc(-c2cncc(Cl)c2)c1O ; "2HCl"]

The title compound was prepared as a white solid using the procedure described in Example 1 from 8-bromo-3,6-di-tert-butyl-3,4-dihydro-2H-benzo[e][1,3]oxazine (Intermediate 1) and 3-chloropyridine-5-boronic acid [purchased from Frontier Scientific].

HPLC/MS $R_t$=2.71 min, m/z 347.2 and 349.1 (M+H$^+$); analysis calculated for $C_{20}H_{22}ClN_2O$ 2HCl: C, 57.22; H, 6.96; N, 6.67; Cl, 25.33. found: C, 56.97; H, 6.93; N, 6.53; Cl, 25.16.

Example 22

4-(tert-Butyl)-2-(6-(tert-butyl)pyridin-3-yl)-6-((tert-butylamino)methyl)phenol dihydrochloride

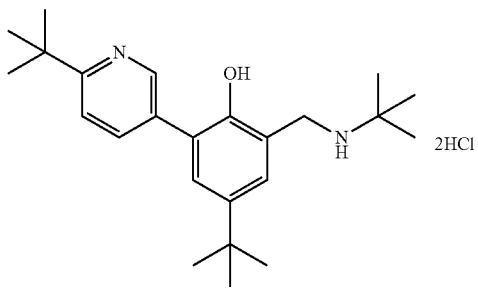 [SMILES: CC(C)(C)NCc1cc(C(C)(C)C)cc(-c2ccc(C(C)(C)C)nc2)c1O ; "2HCl"]

The title compound was prepared as a white hygroscopic solid using the procedure described in Example 1 from 8-bromo-3,6-di-tert-butyl-3,4-dihydro-2H-benzo[e][1,3]oxazine (Intermediate 1) and 2-(tert-butyl)pyridine-5-boronic acid [Intermediate 4].

HPLC/MS $R_t$=2.55 min, m/z 369.4 (M+H$^+$); analysis calculated for $C_{24}H_{36}N_2O$ 2HCl $H_2O$: C, 62.73; H, 8.77; N, 6.10; Cl, 15.43. found: C, 62.74; H, 8.70; N, 5.91; Cl, 15.14.

Example 23

4-(tert-Butyl)-2-((tert-butylamino)methyl)-6-(6-chloropyridin-3-yl)phenol hydrochloride

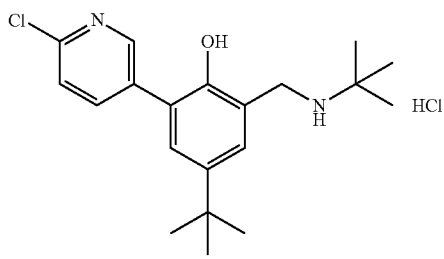 [SMILES: CC(C)(C)NCc1cc(C(C)(C)C)cc(-c2ccc(Cl)nc2)c1O ; Cl]

The title compound was prepared as a white solid using the procedure described in Example 1 from 8-bromo-3,6-di-tert-butyl-3,4-dihydro-2H-benzo[e][1,3]oxazine (Intermediate 1) and 2-chloropyridine-5-boronic acid [purchased from Frontier Scientific].

HPLC/MS $R_t$=3.43 min, m/z 347.2 and 349.1 (M+H$^+$); analysis calculated for $C_{20}H_{22}ClN_2O$ HCl: C, 62.66; H, 7.36; N, 7.31; Cl, 18.50. found: C, 62.39; H, 7.54; N, 7.25; Cl, 18.54.

Example 24

4-(tert-Butyl)-2-((tert-butylamino)methyl)-6-(pyrimidin-5-yl)phenol hydrochloride

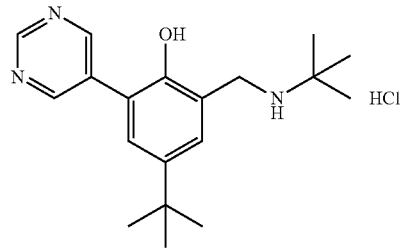 [SMILES: CC(C)(C)NCc1cc(C(C)(C)C)cc(-c2cncnc2)c1O ; Cl]

The title compound was prepared as a white solid using the procedure described in Example 1 from 8-bromo-3,6-di-tert-butyl-3,4-dihydro-2H-benzo[e][1,3]oxazine (Intermediate 1) and pyrimidine-5-boronic acid. HPLC/MS $R_t$=1.30 min, m/z 314.3 (M+H$^+$).

Example 25

4-(tert-Butyl)-2-((tert-butylamino)methyl)-6-(5-methylpyridin-2-yl)phenol dihydrochloride

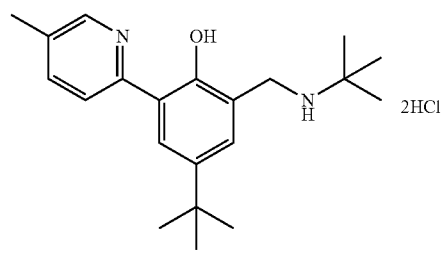 [SMILES: Cc1ccc(-c2cc(C(C)(C)C)cc(CNC(C)(C)C)c2O)nc1 ; "2HCl"]

Step 1: 2-(5-(tert-Butyl)-2-methoxyphenyl)-5-methylpyridine

A mixture of 2-bromo-5-methylpyridine [purchased from TCI] (0.827 g, 4.81 mmol), (5-(tert-butyl)-2-methoxyphenyl)boronic acid [Intermediate 5] (1.2 g, 5.77 mmol) and potassium carbonate (0.997 g, 7.21 mmol) in dimethoxyethane (15 mL) and water (5 mL) was purged with nitrogen for 20 minutes. Tetrakis(triphenylphosphine)palladium(0) (277.8 mg, 0.24 mmol) was added and the reaction mixture heated to 80° C. in a sealed vial for 22 hours. The cooled reaction mixture was partitioned between ethyl acetate (80 mL) and 1 M aqueous sodium hydroxide solution (80 mL), the organic phase separated, washed with water (80 mL) and saturated brine (80 mL), dried (MgSO$_4$), filtered and concentrated under reduced pressure to give a yellow syrup. The crude product was purified by chromatography on silica eluting with a solvent gradient of 0 to 35% ethyl acetate in hexanes to give 2-(5-(tert-butyl)-2-methoxyphenyl)-5-methylpyridine (1.216 g, 99% yield) as a colorless oil.

HPLC/MS $R_t$=2.58 min, m/z 256.1 (M+H$^+$).

Step 2: 4-(tert-Butyl)-2-(5-methylpyridin-2-yl)phenol

To a solution of 2-(5-(tert-butyl)-2-methoxyphenyl)-5-methylpyridine (1.216 g, 4.76 mmol) in dry dichloromethane (50 mL) at 0° C. under nitrogen was added dropwise a solution of boron tribromide in dichloromethane (1.0 M, 9.52 mL, 9.52 mmol) and the reaction mixture stirred at 0° C. to room temperature for 5 hours. The reaction mixture was then re-cooled to 0° C., methanol (50 mL) added dropwise and the mixture then stirred at 40° C. for 18 hours. The reaction mixture was concentrated under reduced pressure, the residue re-dissolved in methanol (100 mL) and re-concentrated to afford a pink solid. Saturated aqueous sodium hydrogen carbonate solution (80 mL) was added and the resulting suspension extracted with ethyl acetate (80 mL). The organic phase separated, washed with water (80 mL) and saturated brine (80 mL), dried (MgSO$_4$), filtered and concentrated under reduced pressure to give a yellow syrup. The crude product was purified by chromatography on silica eluting with a solvent gradient of 0 to 15% ethyl acetate in hexanes to give 4-(tert-butyl)-2-(5-methylpyridin-2-yl)phenol (1.062 g, 92% yield) as a yellow syrup.

HPLC/MS $R_t$=7.08 min, m/z 242 (M+H$^+$).

Step 3: 4-(tert-Butyl)-2-((tert-butylamino)methyl)-6-(5-methylpyridin-2-yl)phenol dihydrochloride A mixture of paraformaldehyde (661 mg, 22.0 mmol) and tert-butylamine (2.32 mL, 22.0 mmol) in isopropanol (10 mL) was gently refluxed under nitrogen for 1 hour. A solution of 4-(tert-butyl)-2-(5-methylpyridin-2-yl)phenol (1.062 g, 4.4 mmol) in isopropanol (5 mL) was added and the reaction mixture refluxed for 6 days. The cooled reaction mixture was then concentrated under reduced pressure and the residue partitioned between ethyl acetate (80 mL) and 1.0 M aqueous sodium hydroxide solution (80 mL). The organic phase was separated, washed with water (80 mL) and saturated brine (80 mL), dried (MgSO$_4$), filtered and concentrated under reduced pressure to give a yellow syrup. The crude 3,4-dihydro-2H-benzo[e][1,3]oxazine was dissolved in absolute ethanol (90 mL), 1.0 M aqueous hydrochloric acid solution (30 mL) added and the reaction mixture stirred at room temperature for 9 days. The reaction mixture was concentrated under reduced pressure to remove ethanol, the resulting aqueous solution diluted to 50 mL with 1.0 M aqueous hydrochloric acid solution and washed with ethyl acetate (50 mL). The aqueous phase was basified to pH 7-8 by the addition of solid sodium carbonate and the resulting milky suspension extracted with ethyl acetate (80 mL). The organic phase was separated, washed with half saturated brine (80 mL), dried (MgSO$_4$), filtered and concentrated under reduced pressure to give a yellow syrup. The product was dissolved in absolute ethanol (50 mL), hydrogen chloride-ethanol solution (1.25 M, 18.44 mL, 23.05 mmol) added, the mixture stood for 20 minutes then concentrated under reduced pressure to give a cream solid. Diethyl ether (50 mL) and absolute ethanol (15 mL) were added and the resulting suspension stirred vigorously overnight then filtered to give 4-(tert-butyl)-2-((tert-butylamino)methyl)-6-(5-methylpyridin-2-yl)phenol dihydrochloride (1.466 g, 83% yield) as a hygroscopic white solid.

HPLC/MS $R_t$=4.39 min, m/z 327.2 (M+H$^+$); analysis calculated for $C_{21}H_{30}N_2O$ 2HCl 1.4H$_2$O: C, 59.40; H, 8.26; N, 6.60; Cl, 16.70. found: C, 59.25; H, 8.40; N, 6.54; Cl, 16.72.

Example 26

4-(tert-Butyl)-2-((tert-butylamino)methyl)-6-(5-fluoropyridin-2-yl)phenol 1.35hydrochloride

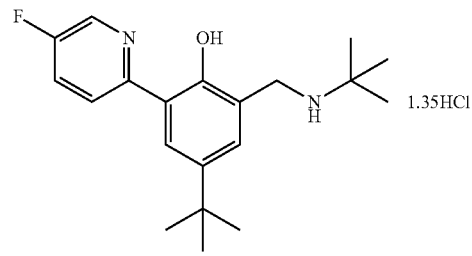

Step 1: 2-(5-(tert-Butyl)-2-methoxyphenyl)-5-fluoropyridine was prepared as a colorless syrup using the procedure described in Example 25, Step 1, replacing 2-bromo-5-methylpyridine with 2-bromo-5-fluoropyridine [purchased from TCI].

HPLC/MS $R_t$=7.06 min, m/z 260.1 (M+H$^+$).

Step 2: 4-(tert-Butyl)-2-(5-fluoropyridin-2-yl)phenol was prepared as a cream crystalline solid using the procedure described in Example 25, Step 2.

HPLC/MS $R_t$=7.32 min, m/z 246.1 (M+H$^+$).

Step 3: 4-(tert-Butyl)-2-((tert-butylamino)methyl)-6-(5-fluoropyridin-2-yl)phenol 1.35hydrochloride was prepared as a hygroscopic white solid using the procedure described in Example 25, Step 3.

HPLC/MS $R_t$=3.88 min, m/z 331.2 (M+H$^+$); analysis calculated for $C_{20}H_{22}FN_2O$ 1.35HCl 0.3H$_2$O: C, 62.38; H, 7.58; N, 7.27; Cl, 12.43. found: C, 62.20; H, 7.58; N, 7.21; Cl, 12.32.

Example 27

4-(tert-Butyl)-2-((tert-butylamino)methyl)-6-(3-fluoropyridin-2-yl)phenol 1.7hydrochloride

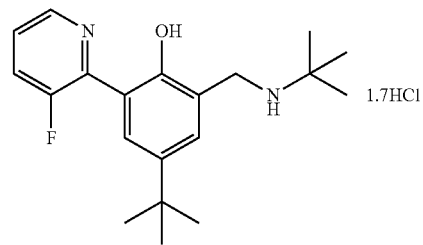

Step 1: 2-(5-(tert-Butyl)-2-methoxyphenyl)-3-fluoropyridine was prepared as a yellow syrup using the procedure described in Example 25, Step 1, replacing 2-bromo-5-methylpyridine with 2-bromo-3-fluoropyridine [purchased from TCI].

HPLC/MS $R_t$=6.25 min, m/z 260.1 (M+H$^+$).

Step 2: 4-(tert-Butyl)-2-(3-fluoropyridin-2-yl)phenol was prepared as a cream crystalline solid using the procedure described in Example 25, Step 2.

HPLC/MS $R_t$=7.22 min, m/z 246.1 (M+H$^+$).

Step 3: 4-(tert-Butyl)-2-((tert-butylamino)methyl)-6-(3-fluoropyridin-2-yl)phenol 1.7hydrochloride was prepared as a white solid using the procedure described in Example 25, Step 3.

HPLC/MS $R_t$=3.89 min, m/z 331.2 (M+H$^+$); analysis calculated for $C_{20}H_{27}FN_2O$ 1.7HCl: C, 61.21; H, 7.37; N, 7.14; Cl, 15.36. found: C, 61.38; H, 7.11; N, 7.11; Cl, 15.47.

Example 28

4-(tert-Butyl)-2-((tert-butylamino)methyl)-6-(4-(trifluoromethyl)pyridin-2-yl)phenol hydrochloride

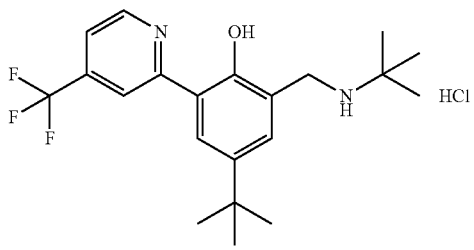 [SMILES: CC(C)(C)NCc1cc(C(C)(C)C)cc(-c2cc(C(F)(F)F)ccn2)c1O ; Cl]

Step 1: 2-(5-(tert-Butyl)-2-methoxyphenyl)-4-(trifluoromethyl)pyridine was prepared as a colorless syrup using the procedure described in Example 25, Step 1, replacing 2-bromo-5-methylpyridine with 2-bromo-4-(trifluoromethyl)pyridine [purchased from Oakwood].

HPLC/MS $R_t$=8.08 min, m/z 310.1 (M+H$^+$).

Step 2: 4-(tert-Butyl)-2-(4-(trifluoromethyl)pyridin-2-yl)phenol was prepared as a cream crystalline solid using the procedure described in Example 25, Step 2.

HPLC/MS $R_t$=8.06 min, m/z 296.1 (M+H$^+$).

Step 3: 4-(tert-Butyl)-2-((tert-butylamino)methyl)-6-(4-(trifluoromethyl)pyridin-2-yl)phenol hydrochloride was prepared as a yellow solid using the procedure described in Example 25, Step 3.

HPLC/MS $R_t$=4.43 min, m/z 381.1 (M+H$^+$); analysis calculated for $C_{21}H_{27}F_3N_2O$ HCl: C, 60.50; H, 6.77; N, 6.72; Cl, 8.50. found: C, 60.04; H, 6.56; N, 6.65; Cl, 8.53.

Example 29

4-(tert-Butyl)-2-((tert-butylamino)methyl)-6-(6-(trifluoromethyl)pyridin-2-yl)phenol hydrochloride

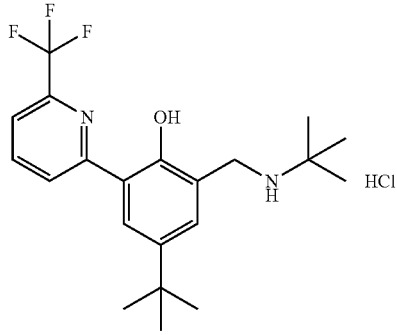

Step 1: 2-(5-(tert-Butyl)-2-methoxyphenyl)-6-(trifluoromethyl)pyridine was prepared as a white crystalline solid using the procedure described in Example 25, Step 1, replacing 2-bromo-5-methylpyridine with 2-bromo-6-(trifluoromethyl)pyridine [purchased from Combi-Blocks].

HPLC/MS $R_t$=8.17 min, m/z 310.1 (M+H$^+$).

Step 2: 4-(tert-Butyl)-2-(6-(trifluoromethyl)pyridin-2-yl)phenol was prepared as a yellow solid using the procedure described in Example 25, Step 2.

HPLC/MS $R_t$=8.01 min, m/z 296.1 (M+H$^+$).

Step 3: 4-(tert-Butyl)-2-((tert-butylamino)methyl)-6-(6-(trifluoromethyl)pyridin-2-yl)phenol hydrochloride was prepared as a white solid using the procedure described in Example 25, Step 3.

HPLC/MS $R_t$=4.50 min, m/z 381.2 (M+H$^+$); analysis calculated for $C_{21}H_{27}F_3N_2O$ HCl: C, 60.50; H, 6.77; N, 6.72; Cl, 8.50. found: C, 60.56; H, 6.71; N, 6.69; Cl, 8.58.

Example 30

4-(tert-Butyl)-2-((tert-butylamino)methyl)-6-(6-methylpyridin-3-yl)phenol dihydrochloride

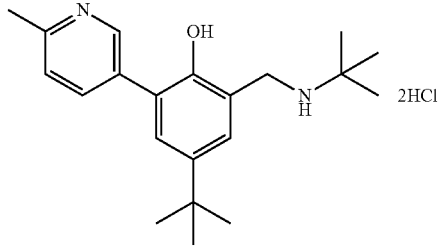 [SMILES: Cc1ccc(-c2cc(C(C)(C)C)cc(CNC(C)(C)C)c2O)cn1 ; "2HCl"]

Step 1: 2 5-(5-(tert-Butyl)-2-methoxyphenyl)-2-methylpyridine was prepared as a yellow oil using the procedure described in Example 25, Step 1, replacing 2-bromo-5-methylpyridine with 5-bromo-2-picoline.

HPLC/MS $R_t$=2.88 min, m/z 256.1 (M+H$^+$).

Step 2: 4-(tert-Butyl)-2-(6-methylpyridin-3-yl)phenol was prepared as a colorless syrup using the procedure described in Example 25, Step 2.

HPLC/MS $R_t$=1.69 min, m/z 242.1 (M+H$^+$).

Step 3: 4-(tert-Butyl)-2-((tert-butylamino)methyl)-6-(6-methylpyridin-3-yl)phenol dihydrochloride was prepared as a white solid using the procedure described in Example 25, Step 3.

HPLC/MS $R_t$=1.10 min, m/z 327.2 (M+H$^+$); analysis calculated for $C_{21}H_{30}N_2O$ 2HCl: C, 63.15; H, 8.08; N, 7.01; Cl, 17.75. found: C, 63.30; H, 8.04; N, 6.75; Cl, 17.90.

Example 31

4-(tert-Butyl)-2-((tert-butylamino)methyl)-6-(3-(trifluoromethyl)pyridin-2-yl)phenol 1.7hydrochloride

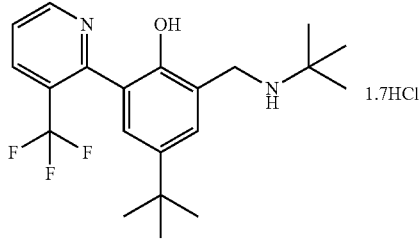

Step 1: 2-(5-(tert-Butyl)-2-methoxyphenyl)-3-(trifluoromethyl)pyridine was prepared as a yellow oil using the procedure described in Example 25, Step 1, replacing 2-bromo-5-methylpyridine with 2-bromo-3-(trifluoromethyl)pyridine [purchased from TCI].

HPLC/MS $R_t$=6.90 min, m/z 310.1 (M+H$^+$).

Step 2: 4-(tert-Butyl)-2-(3-(trifluoromethyl)pyridin-2-yl)phenol was prepared as a yellow solid using the procedure described in Example 25, Step 2.

HPLC/MS $R_t$=6.01 min, m/z 296.1 (M+H$^+$).

Step 3: 4-(tert-Butyl)-2-((tert-butylamino)methyl)-6-(3-(trifluoromethyl)pyridin-2-yl)phenol 1.7hydrochloride was prepared as a cream solid using the procedure described in Example 25, Step 3.

HPLC/MS $R_t$=3.80 min, m/z 381.2 (M+H$^+$); analysis calculated for $C_{21}H_{27}F_3N_2O$ 1.7HCl: C, 57.01; H, 6.54; N, 6.33; Cl, 13.62. found: C, 56.64; H, 6.37; N, 6.25; Cl, 13.71.

Example 32

4-(tert-Butyl)-2-((tert-butylamino)methyl)-6-(5-(trifluoromethyl)pyrazin-2-yl)phenol hydrochloride

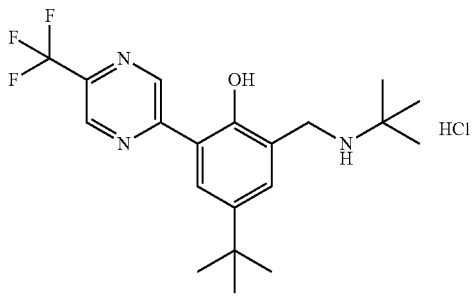 [SMILES: CC(C)(C)NCc1cc(C(C)(C)C)cc(-c2cnc(C(F)(F)F)cn2)c1O ; Cl]

Step 1: 2-(5-(tert-Butyl)-2-methoxyphenyl)-5-(trifluoromethyl)pyrazine was prepared as a white crystalline solid using the procedure described in Example 25, Step 1, replacing 2-bromo-5-methylpyridine with 2-chloro-5-(trifluoromethyl)pyrazine [purchased from Matrix Scientific].

HPLC/MS $R_t$=8.07 min, m/z 311.1 (M+H$^+$).

Step 2: 4-(tert-butyl)-2-(5-(trifluoromethyl)pyrazin-2-yl)phenol was prepared as a yellow crystalline solid using the procedure described in Example 25, Step 2.

HPLC/MS $R_t$=7.59 min, m/z 297.1 (M+H$^+$).

Step 3: 4-(tert-Butyl)-2-((tert-butylamino)methyl)-6-(5-(trifluoromethyl)pyrazin-2-yl)phenol hydrochloride was prepared as a cream solid using the procedure described in Example 25, Step 3.

HPLC/MS $R_t$=4.56 min, m/z 382.3 (M+H$^+$); analysis calculated for $C_{20}H_{26}F_3N_3O$ HCl: C, 57.48; H, 6.51; N, 10.06; Cl, 8.48. found: C, 57.62; H, 6.31; N, 10.04; Cl, 8.58.

Example 33

4-(tert-Butyl)-2-((tert-butylamino)methyl)-6-(2-(trifluoromethyl)pyrimidin-5-yl)phenol hydrochloride

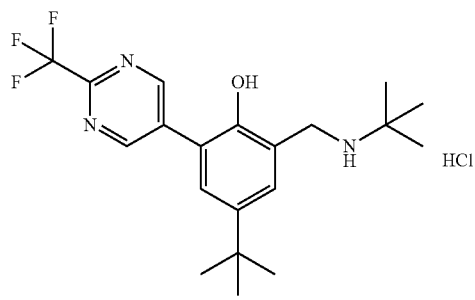 [SMILES: CC(C)(C)NCc1cc(C(C)(C)C)cc(-c2cnc(C(F)(F)F)nc2)c1O ; Cl]

Step 1: 5-(5-(tert-Butyl)-2-methoxyphenyl)-2-(trifluoromethyl)pyrimidine was prepared as a white crystalline solid using the procedure described in Example 25, Step 1, replacing 2-bromo-5-methylpyridine with 5-bromo-2-(trifluoromethyl)pyrimidine [purchased from Matrix Scientific].

HPLC/MS $R_t$=7.80 min, m/z 311.1 (M+H$^+$).

Step 2: 4-(tert-Butyl)-2-(2-(trifluoromethyl)pyrimidin-5-yl)phenol was prepared as a white crystalline solid using the procedure described in Example 25, Step 2.

HPLC/MS $R_t$=6.59 min, m/z 297.1 (M+H$^+$).

Step 3: 4-(tert-Butyl)-2-((tert-butylamino)methyl)-6-(2-(trifluoromethyl)pyrimidin-5-yl)phenol hydrochloride was prepared as a white solid using the procedure described in Example 25, Step 3.

HPLC/MS $R_t$=3.72 min, m/z 382.3 (M+H$^+$); analysis calculated for $C_{20}H_{26}F_3N_3O$ HCl 0.3H$_2$O: C, 56.75; H, 6.57; N, 9.93; Cl, 8.38. found: C, 56.60; H, 6.66; N, 9.63; Cl, 8.38.

Example 34

4-(tert-Butyl)-2-((tert-butylamino)methyl)-6-(5-fluoro-6-(trifluoromethyl)pyridin-3-yl)phenol hydrochloride

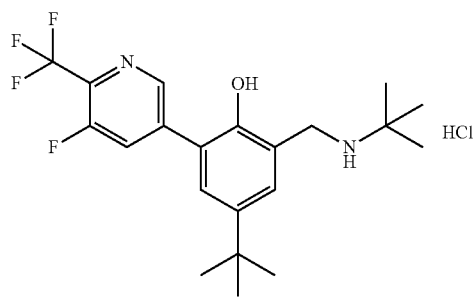 [SMILES: CC(C)(C)NCc1cc(C(C)(C)C)cc(-c2cnc(C(F)(F)F)c(F)c2)c1O ; Cl]

Step 1: 5-(5-(tert-Butyl)-2-methoxyphenyl)-3-fluoro-2-(trifluoromethyl)pyridine was prepared as a white solid using the procedure described in Example 25, Step 1, replacing 2-bromo-5-methylpyridine with 5-bromo-3-fluoro-2-(trifluoromethyl)pyridine [purchased from Matrix Scientific].

HPLC/MS $R_t$=8.44 min, m/z 328.1 (M+H$^+$).

Step 2: 4-(tert-Butyl)-2-(5-fluoro-6-(trifluoromethyl)pyridin-3-yl)phenol was prepared as a tan solid using the procedure described in Example 25, Step 2.

HPLC/MS $R_t$=7.22 min, m/z 314.1 (M+H$^+$).

Step 3: 4-(tert-Butyl)-2-((tert-butylamino)methyl)-6-(5-fluoro-6-(trifluoromethyl)pyridin-3-yl)phenol hydrochloride was prepared as a white solid using the procedure described in Example 25, Step 3.

HPLC/MS $R_t$=4.24 min, m/z 399.2 (M+H$^+$); analysis calculated for $C_{21}H_{26}F_4N_2O$ HCl: C, 58.00; H, 6.26; N, 6.44; Cl, 8.15. found: C, 58.19; H, 6.11; N, 6.43; Cl, 8.39.

Example 35

4-(tert-Butyl)-2-((tert-butylamino)methyl)-6-(3-(trifluoromethyl)pyridin-4-yl)phenol dihydrochloride

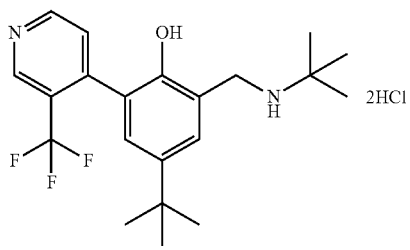 [SMILES: CC(C)(C)NCc1cc(C(C)(C)C)cc(-c2ccncc2C(F)(F)F)c1O]

Step 1: 4-(5-(tert-Butyl)-2-methoxyphenyl)-3-(trifluoromethyl)pyridine was prepared as a colorless oil using the procedure described in Example 25, Step 1, replacing 2-bromo-5-methylpyridine with 4-bromo-3-(trifluoromethyl)pyridine hydrobromide [purchased from Matrix Scientific].

HPLC/MS $R_t$=7.23 min, m/z 310.1 (M+H$^+$).

Step 2: 4-(tert-Butyl)-2-(3-(trifluoromethyl)pyridin-4-yl)phenol was prepared as a light tan crystalline solid using the procedure described in Example 25, Step 2.

HPLC/MS $R_t$=5.95 min, m/z 296.1 (M+H$^+$).

Step 3: 4-(tert-Butyl)-2-((tert-butylamino)methyl)-6-(3-(trifluoromethyl)pyridin-4-yl)phenol dihydrochloride was prepared as a white solid using the procedure described in Example 25, Step 3.

HPLC/MS $R_t$=3.42 min, m/z 381.2 (M+H$^+$); analysis calculated for $C_{21}H_{27}F_3N_2O$ 2HCl: C, 55.63; H, 6.45; N, 6.18; Cl, 15.64. found: C, 55.74; H, 6.47; N, 6.22; Cl, 15.62.

Example 36

4-(tert-Butyl)-2-((tert-butylamino)methyl)-6-(4-(trifluoromethyl)pyridin-3-yl)phenol 1.9hydrochloride

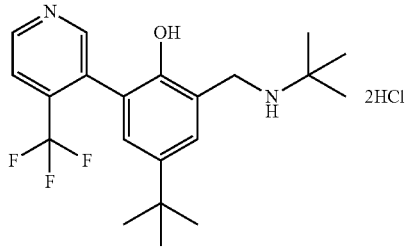 [SMILES: CC(C)(C)NCc1cc(C(C)(C)C)cc(-c2cnccc2C(F)(F)F)c1O]

Step 1: 3-(5-(tert-Butyl)-2-methoxyphenyl)-4-(trifluoromethyl)pyridine was prepared as a colorless oil using the procedure described in Example 25, Step 1, replacing 2-bromo-5-methylpyridine with 3-bromo-4-(trifluoromethyl)pyridine [purchased from Matrix Scientific].

HPLC/MS $R_t$=7.31 min, m/z 310.1 (M+H$^+$).

Step 2: 4-(tert-Butyl)-2-(4-(trifluoromethyl)pyridin-3-yl)phenol was prepared as a tan crystalline solid using the procedure described in Example 25, Step 2.

HPLC/MS $R_t$=5.99 min, m/z 296.1 (M+H$^+$).

Step 3: 4-(tert-Butyl)-2-((tert-butylamino)methyl)-6-(4-(trifluoromethyl)pyridin-3-yl)phenol 1.9hydrochloride was prepared as a white solid using the procedure described in Example 25, Step 3.

HPLC/MS $R_t$=3.91 min, m/z 381.2 (M+H$^+$); analysis calculated for $C_{21}H_{27}F_3N_2O$ 1.9HCl: C, 56.08; H, 6.48; N, 6.23; Cl, 14.98. found: C, 55.92; H, 6.30; N, 6.22; Cl, 14.58.

Example 37

2-((tert-Butylamino)methyl)-4,6-di(pyridin-3-yl)phenol

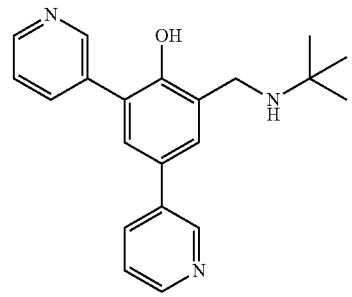 [SMILES: CC(C)(C)NCc1cc(-c2cccnc2)cc(-c2cccnc2)c1O]

A mixture of 6,8-dibromo-3-(tert-butyl)-3,4-dihydro-2H-benzo[e][1,3]oxazine (Intermediate 6) (0.621 g, 1.79 mmol), pyridine-3-boronic acid [purchased from Boron Molecular Limited] (0.660 g, 5.37 mmol) and potassium carbonate (1.979 g, 14.3 mmol) in 2-propanol (30 mL) and water (6 mL) was purged with nitrogen for 20 minutes. Tetrakis(triphenylphosphine)Pd (0) (107 mg, 0.09 mmol) was added and the resulting mixture was heated at 72° C. for 30 minutes then the cooled reaction mixture concentrated under reduced pressure. The residue was dissolved in ethyl acetate, washed with water, dried (MgSO$_4$), filtered and concentrated under reduced pressure to afford a dark brown oil. The product was purified by flash chromatography on silica eluting with a solvent gradient of 0 to 30% ethyl acetate in hexanes to give 2-((tert-butylamino)methyl)-4,6-di(pyridine-3-yl)phenol (151 mg) as an off-white solid.

HPLC/MS $R_t$=3.05 min, m/z 334.1 (M+H$^+$).

Example 38

2-((tert-Butylamino)methyl)-4,6-bis(6-(trifluoromethyl)pyridin-3-yl)phenol

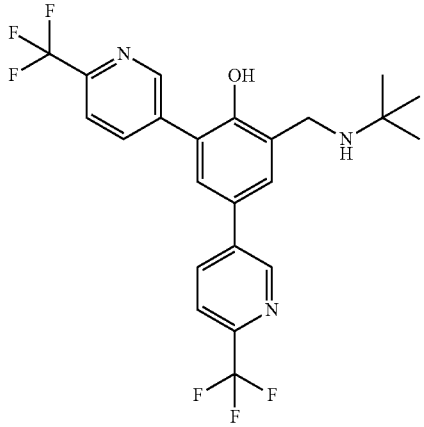 [SMILES: CC(C)(C)NCc1cc(-c2ccc(C(F)(F)F)nc2)cc(-c2ccc(C(F)(F)F)nc2)c1O]

A mixture of 6,8-dibromo-3-(tert-butyl)-3,4-dihydro-2H-benzo[e][1,3]oxazine (Intermediate 6) (0.621 g, 1.79 mmol), 6-(trifluoromethyl)pyridine-3-boronic acid [purchased from Frontier Scientific] (1.025 g, 5.37 mmol), and potassium carbonate (1.979 g, 14.3 mmol) in 2-propanol (30 mL) and water (6 mL) was purged with nitrogen for 20 minutes. Tetrakis(triphenylphosphine)palladium (0) (114 mg, 0.099 mmol) was added and the resulting mixture heated at 72° C. for 60 minutes then the cooled reaction mixture concentrated under reduced pressure. The residue was dissolved in ethyl acetate, washed with water, dried (MgSO$_4$), filtered and concentrated under reduced pressure to afford a dark brown oil. The product was purified using flash chromatography on silica eluting with a solvent gradient of 0 to 30% ethyl acetate in hexanes to give a yellow solid. The solid was triturated with 1:1 v/v MTBE/hexane, filtered and then dried at 40° C./4-8 mm Hg to give 2-((tert-butylamino)methyl)-4,6-bis(6-(trifluoromethyl)pyridin-3-yl)phenol (0.358 g) as an off-white solid.

HPLC/MS $R_t$=10.30 min, m/z 470.1 (M+H$^+$).

Example 39

3-((tert-Butylamino)methyl)-4'-chloro-3'-(trifluoromethyl)-5-(6-(trifluoromethyl)pyridin-3-yl)-[1,1'-biphenyl]-4-ol hydrochloride

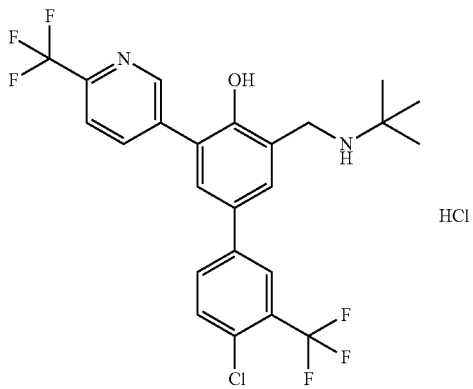 [SMILES: CC(C)(C)NCc1cc(-c2ccc(Cl)c(C(F)(F)F)c2)cc(-c2ccc(C(F)(F)F)nc2)c1O ; Cl]

Step 1: 8-Bromo-3-(tert-butyl)-6-(4-chloro-3-(trifluoromethyl)phenyl)-3,4-dihydro-2H-benzo[e][1,3]oxazine A mixture of 6,8-dibromo-3-(tert-butyl)-3,4-dihydro-2H-benzo[e][1,3]oxazine (Intermediate 6) (2.4 g, 6.92 mmol), (4-chloro-3-(trifluoromethyl)phenyl)boronic acid (1.628 g, 7.27 mmol), and potassium carbonate (1.434 g, 10.4 mmol) in 2-propanol (40 mL) and water (8 mL) was purged with nitrogen for 20 minutes. Tetrakis(triphenylphosphine)Pd (0) (336 mg, 0.29 mmol) was added and the resulting mixture heated at 72° C. for 3 h then the cooled reaction mixture concentrated under reduced pressure. The residue was dissolved in ethyl acetate, washed with water, dried (MgSO$_4$), filtered and concentrated under reduced pressure to give a solid that was re-crystallized from ethyl acetate to give 8-bromo-3-(tert-butyl)-6-(4-chloro-3-(trifluoromethyl)phenyl)-3,4-dihydro-2H-benzo[e][1,3]oxazine (0.625 g).

HPLC/MS $R_t$=12.51 min, m/z 436.0 (M+H$^+$ of the hydrolyzed product).

Step 2: 3-((tert-Butylamino)methyl)-4'-chloro-3'-(trifluoromethyl)-5-(6-(trifluoromethyl)pyridin-3-yl)-[1,1'-biphenyl]-4-ol hydrochloride A mixture of 8-bromo-3-(tert-butyl)-6-(4-chloro-3-(trifluoromethyl)phenyl)-3,4-dihydro-2H-benzo[e][1,3]oxazine (0.5 g, 1.12 mmol), 6-(trifluoromethyl)pyridine-3-boronic acid [purchased from Frontier Scientific] (0.224 g, 1.17 mmol), and potassium carbonate (0.232 g, 1.68 mmol) in 2-propanol (20 mL) and water (4 mL) was purged with nitrogen for 20 minutes. Tetrakis(triphenylphosphine)Pd (0) (64.6 mg, 0.056 mmol) was added and the resulting mixture was heated at 72° C. for 5 h then the cooled reaction mixture concentrated under reduced pressure. The residue was dissolved in ethyl acetate, washed with water, dried (MgSO$_4$), filtered and concentrated under reduced pressure to give a yellow solid. The crude product was purified using flash chromatography on silica eluting with a solvent gradient of 0 to 30% ethyl acetate in hexanes to give 0.163 g of product as a yellow solid. The solid was dissolved in ethyl acetate, and the resulting solution was treated with 37% hydrochloric acid (0.05 g). The solid product was collected by filtration and rinsed with ethyl acetate to give 3-((tert-butylamino)methyl)-4'-chloro-3'-(trifluoromethyl)-5-(6-(trifluoromethyl)pyridin-3-yl)-[1,1'-biphenyl]-4-ol hydrochloride (0.135 g) as a white powder.

HPLC/MS $R_t$=14.01 min, m/z 503.1 (M+H$^+$).

Example 40

4-(tert-Butyl)-2-((tert-butylamino)methyl)-6-(5-(trifluoromethyl)pyridin-2-yl)phenol

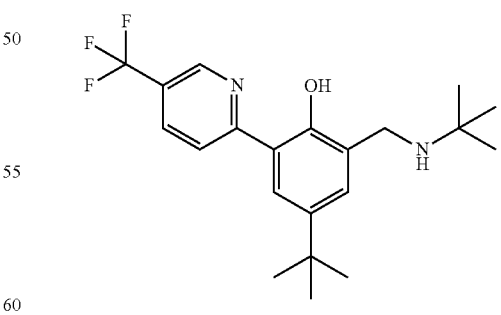

Step 1: 4-(tert-Butyl)-2-(5-(trifluoromethyl)pyridin-2-yl)phenol

A mixture of 2-(benzyloxy)-5-(tert-butyl)phenylboronic acid (1.0 g, 3.52 mmol), 2-bromo-5-(trifluoromethyl)pyridine (0.80 g, 3.54 mmol) and potassium carbonate (1 g, 7.24 mmol) in DME (20 mL) and water (5 mL) was purged with nitrogen for 20 minutes. Tetrakis(triphenylphosphine)Pd (0) (200.0 mg, 0.17 mmol) was added and the mixture heated at 80° C. overnight. The cooled reaction mixture was extracted with ethyl acetate (50 mL), the organic phase separated, dried (MgSO₄), filtered and concentrated under reduced pressure. The product was purified using flash chromatography on silica eluting with 30% ethyl acetate in hexanes to give the benzyl ether intermediate. A solution of the benzyl ether in ethanol (20 mL) was added to 5% palladium on carbon (100 mg) and the mixture hydrogenated overnight. The reaction mixture was then filtered and concentrated under reduced pressure to give 4-(tert-butyl)-2-(5-(trifluoromethyl)pyridin-2-yl)phenol.

MS m/z 296.1 (M+H⁺).

Step 2: 4-(tert-Butyl)-2-((tert-butylamino)methyl)-6-(5-(trifluoromethyl)pyridin-2-yl)phenol was prepared as a white solid using the same procedure as described in Example 25, Step 3, replacing 4-(tert-butyl)-2-(5-methylpyridin-2-yl)phenol with 4-(tert-butyl)-2-(5-(trifluoromethyl)pyridin-2-yl)phenol.

MS m/z 381.1 (M+H⁺); ¹H NMR (400 MHz, DMSO-d₆) δ 9.1 (s, 1H), 8.7 (br s, 1H), 8.6 (dd, 1H), 8.4 (dd, 1H), 8.09 (s, 1H), 7.7 (s, 1H), 4.1 (br s, 2H), 1.4 (s, 9H), and 1.3 (s, 9H).

Example 41

4-(tert-Butyl)-2-((tert-butylamino)methyl)-6-(5,6-dichloropyridin-3-yl)phenol hydrochloride

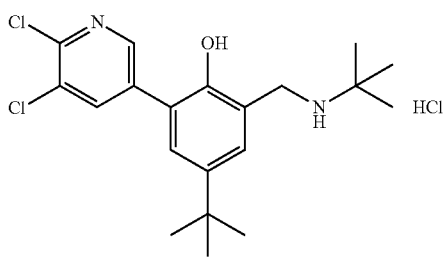 [SMILES: CC(C)(C)NCc1cc(C(C)(C)C)cc(-c2cnc(Cl)c(Cl)c2)c1O ; Cl]

Step 1: 4-(tert-Butyl)-2-(5,6-dichloropyridin-3-yl)phenol

A mixture of 5-(tert-butyl)-2-((2-methoxyethoxy)methoxy)benzeneboronic acid (Intermediate 7) (1.0 g, 3.54 mmol), 5-bromo-2,3-dichloropyridine (0.80 g, 3.53 mmol) and potassium carbonate (1.5 g, 10.85 mmol) in DME (20 mL) and water (5 mL) was purged with nitrogen for 20 minutes. Tetrakis(triphenylphosphine)palladium (0) (200.0 mg, 0.17 mmol) was added and the mixture heated at 80° C. overnight. The cooled reaction mixture was extracted with ethyl acetate (50 mL), the organic phase separated, dried (MgSO₄), filtered and concentrated under reduced pressure. The product was purified using flash chromatography on silica eluting with 30% ethyl acetate in hexanes to give the MEM ether intermediate. The MEM ether was stirred in 10% hydrochloric acid in ethanol at room temperature for 4 hours. The reaction mixture was then concentrated under reduced pressure to give 4-(tert-butyl)-2-(5,6-dichloropyridin-3-yl)phenol.

Step 2: 4-(tert-Butyl)-2-((tert-butylamino)methyl)-6-(5,6-dichloropyridin-3-yl)phenol hydrochloride was prepared as a white solid using the same procedure as described in Example 25, Step 3, replacing 4-(tert-butyl)-2-(5-methylpyridin-2-yl)phenol with 4-(tert-butyl)-2-(5,6-dichloropyridin-3-yl)phenol.

Mpt. 214-216° C.; ¹H NMR (400 MHz, DMSO-d₆) δ 9.2 (s, 1H), 8.7 (br s, 2H), 8.5 (dd, 1H), 8.2 (dd, 1H), 7.6 (dd, 1H), 7.4 (dd, 1H), 4.1 (m, 2H), 1.4 (s, 9H), and 1.2 (s, 9H).

Example 42

4-(tert-Butyl)-2-((tert-butylamino)methyl)-6-(6-cyclopropylpyridin-3-yl)phenol hydrochloride

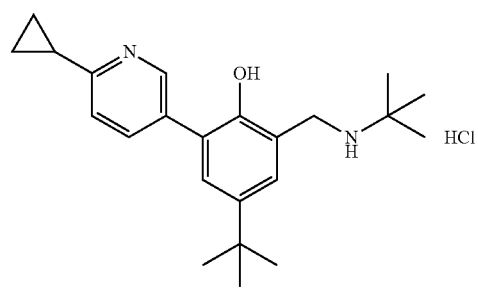 [SMILES: CC(C)(C)NCc1cc(C(C)(C)C)cc(-c2ccc(C3CC3)nc2)c1O ; Cl]

Step 1: 4-(tert-Butyl)-2-(6-cyclopropylpyridin-3-yl)phenol was prepared as a white solid using the same procedure as described in Example 41, Step 1, replacing 5-bromo-2,3-dichloropyridine with 5-bromo-2-cyclopropylpyridine.

Step 2: 4-(tert-Butyl)-2-((tert-butylamino)methyl)-6-(6-cyclopropylpyridin-3-yl)phenol hydrochloride was prepared as a white solid using the same procedure as described in Example 25, Step 3, replacing 4-(tert-butyl)-2-(5-methylpyridin-2-yl)phenol with 4-(tert-butyl)-2-(6-cyclopropylpyridin-3-yl)phenol.

Example 43

4-(tert-Butyl)-2-((tert-butylamino)methyl)-6-(6-(methylsulfonyl)pyridin-3-yl)phenol hydrochloride

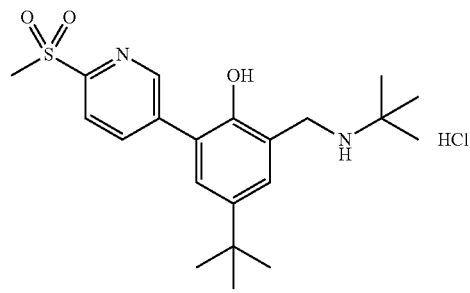 [SMILES: CC(C)(C)NCc1cc(C(C)(C)C)cc(-c2ccc(S(C)(=O)=O)nc2)c1O ; Cl]

The title compound was prepared as a white solid using the procedure described in Example 1 from 8-bromo-3,6-di-tert-butyl-3,4-dihydro-2H-benzo[e][1,3]oxazine (Intermediate 1) and 2-methylsulfonylpyridine-5-boronic acid pinacol ester [purchased from Combi-Blocks].

HPLC/MS R_t=1.7 min, m/z 391.1 (M+H⁺); mpt. 229-232° C.

Example 44

4-(tert-Butyl)-2-((tert-butylamino)methyl)-6-(5-chloro-6-(trifluoromethyl)pyridin-3-yl)phenol hydrochloride

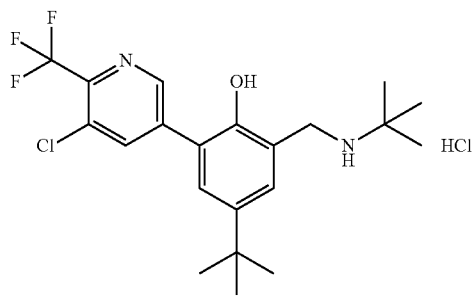 [SMILES: CC(C)(C)NCc1cc(C(C)(C)C)cc(-c2cnc(C(F)(F)F)c(Cl)c2)c1O ; Cl]

Step 1: 4-(tert-Butyl)-2-(5-chloro-6-(trifluoromethyl)pyridin-3-yl)phenol was prepared as a white solid using the same procedure as described in Example 41, Step 1, replacing 5-bromo-2,3-dichloropyridine with 5-bromo-3-chloro-2-(trifluoromethyl)pyridine.

Step 2: 4-(tert-Butyl)-2-((tert-butylamino)methyl)-6-(5-chloro-6-(trifluoromethyl)pyridin-3-yl)phenol hydrochloride was prepared as a white solid using the same procedure as described in Example 25, Step 3, replacing 4-(tert-butyl)-2-(5-methylpyridin-2-yl)phenol with 4-(tert-butyl)-2-(5-chloro-6-(trifluoromethyl)pyridin-3-yl)phenol.

Mpt. 230-233° C.; $^1$H NMR (400 MHz, DMSO-d$_6$) δ 9.36 (s, 1H), 8.8 (s, 1H), 8.6 (br s, 1H), 8.5 (s, 1H), 7.6 (s, 1H), 7.4 (s, 1H), 4.1 (br s, 2H), 1.4 (s, 9H), and 1.2 (s, 9H).

Example 45

4-(tert-Butyl)-2-((tert-butyl(methyl)amino)methyl)-6-(6-(trifluoromethyl)pyridin-3-yl)phenol hydrochloride

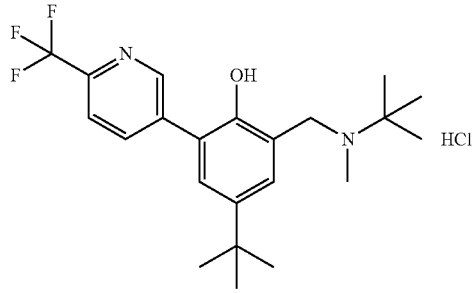 [SMILES: CN(Cc1cc(C(C)(C)C)cc(-c2ccc(C(F)(F)F)nc2)c1O)C(C)(C)C ; Cl]

Trifluoroacetic acid (2 mL) was added to a solution of 4-(tert-butyl)-2-((tert-butylamino)methyl)-6-(6-(trifluoromethyl)pyridin-3-yl)phenol [Example 1, free base] (500 mg, 1.32 mmol) in dichloromethane (6 mL) and the mixture stirred at 25° C. for one hour. The solvent was removed under reduced pressure, the residue was dissolved in toluene and re-concentrated under reduced pressure to yield the trifluoroacetate salt (652 mg, 100% yield). The trifluoroacetate salt was dissolved in a solution of methanol (7 mL) and dichloromethane (0.7 mL). The solution was cooled to 0° C. and a 2 M solution of diazomethane in ether (2 mL, 4 mmol) was added dropwise. The solution was allowed to warm to room temperature over 16 hours and the reaction was quenched by the addition of acetic acid (1 mL). The solvent was removed under reduced pressure and the residue was purified using two flash chromatography runs on silica eluting with a solvent gradient of 0 to 100% ethyl acetate in hexanes isolating the less polar of the two major TLC spots. The residue was dissolved in an excess of a 1N solution of hydrochloric acid in ethanol, the solvent was removed under reduced pressure and the solid triturated with ether to give 4-(tert-butyl)-2-((tert-butyl(methyl)amino)methyl)-6-(6-(trifluoromethyl)pyridin-3-yl)phenol hydrochloride (140 mg, 34% yield) as an off-white solid. HPLC/MS R$_t$=3.99 min, m/z 395.2 (M+H$^+$); $^1$H NMR (DMSO-d$_6$, 400 MHz) δ 9.27 (br s, 1H), 8.92 (d, J=1.5 Hz, 1H), 8.22 (dd, J=8.2 Hz, 1.5 Hz, 1H), 7.99 (d, J=8.2 Hz, 1H), 7.61 (m, 1H), 7.44 (d, J=2.3 Hz, 1H), 4.62 (br s, 1H), 4.01 (br s, 1H), 2.58 (br s, 3H), 1.48 (s, 9H), and 1.32 (s, 9H).

Example 46

4-(tert-Butyl)-2-((tert-butylamino)methyl)-6-(4-(trifluoromethyl)pyrimidin-2-yl)phenol hydrochloride

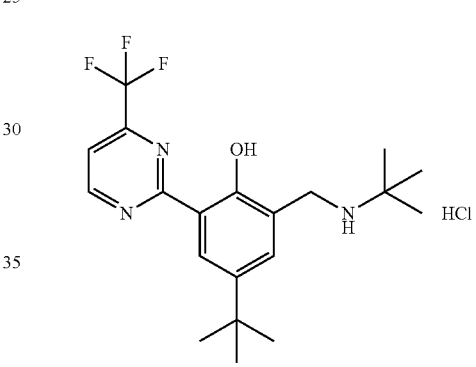

Step 1: 5-(tert-Butyl)-2-hydroxy-3-(4-(trifluoromethyl)pyrimidin-2-yl)benzaldehyde To a nitrogen de-gassed mixture of 3-bromo-5-(tert-butyl)-2-hydroxybenzaldehyde [CAS #119646-68-3] (1.00 g, 3.89 mmol), bis(pinacolato)diboron (1.98 g, 7.80 mmol), and potassium acetate (1.15 g, 11.7 mmol) in dioxane (50 mL) under a nitrogen was added [1,1'-bis(diphenylphosphino)ferrocene]dichloropalladium(II) complex with dichloromethane (285 mg, 0.39 mmol) and the reaction mixture heated to 85° C. for 16 hours. The reaction was allowed to cool to 25° C. at which time 2M aqueous sodium carbonate (9.7 mL, 19.5 mmol) and 2-chloro-4-trifluoromethylpyrimidine (1.42 g, 7.78 mmol) were added and the solution degassed with nitrogen. A second portion of [1,1'-bis(diphenylphosphino)ferrocene]dichloropalladium(II) complex with dichloromethane (285 mg, 0.39 mmol) was added and the mixture heated at 85° C. under a nitrogen atmosphere for 6 hours. The cooled reaction mixture was then partitioned between ethyl acetate (100 mL) and a saturated aqueous solution of sodium bicarbonate (100 mL). The organic phase was separated, concentrated under reduced pressure and purified using flash chromatography on silica eluting with a solvent gradient of 0 to 70% ethyl acetate in hexanes to give 5-(tert-butyl)-2-hydroxy-3-(4-(trifluoromethyl)pyrimidin-2-yl)benzaldehyde (350 mg, 28% yield) as a cream solid.

HPLC/MS R$_t$=7.68 min, m/z 325.1 (M+H$^+$).

Step 2: 4-(tert-Butyl)-2-((tert-butylamino)methyl)-6-(4-(trifluoromethyl)pyrimidin-2-yl)phenol hydrochloride To a solution of 5-(tert-butyl)-2-hydroxy-3-(4-(trifluoromethyl)pyrimidin-2-yl)benzaldehyde (324 mg, 1.00 mmol) and tert-butylamine (0.21 mL, 2.00 mmol) in methanol (10 mL) was added sodium triacetoxyborohydride (254 mg, 1.20 mmol). The solution was stirred at 25° C. for one hour at which time a second portion of sodium triacetoxyborohydride (254 mg, 1.20 mmol) was added. After one hour a third portion of sodium triacetoxyborohydride (254 mg, 1.20 mmol) was added and the mixture was stirred for one hour. The solution was brought to pH 1 by the addition of 1N solution of hydrochloric acid and then partitioned between ethyl acetate (25 mL) and saturated aqueous sodium bicarbonate solution (25 mL). The organic phase was separated, concentrated under reduced pressure and purified using flash chromatography on silica eluting with a solvent gradient of 100:0 to 0:100 v/v 100% dichloromethane to a solution of 10% methanol, 1% ammonium hydroxide, 89% dichloromethane. The product was further purified using flash chromatography on silica eluting with a solvent gradient of 0 to 100% acetone in hexanes. The residue was dissolved in an excess of a 1N solution of hydrochloric acid in ethanol, the solvent was removed under reduced pressure and the solid was triturated with ether to give 4-(tert-butyl)-2-((tert-butylamino)methyl)-6-(4-(trifluoromethyl)pyrimidin-2-yl)phenol hydrochloride (156 mg, 38% yield) as an off-white solid.

HPLC/MS $R_t$=4.70 min, m/z 382.3 (M+H$^+$); $^1$H nmr (DMSO-d$_6$, 400 MHz) δ 13.02 (s, 1H), 9.36 (d, J=5.1 Hz, 1H), 8.84 (br s, 1H), 8.47 (d, J=2.6 Hz, 1H), 8.10 (d, J=5.1 Hz, 1H), 7.95 (d, J=2.6 Hz, 1H), 4.20-4.13 (m, 2H), 1.41 (s, 9H), and 1.34 (s, 9H); analysis calculated for $C_{20}H_{26}F_3N_3O$·HCl: C, 57.48; H, 6.51; N, 10.06. found: C, 57.40; H, 6.67; N, 9.85.

Example 47

4-(tert-Butyl)-2-((diethylamino)methyl)-6-(6-(trifluoromethyl)pyridin-3-yl)phenol hydrochloride

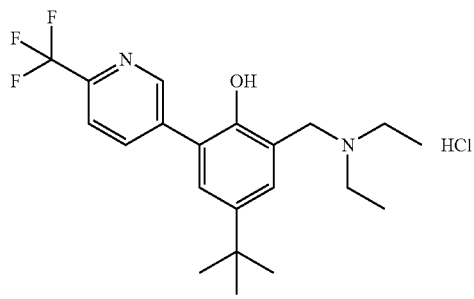 [SMILES: CCN(CC)Cc1cc(C(C)(C)C)cc(-c2ccc(C(F)(F)F)nc2)c1O ; Cl]

Step 1: 5-(tert-Butyl)-2-hydroxy-3-(6-(trifluoromethyl)pyridin-3-yl)benzaldehyde A mixture of 3-bromo-5-(tert-butyl)-2-hydroxybenzaldehyde (Intermediate 8) (1.0 g, 3.89 mmol), 2-(trifluoromethyl)pyridine-5-boronic acid [purchased from Frontier Scientific] (817 mg, 4.28 mmol) and potassium carbonate (1.34 g, 9.72 mmol) in DME (15 mL) and water (5 mL) was purged with nitrogen for 20 minutes.
Tetrakis(triphenylphosphine)palladium (0) (224.7 mg, 0.194 mmol) was added and the mixture heated at 80° C. in a sealed vial for 24 hours. The cooled reaction mixture was then partitioned between ethyl acetate (80 mL) and 1M aqueous hydrochloric acid (80 mL). The organic phase was separated, washed with water (80 mL) and saturated brine (80 mL), dried (MgSO$_4$), filtered and concentrated under reduced pressure to give a yellow syrup. The product was purified using flash chromatography on silica eluting with a solvent gradient of 0 to 10% ethyl acetate in hexanes to give 5-(tert-butyl)-2-hydroxy-3-(6-(trifluoromethyl)pyridin-3-yl)benzaldehyde (0.6904 g, 55% yield) as a yellow solid.

HPLC/MS $R_t$=7.54 min, m/z 324.1 (M+H$^+$).

Step 2: 4-(tert-Butyl)-2-((diethylamino)methyl)-6-(6-(trifluoromethyl)pyridin-3-yl)phenol hydrochloride Sodium triacetoxyborohydride (0.678 g, 3.20 mmol) was added to a solution of 5-(tert-butyl)-2-hydroxy-3-(6-(trifluoromethyl)pyridin-3-yl)benzaldehyde (0.69 g, 2.13 mmol), diethylamine (0.44 mL, 4.27 mmol) and acetic acid (0.12 mL, 2.13 mmol) in dichloroethane (10 mL) and the reaction mixture stirred at room temperature under nitrogen for 15½ hours. The reaction was quenched by the addition of water (10 mL) and the mixture partitioned between ethyl acetate (80 mL) and saturated aqueous sodium bicarbonate solution (80 mL). The organic phase was separated, washed with water (80 mL) and saturated brine (80 mL), dried (MgSO$_4$), filtered and concentrated under reduced pressure to give a yellow syrup. The product was purified using flash chromatography on silica eluting with a solvent gradient of 0 to 30% ethyl acetate in hexanes to give the product as a yellow syrup that partially crystallized (0.261 g). The product was dissolved in absolute ethanol (20 mL), 1.25 M hydrochloric acid in ethanol (2.2 mL, 2.74 mmol) added, the mixture stood for 20 minutes then concentrated under reduced pressure to give a white solid. Diethyl ether (20 mL) and absolute ethanol (2 mL) were added and the resulting suspension stirred vigorously overnight then filtered to afford 4-(tert-butyl)-2-((diethylamino)methyl)-6-(6-(trifluoromethyl)pyridin-3-yl)phenol hydrochloride (0.246 g, 28% yield) as a white solid.

HPLC/MS $R_t$=4.13 min, m/z 381.2 (M+H$^+$); analysis calculated for $C_{21}H_{27}F_3N_2O$ HCl: C, 60.50; H, 6.77; N, 6.72; Cl, 8.50. found: C, 60.46; H, 6.68; N, 6.71; Cl, 8.54.

Example 48

4-(tert-Butyl)-2-((isopropylamino)methyl)-6-(6-(trifluoromethyl)pyridin-3-yl)phenol hydrochloride

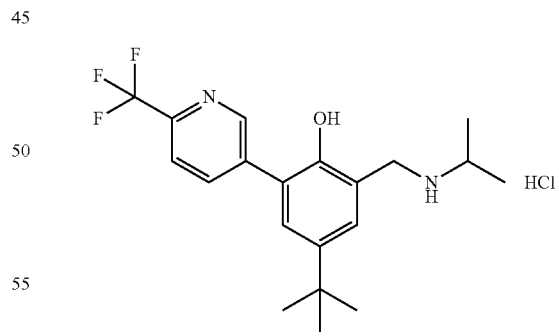

Isopropylamine (0.20 mL, 2.32 mmol) was added to a solution of 5-(tert-butyl)-2-hydroxy-3-(6-(trifluoromethyl)pyridin-3-yl)benzaldehyde (from Example 47 Step 1) (0.30 g, 0.93 mmol) in methanol (7 mL) and the reaction mixture stirred at room temperature under nitrogen for 3.25 hours. Sodium borohydride (52.7 mg, 1.39 mmol) was then added and the reaction mixture stirred at room temperature for 70 minutes. The reaction was quenched by the addition of saturated aqueous ammonium chloride (15 mL) and the mixture partitioned between ethyl acetate (50 mL) and saturated aqueous ammonium chloride (40 mL). The organic phase was separated, washed with water (50 mL) and saturated brine (50 mL), dried (MgSO$_4$), filtered and concentrated under reduced pressure to give a colorless syrup that partially crystallized. The product was purified using flash chromatography on silica eluting with a solvent gradient of 0 to 40% ethyl acetate in hexanes to give the product as a white solid (0.352 g). The product was dissolved in absolute ethanol (30 mL), 1.25 M hydrochloric acid in ethanol (2.97 mL, 3.71 mmol) added, the mixture stood for 20 minutes then concentrated under reduced pressure to give a white solid. Diethyl ether (25 mL) and absolute ethanol (7.5 mL) were added and the resulting suspension stirred vigorously overnight then filtered to afford 4-(tert-butyl)-2-((isopropylamino)methyl)-6-(6-(trifluoromethyl)pyridin-3-yl)phenol hydrochloride (0.267 g, 72% yield) as a white solid.

HPLC/MS $R_t$=3.66 min, m/z 367.3 (M+H$^+$); analysis calculated for C$_{20}$H$_{25}$F$_3$N$_2$O HCl: C, 59.62; H, 6.50; N, 6.95; Cl, 8.80. found: C, 58.71; H, 6.88; N, 6.86; Cl, 8.71.

Example 49

4-(tert-Butyl)-2-(morpholinomethyl)-6-(6-(trifluoromethyl)pyridin-3-yl)phenol hydrochloride

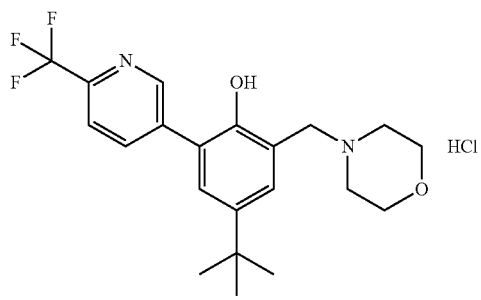 [SMILES: CC(C)(C)c1cc(CN2CCOCC2)c(O)c(-c2ccc(C(F)(F)F)nc2)c1 ; Cl]

Morpholine (0.16 mL, 1.86 mmol) was added to a solution of 5-(tert-butyl)-2-hydroxy-3-(6-(trifluoromethyl)pyridin-3-yl)benzaldehyde (from Example 47 Step 1) (300 g, 0.93 mmol) in dichloroethane (5 mL) at room temperature and the reaction mixture stirred at room temperature under nitrogen for 15 minutes. Sodium triacetoxyborohydride (295 mg, 1.39 mmol) was then added and the reaction mixture stirred at room temperature for 4 days. The reaction was quenched by the addition of water (5 mL) and the mixture partitioned between ethyl acetate (40 mL) and saturated aqueous sodium bicarbonate solution (40 mL). The organic phase was separated, washed with water (40 mL) and saturated brine (40 mL), dried (MgSO$_4$), filtered and concentrated under reduced pressure to give a yellow solid. The product was purified using flash chromatography on silica eluting with a solvent gradient of 0 to 30% ethyl acetate in hexanes to give the product as a white solid (0.323 g). The product was dissolved in absolute ethanol (30 mL), 1.25 M hydrochloric acid in ethanol (2.62 mL, 3.28 mmol) added, the mixture stood for 20 minutes then concentrated under reduced pressure to give a white solid. Diethyl ether (35 mL) and absolute ethanol (5 mL) were added and the resulting suspension stirred vigorously overnight then filtered to afford 4-(tert-butyl)-2-(morpholinomethyl)-6-(6-(trifluoromethyl)pyridin-3-yl)phenol hydrochloride (0.300 g, 75% yield) as a white solid.

HPLC/MS $R_t$=4.57 min, m/z 395.4 (M+H$^+$); analysis calculated for C$_{21}$H$_{25}$F$_3$N$_2$O$_2$HCl: C, 58.54; H, 6.08; N, 6.50; Cl, 8.23. found: C, 58.68; H, 6.14; N, 6.43; Cl, 8.38.

Example 50

4-(tert-Butyl)-2-((4-methylpiperazin-1-yl)methyl)-6-(6-(trifluoromethyl)pyridin-3-yl)phenol dihydrochloride

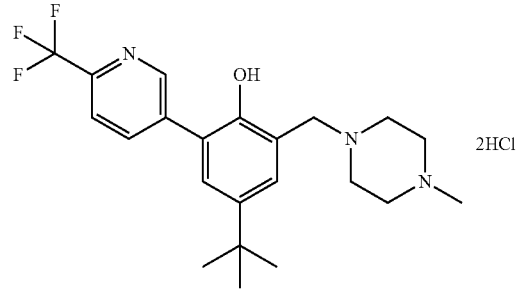 [SMILES: CN1CCN(Cc2cc(C(C)(C)C)cc(-c3ccc(C(F)(F)F)nc3)c2O)CC1]

Sodium triacetoxyborohydride (0.30 g, 1.4 mmol) was added to a solution of 5-(tert-butyl)-2-hydroxy-3-(6-(trifluoromethyl)pyridin-3-yl)benzaldehyde (0.35 g, 1.1 mmol) and 1-methyl piperazine (0.14 mL, 1.3 mmol) in tetrahydrofuran (10 mL). The reaction mixture was stirred at room temperature under nitrogen for 16 hours. The reaction was partitioned between ethyl acetate (25 mL) and saturated aqueous sodium bicarbonate solution (25 mL). The organic phase was dried with sodium sulfate, filtered and concentrated under reduced pressure to give a yellow syrup. The product was purified using flash chromatography on silica eluting with a solvent gradient of 0 to 100% ethyl acetate in hexanes to give a yellow syrup which was dissolved in 1.25 M hydrochloric acid in ethanol (10 mL, 12.5 mmol). The mixture stood for 20 minutes and was then concentrated under reduced pressure to give a white solid which was triturated with diethyl ether (10 mL) and solid was filtered off to afford 4-(tert-butyl)-2-((4-methylpiperazin-1-yl)methyl)-6-(6-(trifluoromethyl)pyridin-3-yl)phenol dihydrochloride (0.26 g, 53% yield) as a white solid.

HPLC/MS $R_t$=5.16 min, m/z 408.3 (M+H$^+$); $^1$H NMR (400 MHz, MeOH-d$_4$) δ 8.87 (d, J=2.1 Hz, 1H), 8.20 (dd, J=8.2, 2.1 Hz, 1H), 7.93 (d, J=8.2 Hz, 1H), 7.70 (d, J=2.6 Hz, 1H), 7.46 (d, J=2.6 Hz, 1H), 4.59 (bs, 2H), 3.95-3.55 (m, 8H), 3.03 (s, 3H), and 1.37 (s, 9H).

Example 51

4-(tert-Butyl)-2-(piperidin-1-ylmethyl)-6-(6-(trifluoromethyl)pyridin-3-yl)phenol hydrochloride

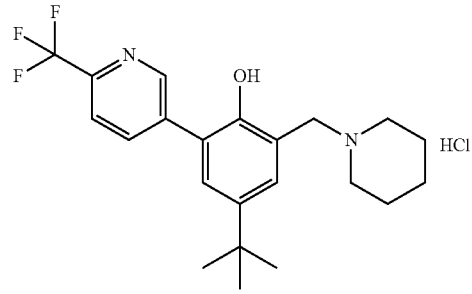 [SMILES: CC(C)(C)c1cc(CN2CCCCC2)c(O)c(-c2ccc(C(F)(F)F)nc2)c1 ; Cl]

Sodium triacetoxyborohydride (0.30 g, 1.4 mmol) was added to a solution of 5-(tert-butyl)-2-hydroxy-3-(6-(trifluoromethyl)pyridin-3-yl)benzaldehyde (0.35 g, 1.1 mmol) and piperidine (0.13 mL, 1.3 mmol) in tetrahydrofuran (10 mL). The reaction mixture was stirred at room temperature under nitrogen for 16 hours. Additional piperidine (013 mL, 1.3 mmol) and sodium triacetoxyborohydride (0.30 g, 1.4 mmol) were added and the reaction was stirred under nitrogen for 4 hours. The reaction was partitioned between ethyl acetate (25 mL) and saturated aqueous sodium bicarbonate solution (25 mL). The organic phase was dried with sodium sulfate, filtered and concentrated under reduced pressure to give a yellow syrup. The product was purified using flash chromatography on silica eluting with a solvent gradient of 0 to 100% ethyl acetate in hexanes to give a yellow syrup which was dissolved in 1.25 M hydrochloric acid in ethanol (10 mL, 12.5 mmol). The mixture stood for 20 minutes and was concentrated under reduced pressure to give a white solid which was triturated with diethyl ether (10 mL) and the solid was filtered off to afford 4-(tert-butyl)-2-(piperidin-1-ylmethyl)-6-(6-(trifluoromethyl)pyridin-3-yl)phenol hydrochloride (0.29 g, 62% yield) as a white solid.

HPLC/MS $R_t$=5.00 min, m/z 393.2 (M+H$^+$); analysis calculated for $C_{22}H_{27}F_3N_2O$ HCl: C, 61.61; H, 6.58; N, 6.53; Cl, 8.27. found: C, 61.66; H, 6.27; N, 6.51; Cl, 8.41.

Example 52

4-(tert-Butyl)-2-(pyrrolidin-1-ylmethyl)-6-(6-(trifluoromethyl)pyridin-3-yl)phenol hydrochloride

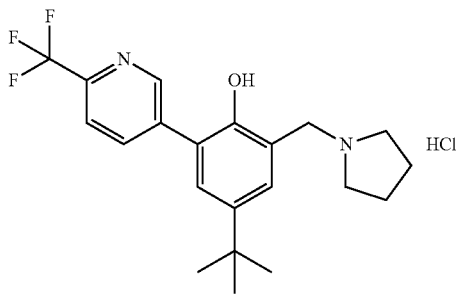 [SMILES: CC(C)(C)c1cc(CN2CCCC2)c(O)c(-c2ccc(C(F)(F)F)nc2)c1 ; Cl]

Sodium triacetoxyborohydride (0.30 g, 1.4 mmol) was added to a solution of 5-(tert-butyl)-2-hydroxy-3-(6-(trifluoromethyl)pyridin-3-yl)benzaldehyde (0.35 g, 1.1 mmol) and pyrrolidine (0.11 mL, 1.3 mmol) in tetrahydrofuran (10 mL). The reaction mixture was stirred at room temperature under nitrogen for 16 hours. Additional pyrrolidine (011 mL, 1.3 mmol) and sodium triacetoxyborohydride (0.30 g, 1.4 mmol) were added and the reaction was stirred under nitrogen for 6 hours. The reaction was partitioned between ethyl acetate (25 mL) and saturated aqueous sodium bicarbonate solution (25 mL). The organic phase was dried with sodium sulfate, filtered and concentrated under reduced pressure to give a yellow syrup. The product was purified using flash chromatography on silica eluting with a solvent gradient of 0 to 100% ethyl acetate in hexanes to give a yellow syrup which was dissolved in 1.25 M hydrochloric acid in ethanol (10 mL, 12.5 mmol). The mixture stood for 20 minutes and was concentrated under reduced pressure to give a white solid which was triturated with diethyl ether (10 mL) and solid was filtered off to afford 4-(tert-butyl)-2-(pyrrolidin-1-ylmethyl)-6-(6-(trifluoromethyl)pyridin-3-yl)phenol hydrochloride (0.18 g, 42% yield) as a white solid.

HPLC/MS $R_t$=4.67 min, m/z 379.1 (M+H$^+$); analysis calculated for $C_{21}H_{25}F_3N_2O$ HCl: C, 60.79; H, 6.32; N, 6.75; Cl, 8.55. found: C, 60.77; H, 5.94; N, 6.61; Cl, 8.71.

Example 53

1-(4-(5-(tert-Butyl)-2-hydroxy-3-(6-(trifluoromethyl)pyridin-3-yl)benzyl)piperazin-1-yl)ethanone hydrochloride

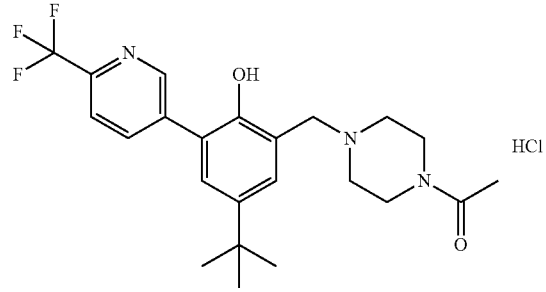 [SMILES: CC(=O)N1CCN(Cc2cc(C(C)(C)C)cc(-c3ccc(C(F)(F)F)nc3)c2O)CC1 ; Cl]

Sodium triacetoxyborohydride (0.41 g, 2.0 mmol) was added to a solution of 5-(tert-butyl)-2-hydroxy-3-(6-(trifluoromethyl)pyridin-3-yl)benzaldehyde (0.35 g, 1.1 mmol) and 1-acetylpiperazine (0.24 mL, 1.8 mmol) in tetrahydrofuran (10 mL). The reaction mixture was stirred at room temperature under nitrogen for 16 hours. The reaction mixture was partitioned between ethyl acetate (25 mL) and saturated aqueous sodium bicarbonate solution (25 mL). The organic phase was dried with sodium sulfate, filtered and concentrated under reduced pressure to give a yellow syrup. The product was purified using flash chromatography on silica eluting with a solvent gradient of 0 to 100% ethyl acetate in hexanes to give a colorless oil which was dissolved in 1.25 M hydrochloric acid in ethanol (10 mL, 12.5 mmol). The mixture stood for 20 minutes and was then concentrated under reduced pressure to give a white solid which was triturated with diethyl ether (10 mL) and solid was filtered off to afford 1-(4-(5-(tert-butyl)-2-hydroxy-3-(6-(trifluoromethyl)pyridin-3-yl)benzyl)piperazin-1-yl)ethanone hydrochloride (0.32 g, 61% yield) as a white solid.

HPLC/MS $R_t$=4.51 min, m/z 436.2 (M+H$^+$); $^1$H NMR (300 MHz, DMSO-$d_6$) δ 9.29 (bs, 1H), 8.92 (d, J=3.0 Hz, 1H), 8.24-8.20 (m, 2H), 7.98 (dd, J=7.5, 3.0, 1H), 7.67 (d, J=3.0 Hz, 1H), 7.45 (d, J=3.0 Hz, 1H), 4.43 (bs, 2H), 4.11-2.80 (m, 8H), 2.05 (s, 3H), 1.32 (s, 9H).

Example 54

4-(tert-Butyl)-2-((tert-butylamino)methyl)-6-(5-(trifluoromethyl)pyrimidin-2-yl)phenol hydrochloride

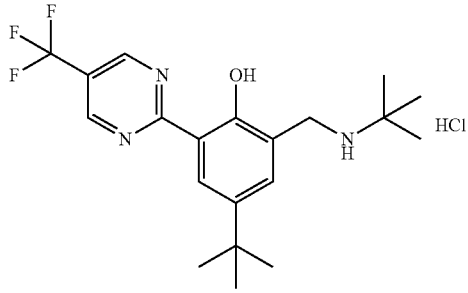 [SMILES: CC(C)(C)NCc1cc(C(C)(C)C)cc(-c2ncc(C(F)(F)F)cn2)c1O ; Cl]

Step 1: 2-(5-(tert-butyl)-2-(methoxymethoxy)phenyl)-5-(trifluoromethyl)pyrimidine Following a procedure by Ronald, R. C. et al (*J. Org. Chem.*, 1980, 40, 2224-2229) a 1.7 molar solution of tert-butyl lithium in pentane (6.70 mL, 11.3 mmol) was added to a solution of 1-(tert-butyl)-4-(methoxymethoxy)benzene (2.00 g, 10.3 mmol, Kovacs, M. S. et al *J. Chem. Soc. Dalton*, 2001, 3015-3024) in pentane (40 mL) under a nitrogen atmosphere at 0° C. A solid precipitated and the pentane was evaporated under a steady stream of nitrogen gas. To this remaining solid was added tetrahydrofuran (50 mL) and the solution was cooled to −78° C. Trimethyl borate (1.70 mL, 15.5 mmol) was added slowly and the solution was stirred at −78° C. under nitrogen gas for 30 minutes. Thin layer chromatography showed consumption of the starting material and water (10 mL) was added and the solution was partitioned between ethyl acetate and 1 N aqueous sodium hydroxide solution. The organic phase was separated and dried with sodium sulfate, filtered and concentrated under reduced pressure to give 2.70 g of crude (5-(tert-butyl)-2-(methoxymethoxy)phenyl)boronic acid which was used without further purification.

To a solution of 2-chloro-5-(trifluoromethyl)pyrimidine (0.300 g, 1.64 mmol) in dimethoxyethane (9 mL) was added a 2 M aqueous solution of sodium carbonate (3.7 mL, 7.4 mmol) and (5-(tert-butyl)-2-(methoxymethoxy)phenyl)boronic acid (0.500 g, 2.14 mmol). The solution was degassed with nitrogen for five minutes and tetrakis(triphenylphosphine)palladium(0) (95 mg, 0.082 mmol) was added and the reaction mixture heated to 80° C. in a sealed vial for 16 hours. The cooled reaction mixture was partitioned between ethyl acetate (25 mL) and 1 M aqueous sodium hydroxide solution (25 mL), the organic phase separated, dried (Na$_2$SO$_4$), filtered and concentrated under reduced pressure to give a yellow syrup. The crude product was purified by chromatography on silica eluting with a solvent gradient of 0 to 100% ethyl acetate in hexanes to give 2-(5-(tert-butyl)-2-(methoxymethoxy)phenyl)-5-(trifluoromethyl)pyrimidine (0.25 g, 44% yield) as a colorless oil.

HPLC/MS $R_f$=7.12 min, m/z 341.1 (M+H$^+$).

Step 2: 4-(tert-butyl)-2-(5-(trifluoromethyl)pyrimidin-2-yl)phenol

To a solution of 2-(5-(tert-butyl)-2-(methoxymethoxy)phenyl)-5-(trifluoromethyl)pyrimidine (0.23 g, 0.68 mmol) in methanol (10 mL) was added a catalytic amount of para-toluenesulfonic acid (10 mg) and the reaction mixture stirred at 40° C. open to air for 30 minutes. The reaction mixture was concentrated under reduced pressure to give 4-(tert-butyl)-2-(5-methylpyridin-2-yl)phenol (0.20 g, 100% yield) as a colorless oil.

HPLC/MS $R_f$=7.95 min, m/z 297.1 (M+H$^+$).

Step 3: 4-(tert-butyl)-2-((tert-butylamino)methyl)-6-(5-(trifluoromethyl)pyrimidin-2-yl)phenol hydrochloride A mixture of paraformaldehyde (102 mg, 3.4 mmol) and tert-butylamine (0.36 mL, 3.4 mmol) in isopropanol (2 mL) was gently refluxed under nitrogen for 1 hour. A solution of 4-(tert-butyl)-2-(5-methylpyridin-2-yl)phenol (0.20 g, 0.68 mmol) in isopropanol (5 mL) was added and the reaction mixture refluxed for 16 hours. An additional portion of paraformaldehyde (102 mg, 3.4 mmol) and tert-butylamine (0.36 mL, 3.4 mmol) was added and the reaction mixture was refluxed for an additional 16 hours. The cooled reaction mixture was then concentrated under reduced pressure. The residue was purified by chromatography on silica eluting with a solvent gradient of 0 to 100% ethyl acetate in hexanes to give 3,6-di-tert-butyl-8-(5-(trifluoromethyl)pyrimidin-2-yl)-3,4-dihydro-2H-benzo[e][1,3]oxazine which was dissolved in absolute ethanol (3 mL), 1.0 M aqueous hydrochloric acid solution (1 mL) added and the reaction mixture was stirred at room temperature for 3 days. The reaction mixture was concentrated under reduced pressure and the residue was purified by chromatography on silica eluting with a solvent gradient of 0 to 100% solution of (1% ammonia, 10% methanol and 89% dichloromethane) in dichloromethane to give a colorless oil. The product was dissolved in a hydrogen chloride-ethanol solution (1.25 M, 4.0 mL, 5.0 mmol), the mixture stood for 20 minutes then concentrated under reduced pressure to give a cream solid. The solid was triturated with diethyl ether (3×10 mL) and the solid filtered to give 4-(tert-butyl)-2-((tert-butylamino)methyl)-6-(5-(trifluoromethyl)pyrimidin-2-yl)phenol hydrochloride (157 mg, 55% yield) as a white solid.

HPLC/MS $R_f$=4.81 min, m/z 382.3 (M+H$^+$); analysis calculated for C$_{20}$H$_{26}$F$_3$N$_3$O HCl: C, 57.48; H, 6.51; N, 10.06; Cl, 8.48. found: C, 57.62; H, 6.29; N, 10.08; Cl, 8.50.

Example 55

3-((tert-Butylamino)methyl)-4'-(methylsulfonyl)-5-(6-(trifluoromethyl)pyridin-3-yl)-[1,1'-biphenyl]-4-ol hydrochloride

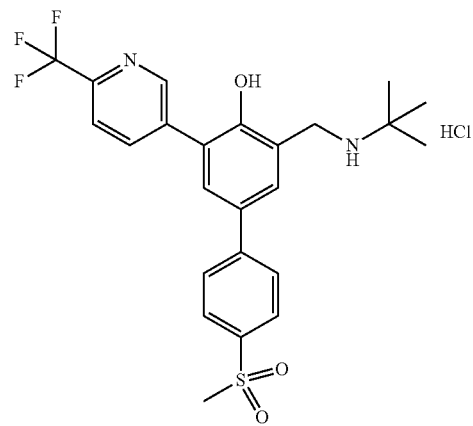 [SMILES: CC(C)(C)NCc1cc(-c2ccc(S(C)(=O)=O)cc2)cc(-c2ccc(C(F)(F)F)nc2)c1O ; Cl]

Step 1: 4-Hydroxy-4'-(methylsulfonyl)-[1,1'-biphenyl]-3-carbaldehyde

A mixture of 5-bromosalicylaldehyde (1.005 g, 5.0 mmol), 4-(methylsulfonyl)phenylboronic acid [purchased from Frontier Scientific] (1.00 g, 5.00 mmol) and potassium carbonate (1.727 g, 12.5 mmol) in dimethoxyethane (15 mL) and water (5 mL) was purged with nitrogen for 20 minutes. Tetrakis(triphenylphosphine)palladium(0) (288.9 mg, 0.25 mmol) was then added and the mixture heated at 80° C. in a sealed vial for 21 hours. The cooled reaction mixture was then partitioned between ethyl acetate (80 mL) and 1M aqueous hydrochloric acid (80 mL). The organic phase was separated, washed with water (80 mL) and saturated brine (80 mL), dried (MgSO$_4$), filtered and concentrated under reduced pressure to give a brown syrup. The product was purified using flash chromatography on silica eluting with a solvent gradient of 10 to 100% ethyl acetate in hexanes to give the product as a yellow solid (0.9 g). The product was then triturated with diethyl ether (50 mL) to give 4-hydroxy-4'-(methylsulfonyl)-[1,1'-biphenyl]-3-carbaldehyde (0.707 g, 51% yield) as a cream solid.

HPLC/MS $R_f$=4.05 min, m/z 277.1 (M+H$^+$).

Step 2: 5-Bromo-4-hydroxy-4'-(methylsulfonyl)-[1,1'-biphenyl]-3-carbaldehyde

To a mixture of 4-hydroxy-4'-(methylsulfonyl)-[1',1'-biphenyl]-3-carbaldehyde (0.6544 g, 2.37 mmol) and sodium acetate (291.4 mg, 3.55 mmol) in acetic acid (4 mL) and dichloromethane (8 mL) at room temperature under nitrogen was added bromine (0.12 mL, 2.37 mmol) dropwise. The reaction mixture was then stirred at room temperature for 2 hours. The mixture was concentrated under reduced pressure and azeotroped with toluene (25 mL) to remove residual acetic acid. The reside was partitioned between dichloromethane (100 mL) and saturated aqueous sodium thiosulfate solution (80 mL). The organic phase was separated, washed with saturated brine (80 mL), dried (MgSO$_4$), filtered and concentrated under reduced pressure to give a yellow solid. The product was then triturated with ethyl acetate (15 mL) and then with 10:1 v/v ethyl acetate:methanol (11 mL) to give 5-bromo-4-hydroxy-4'-(methylsulfonyl)-[1,1'-biphenyl]-3-carbaldehyde (0.567 g, 67% yield) as a yellow solid.

HPLC/MS R$_t$=5.11 min, m/z 355.0 and 357.0 (M+H$^+$).

Step 3: 4-Hydroxy-4'-(methylsulfonyl)-5-(6-(trifluoromethyl)pyridin-3-yl)-[1,1'-biphenyl]-3-carbaldehyde A mixture of 5-bromo-4-hydroxy-4'-(methylsulfonyl)-[1', 1'-biphenyl]-3-carbaldehyde (0.56 g, 1.58 mmol), 2-(trifluoromethyl)pyridine-5-boronic acid (331 mg, 1.73 mmol) and potassium carbonate (545 mg, 3.94 mmol) in dimethoxyethane (15 mL) and water (5 mL) was purged with nitrogen for 20 minutes. Tetrakis(triphenylphosphine)palladium(0) (91 mg, 0.079 mmol) was then added and the mixture heated at 80° C. in a sealed vial for 16 hours. The cooled reaction mixture was then partitioned between ethyl acetate (80 mL) and saturated aqueous ammonium chloride (80 mL). The organic phase was separated, washed with water (50 mL) and saturated brine (50 mL), dried (MgSO$_4$), filtered and concentrated under reduced pressure to give a yellow syrup. The product was purified using flash chromatography on silica eluting with a solvent gradient of 0 to 50% ethyl acetate in hexanes to give 4-hydroxy-4'-(methylsulfonyl)-5-(6-(trifluoromethyl)pyridin-3-yl)-[1,1'-biphenyl]-3-carbaldehyde (149.9 mg, 23% yield) as a white solid.

HPLC/MS R$_t$=6.01 min, m/z 422.0 (M+H$^+$).

Step 4: 3-((tert-Butylamino)methyl)-4'-(methylsulfonyl)-5-(6-(trifluoromethyl)pyridin-3-yl)-[1,1'-biphenyl]-4-ol hydrochloride tert-Butylamine (0.072 mL, 0.69 mmol) was added to a suspension of 4-hydroxy-4'-(methylsulfonyl)-5-(6-(trifluoromethyl)pyridin-3-yl)-[1,1'-biphenyl]-3-carbaldehyde (144.5 mg, 0.34 mmol) in methanol (8 mL) and the resulting solution stirred at room temperature for 2.25 hours. Sodium borohydride (19.5 mg, 0.51 mmol) was then added and the reaction mixture stirred for a further 2.5 hours. The reaction was then quenched by the addition of saturated aqueous ammonium chloride solution (10 mL) and the mixture partitioned between ethyl acetate (60 mL) and of saturated aqueous ammonium chloride solution (60 mL). The organic phase was separated, washed with water (60 mL) and saturated brine (60 mL), dried (MgSO$_4$), filtered and concentrated under reduced pressure to give a yellow syrup. The product was purified using flash chromatography on silica eluting with a solvent gradient of 0 to 80% ethyl acetate in hexanes to give the product as a colorless syrup (0.146 g). The product was dissolved in absolute ethanol (20 mL), 1.25 M hydrochloric acid in ethanol (0.98 mL, 1.22 mmol) added, the mixture stood for 20 minutes then concentrated under reduced pressure to give a yellow syrup. Diethyl ether (20 mL) and absolute ethanol (4 mL) were added and the resulting suspension stirred vigorously overnight then filtered to afford 3-((tert-butylamino)methyl)-4'-(methylsulfonyl)-5-(6-(trifluoromethyl)pyridin-3-yl)-[1,1'-biphenyl]-4-ol hydrochloride (85.5 mg, 48% yield) as a white solid.

HPLC/MS R$_t$=3.00 min, m/z 479.4 (M+H$^+$).

Example 56

4-(tert-Butyl)-2-((tert-butylamino)methyl)-6-(6-(trifluoromethyl)pyridazin-3-yl)phenol hydrochloride

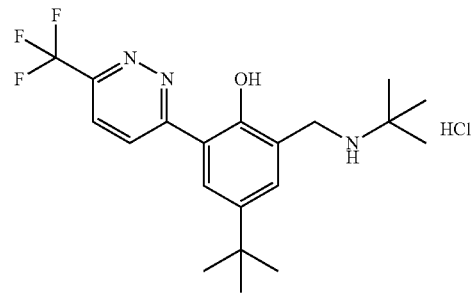 [SMILES: CC(C)(C)NCc1cc(C(C)(C)C)cc(-c2ccc(C(F)(F)F)nn2)c1O ; Cl]

Step 1: 3-(5-(tert-Butyl)-2-((2-methoxyethoxy)methoxy)phenyl)-6-(trifluoromethyl)pyridazine A mixture of 3-chloro-6-trifluoromethylpyridazine [purchased from Combi-Blocks] (250 mg, 1.37 mmol), (5-(tert-butyl)-2-((2-methoxyethoxy)methoxy)phenyl)boronic acid [Intermediate 7] (463.8 mg, 1.64 mmol) and potassium carbonate (284.5 mg, 2.06 mmol) in dimethoxyethane (7.5 mL) and water (2.5 mL) was purged with nitrogen for 20 minutes. Tetrakis(triphenylphosphine)palladium(0) (79.1 mg, 0.068 mmol) was added and the reaction mixture heated to 80° C. in a sealed vial for 22 hours. The cooled reaction mixture was partitioned between ethyl acetate (50 mL) and 10% aqueous sodium carbonate solution (50 mL), the organic phase separated, washed with water (50 mL) and saturated brine (50 mL), dried (MgSO$_4$), filtered and concentrated under reduced pressure to give a brown syrup. The crude product was purified by chromatography on silica eluting with a solvent gradient of 0 to 30% ethyl acetate in hexanes to give 3-(5-(tert-butyl)-2-((2-methoxyethoxy)methoxy)phenyl)-6-(trifluoromethyl)pyridazine (0.462 g, 88% yield) as a colorless syrup.

HPLC/MS R$_t$=6.90 min, m/z 385.4 (M+H$^+$).

Step 2: 4-(tert-Butyl)-2-(6-(trifluoromethyl)pyridazin-3-yl)phenol

A solution of 3-(5-(tert-butyl)-2-((2-methoxyethoxy)methoxy)phenyl)-6-(trifluoromethyl)pyridazine (0.452 g, 1.18 mmol) in methanol (50 mL) and 1.0M aqueous hydrochloric acid (25 mL) was stirred at 60° C. for 5 hours. The cooled reaction mixture was then concentrated under reduced pressure to remove methanol. The resulting aqueous suspension was partitioned between ethyl acetate (80 mL) and saturated aqueous sodium hydrogen carbonate solution (80 mL), the organic phase separated, washed with water (80 mL) and saturated brine (80 mL), dried (MgSO$_4$), filtered and concentrated under reduced pressure to give a cream solid. The crude product was purified by chromatography on silica eluting with a solvent gradient of 0 to 20% ethyl acetate in hexanes to give 4-(tert-butyl)-2-(6-(trifluoromethyl)pyridazin-3-yl)phenol (0.282 g, 81% yield) as a cream solid.

HPLC/MS R$_t$=7.18 min, m/z 297.2 (M+H$^+$).

Step 3: 4-(tert-Butyl)-2-((tert-butylamino)methyl)-6-(6-(trifluoromethyl)pyridazin-3-yl)phenol hydrochloride A mixture of paraformaldehyde (137.8 mg, 4.59 mmol) and tert-butylamine (0.48 mL, 4.59 mmol) in isopropanol (5 mL) was gently refluxed under nitrogen for 1 hour. A solution of 4-(tert-butyl)-2-(6-(trifluoromethyl)pyridazin-3-yl)phenol (272 mg, 0.918 mmol) in isopropanol (10 mL) was added and the reaction mixture refluxed for 5 days. The reaction mixture was cooled to 4° C. for 1 hour and the resulting suspension filtered, washing the solid product with ice cold isopropanol to give a white solid (239.8 mg). The crude 3,4-dihydro-2H-benzo[e][1,3]oxazine (239.8 mg) was dissolved in methanol (90 mL), 1.0 M aqueous hydrochloric acid solution (60 mL) was added and the reaction mixture stirred at room temperature for 7 days. The reaction mixture was concentrated under reduced pressure to remove methanol, the resulting aqueous suspension partitioned between ethyl acetate (80 mL) and saturated aqueous sodium hydrogen carbonate solution (80 mL). The organic phase was separated, washed with half saturated brine (80 mL) and saturated brine (80 mL), dried (MgSO$_4$), filtered and concentrated under reduced pressure to give a cream solid. The crude product was purified by chromatography on silica eluting with a solvent gradient of 0 to 6% methanol (containing 1% aqueous ammonium hydroxide) in dichloromethane to give the product as a cream solid (244.9 mg). The product was dissolved in absolute ethanol (40 mL), 1.25 M hydrochloric acid in ethanol (2.05 mL, 2.57 mmol) added, the mixture stood for 20 minutes then concentrated under reduced pressure to give a yellow syrup. Diethyl ether (15 mL) and absolute ethanol (1 mL) were added and the resulting suspension stirred vigorously overnight then filtered to give 4-(tert-butyl)-2-((tert-butylamino)methyl)-6-(6-(trifluoromethyl)pyridazin-3-yl)phenol hydrochloride (216.8 mg, 57% yield) as a cream solid.

HPLC/MS R$_t$=4.57 min, m/z 382.4 (M+H$^+$); analysis calculated for C$_{20}$H$_{26}$F$_3$N$_3$O HCl: C, 57.48; H, 6.51; N, 10.06; Cl, 8.48. found: C, 57.54; H, 6.59; N, 10.05; Cl, 8.57.

Example 57

4-(tert-Butyl)-2-(6-(trifluoromethyl)pyridin-3-yl)-6-(((3,3,3-trifluoropropyl)amino)methyl)phenol hydrochloride

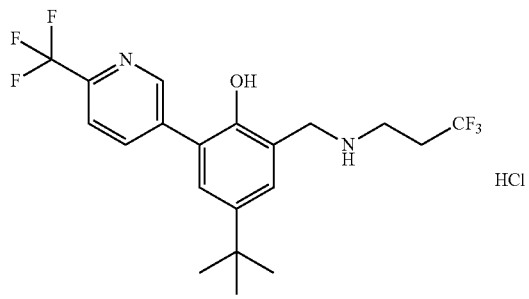 [SMILES: CC(C)(C)c1cc(CNCCC(F)(F)F)c(O)c(-c2ccc(C(F)(F)F)nc2)c1 ; Cl]

N,N-Diisopropylethylamine (0.364 mL, 2.09 mmol) was added to a mixture of 3,3,3-trifluoro-n-propylamine hydrochloride (312.2 mg, 2.09 mmol) and 5-(tert-butyl)-2-hydroxy-3-(6-(trifluoromethyl)pyridin-3-yl)benzaldehyde (from Example 47 Step 1) (270 mg, 0.835 mmol) in methanol (5 mL) and the reaction mixture stirred at room temperature under nitrogen for 4.5 hours. Sodium borohydride (63.2 mg, 1.67 mmol) was then added and the reaction mixture stirred at room temperature for 1.75 hours. The reaction was quenched by the addition of saturated aqueous ammonium chloride solution (4 mL) and the mixture partitioned between ethyl acetate (40 mL) and saturated aqueous ammonium chloride solution (40 mL). The organic phase was separated, washed with water (40 mL) and saturated brine (40 mL), dried (MgSO$_4$), filtered and concentrated under reduced pressure to give a yellow syrup. The product was purified using flash chromatography on silica eluting with a solvent gradient of 0 to 25% ethyl acetate in hexanes to give the product as a white solid (287.8 mg, 82% yield). The product was dissolved in absolute ethanol (30 mL), 1.25 M hydrochloric acid in ethanol (2.2 mL, 2.74 mmol) added, the mixture stood for 20 minutes then concentrated under reduced pressure to give a yellow syrup. Diethyl ether (10 mL) and hexanes (10 mL) were added and the resulting suspension stirred vigorously overnight then filtered to afford 4-(tert-butyl)-2-(6-(trifluoromethyl)pyridin-3-yl)-6-(((3,3,3-trifluoropropyl)amino)methyl)phenol hydrochloride (275.8 mg, 72% yield) as a white solid.

HPLC/MS R$_t$=5.09 min, m/z 421.3 (M+H$^+$); analysis calculated for C$_{20}$H$_{22}$F$_6$N$_2$O HCl: C, 52.58; H, 5.07; N, 6.13; Cl, 7.76. found: C, 52.55; H, 4.84; N, 6.08; Cl, 7.89.

Example 58

4-(tert-Butyl)-2-((tert-butyl(cyclohexylmethyl)amino)methyl)-6-(6-(trifluoromethyl)pyridin-3-yl)phenol hydrochloride

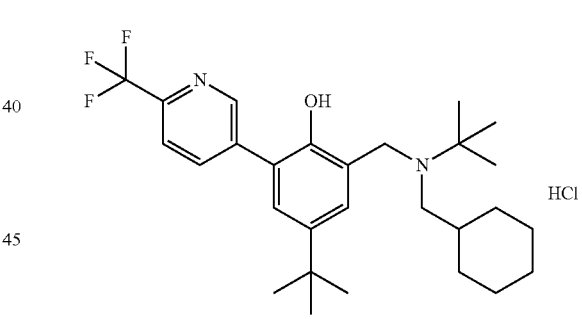

To a solution of 3,6-di-tert-butyl-8-(6-(trifluoromethyl)pyridin-3-yl)-3,4-dihydro-2H-benzo[e][1,3]oxazine (Example 75) (250 mg, 0.63 mmol) in THF (10 mL) under argon was added dropwise a 2.0 M solution of cyclohexylmagnesium chloride in diethyl ether (0.41 mL, 0.82 mmol). The reaction mixture was stirred at room temperature for 16 hours, and then partitioned between ethyl acetate and a saturated aqueous sodium bicarbonate solution. The organic phase was separated, dried (Na$_2$SO$_4$), filtered, and the crude product purified using flash chromatography on silica eluting with a solvent gradient of 0 to 100% ethyl acetate in hexanes. The product was dissolved in a 1.25 M solution of hydrochloric acid in ethanol (5 mL, 6.3 mmol), the mixture stirred for 30 minutes then concentrated under reduced pressure and the product triturated with hexane to give 4-(tert-butyl)-2-((tert-butyl(cyclohexylmethyl)amino)methyl)-6-(6-(trifluoromethyl)pyridin-3-yl)phenol hydrochloride (162 mg, 50% yield) as a white powder.

HPLC/MS $R_t$=7.2 min, m/z 477.5 (M+H$^+$). $^1$H NMR (400 MHz, DMSO-d$_6$) δ 9.56 (bs, 1H), 8.97 (bs, 1H), 8.84 (s, 1H), 8.15 (d, J=8.2 Hz, 1H), 8.00 (d, J=8.2 Hz, 1H), 7.94 (bs, 1H), 7.44 (bs, 1H), 4.51-4.36 (m, 2H), 3.18-3.08 (m, 1H), 2.83-2.72 (m, 1H), 2.11 (d, J=9.2 Hz, 1H), 1.58-1.22 (m, 4H), 1.52 (s, 9H), 1.33 (s, 9H), and 0.94-0.46 (m, 6H).

Example 59

4-(tert-Butyl)-2-(((5-(diethylamino)pentan-2-yl) amino)methyl)-6-(6-(trifluoromethyl)pyridin-3-yl) phenol dihydrochloride

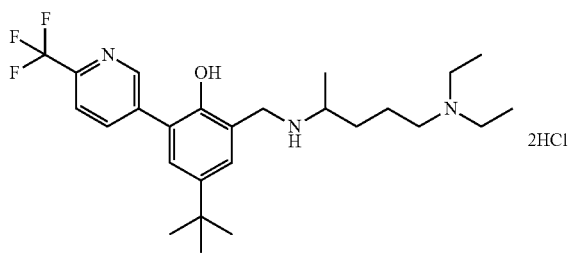 [SMILES: CCN(CC)CCCC(C)NCc1cc(C(C)(C)C)cc(-c2ccc(C(F)(F)F)nc2)c1O ; "2HCl"]

4-Amino-1-diethylaminopentane (0.45 mL, 2.32 mmol) was added to a solution of 5-(tert-butyl)-2-hydroxy-3-(6-(trifluoromethyl)pyridin-3-yl)benzaldehyde (from Example 47 Step 1) (0.5 g, 1.55 mmol) in methanol (5 mL) and the reaction mixture stirred at room temperature under nitrogen for 7.75 hours. Sodium borohydride (234 mg, 6.19 mmol) was then added and the reaction mixture stirred at room temperature for 1.5 hours. The reaction was quenched by the addition of saturated aqueous ammonium chloride solution (5 mL), the mixture stirred vigorously for 10 minutes then partitioned between ethyl acetate (60 mL) and saturated aqueous ammonium chloride solution (60 mL). The organic phase was separated, washed with water (60 mL) and saturated brine (60 mL), dried (MgSO$_4$), filtered and concentrated under reduced pressure to give a yellow syrup. The product was purified using flash chromatography on silica eluting with a solvent gradient of 0 to 10% methanol (containing 1% aqueous ammonium hydroxide) in dichloromethane to give the product as a yellow syrup (0.662 g, 92% yield). The product was dissolved in absolute ethanol (30 mL), 1.25 M hydrochloric acid in ethanol (6.82 mL, 8.53 mmol) added, the mixture stood for 20 minutes then concentrated under reduced pressure to give a yellow syrup that partially crystallized. The product was dissolved in ethanol (8 mL), diethyl ether (40 mL) added slowly and the resulting suspension stirred vigorously overnight then filtered to afford 4-(tert-butyl)-2-(((5-(diethylamino)pentan-2-yl)amino)methyl)-6-(6-(trifluoromethyl)pyridin-3-yl)phenol dihydrochloride (0.722 g, 87% yield) as a white solid.

HPLC/MS $R_t$=1.81 min, m/z 466.5 (M+H$^+$); analysis calculated for C$_{26}$H$_{38}$F$_3$N$_3$O 2HCl: C, 57.99; H, 7.49; N, 7.80; Cl, 13.17. found: C, 58.02; H, 7.64; N, 7.68; Cl, 13.13.

Example 60

4-(tert-Butyl)-2-(((3-(tert-butylamino)propyl)amino) methyl)-6-(6-(trifluoromethyl)pyridin-3-yl)phenol dihydrochloride

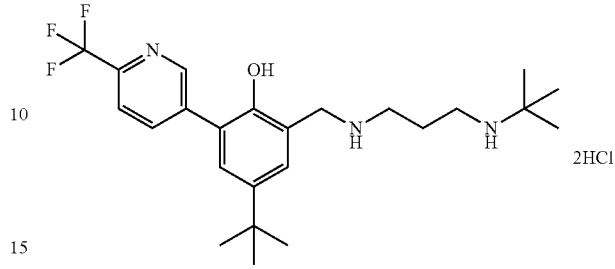

4-(tert-Butyl)-2-(((3-(tert-butylamino)propyl)amino)methyl)-6-(6-(trifluoromethyl)pyridin-3-yl)phenol dihydrochloride was prepared as a white solid using the same procedure as described in Example 59, replacing 4-amino-1-diethylaminopentane with 3-tert-butylaminopropylamine HPLC/MS $R_t$=1.53 min, m/z 438.5 (M+H$^+$); analysis calculated for C$_{24}$H$_{34}$F$_3$N$_3$O 2HCl: C, 56.47; H, 7.11; N, 8.23; Cl, 13.89. found: C, 56.08; H, 7.14; N, 8.05; Cl, 14.03.

Example 61

4-(tert-Butyl)-2-(((3-(diethylamino)propyl)amino) methyl)-6-(6-(trifluoromethyl)pyridin-3-yl)phenol dihydrochloride

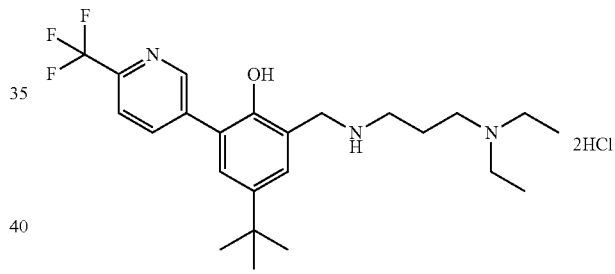

4-(tert-Butyl)-2-(((3-(diethylamino)propyl)amino)methyl)-6-(6-(trifluoromethyl)pyridin-3-yl)phenol dihydrochloride was prepared as a white solid using the same procedure as described in Example 59, replacing 4-amino-1-diethylaminopentane with N,N-diethyl-1,3-diaminopropane.

Example 62

2-(((3-Aminopropyl)amino)methyl)-4-(tert-butyl)-6-(6-(trifluoromethyl)pyridin-3-yl)phenol dihydrochloride

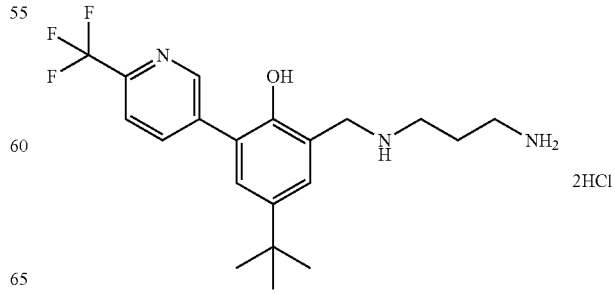

Step 1: tert-Butyl (3-((5-(tert-butyl)-2-hydroxy-3-(6-(trifluoromethyl)pyridin-3-yl)benzyl)amino)propyl)carbamate tert-Butyl N-(3-aminopropyl)carbamate (0.404 g, 2.32 mmol) was added to a solution of 5-(tert-butyl)-2-hydroxy-3-(6-(trifluoromethyl)pyridin-3-yl)benzaldehyde (from Example 47 Step 1) (0.5 g, 1.55 mmol) in methanol (5 mL) and the reaction mixture stirred at room temperature under nitrogen for 4 hours. Sodium borohydride (234 mg, 6.19 mmol) was then added and the reaction mixture stirred at room temperature for 2.5 hours. The reaction was quenched by the addition of saturated aqueous ammonium chloride solution (5 mL), the mixture stirred vigorously for 10 minutes then partitioned between ethyl acetate (80 mL) and saturated aqueous ammonium chloride solution (80 mL). The organic phase was separated, washed with water (80 mL) and saturated brine (80 mL), dried (MgSO$_4$), filtered and concentrated under reduced pressure to give a yellow syrup. The product was purified using flash chromatography on silica eluting with a solvent gradient of 0 to 6% methanol (containing 1% aqueous ammonium hydroxide) in dichloromethane to give tert-butyl (3-((5-(tert-butyl)-2-hydroxy-3-(6-(trifluoromethyl)pyridin-3-yl)benzyl)amino)propyl)carbamate (0.755 g, 100% yield) as a yellow syrup.

HPLC/MS R$_t$=5.08 min, m/z 482.5 (M+H$^+$).

Step 2: 2-(((3-Aminopropyl)amino)methyl)-4-(tert-butyl)-6-(6-(trifluoromethyl)pyridin-3-yl)phenol dihydrochloride 4.0 M Hydrochloric acid in dioxane (1.96 mL, 7.84 mmol) was added to a solution of tert-butyl (3-((5-(tert-butyl)-2-hydroxy-3-(6-(trifluoromethyl)pyridin-3-yl)benzyl)amino)propyl)carbamate (0.755 g, 1.57 mmol) in dioxane (30 mL) and the reaction mixture stirred at room temperature under nitrogen for 2 hours and then for 1 hour at 60° C. The cooled reaction mixture was concentrated under reduced pressure to give a yellow syrup. The crude product was dissolved in ethyl acetate (80 mL), washed with saturated aqueous sodium hydrogen carbonate solution (80 mL), water (80 mL) and saturated brine (80 mL), dried (MgSO$_4$), filtered and concentrated under reduced pressure to give a brown syrup. The product was purified using flash chromatography on silica eluting with a solvent gradient of 0 to 10% methanol (containing 1% aqueous ammonium hydroxide) in dichloromethane to give the product as a yellow syrup (0.46 g, 77% yield). The product was dissolved in absolute ethanol (25 mL), 1.25 M hydrochloric acid in ethanol (5.8 mL, 7.24 mmol) added, the mixture stood for 20 minutes then concentrated under reduced pressure to give a yellow syrup. The product was dissolved in ethanol (2 mL), diethyl ether (40 mL) added slowly and the resulting suspension stirred vigorously overnight then filtered to afford 2-(((3-aminopropyl)amino)methyl)-4-(tert-butyl)-6-(6-(trifluoromethyl)pyridin-3-yl)phenol dihydrochloride (0.436 g, 62% yield) as a white solid.

HPLC/MS R$_t$=0.98 min, m/z 382.4 (M+H$^+$); analysis calculated for C$_{20}$H$_{26}$F$_3$N$_3$O 2HCl: C, 52.87; H, 6.21; N, 9.25; Cl, 15.61. found: C, 52.88; H, 6.17; N, 9.01; Cl, 15.87.

Example 63

4-(tert-Butyl)-2-(((2-(diethylamino)ethyl)amino)methyl)-6-(6-(trifluoromethyl)pyridin-3-yl)phenol dihydrochloride

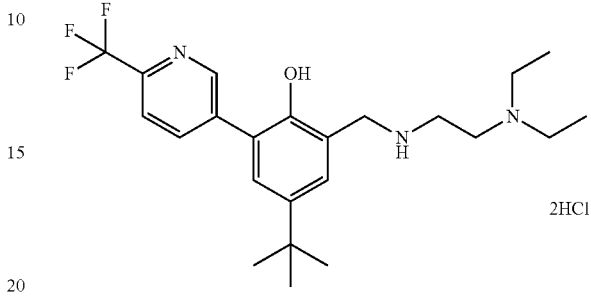

Sodium triacetoxy borohydride (590 mg, 2.79 mmol) was added to a solution of N,N-diethylethylenediamine (0.37 mL, 2.63 mmol) and 5-(tert-butyl)-2-hydroxy-3-(6-(trifluoromethyl)pyridin-3-yl)benzaldehyde (Example 47, Step 1) (0.50 g, 1.55 mmol) in tetrahydrofuran (15 mL) and the reaction mixture stirred at room temperature under nitrogen for 16 hours. Progress of the reaction was monitored by LC/MS and showed both product and starting material. A reaction aliquot was treated with sodium borohydride and the LC/MS showed only product. Therefore, the reaction solvent was removed under reduced pressure and the residue re-dissolved in methanol (15 mL) and sodium borohydride (286 mg, 7.74 mmol) added. The reaction mixture was stirred at room temperature for 10 minutes and then saturated aqueous ammonium chloride solution (1.0 mL) added. The reaction mixture was partitioned between saturated aqueous ammonium chloride solution and ethyl acetate. The organic phase was separated, dried (Na$_2$SO$_4$), filtered and the solvent was removed under reduced pressure. The residue was purified using flash chromatography on silica eluting with a solvent gradient of 0 to 100% (1% ammonium hydroxide, 10% methanol, 89% methylene chloride) in methylene chloride. The product was dissolved in a 1.25 M solution of hydrochloric acid in ethanol (5 mL, 6.3 mmol), the mixture stirred for 30 minutes then concentrated under reduced pressure. The product was triturated with diethyl ether to give 4-(tert-butyl)-2-(((2-(diethylamino)ethyl)amino)methyl)-6-(6-(trifluoromethyl)pyridin-3-yl)phenol dihydrochloride (190 mg, 25% yield) as a white powder.

HPLC/MS R$_t$=3.5 min, m/z 424.4 (M+H$^+$); analysis calculated for C$_{23}$H$_{32}$F$_3$N$_3$O-2HCl: C, 55.65; H, 6.90; N, 8.46; Cl, 14.28. found: C, 55.81; H, 6.84; N, 8.47; Cl, 14.45. $^1$H NMR (400 MHz, DMSO-d$_6$) δ 10.97 (bs, 1H), 9.70 (bs, 2H), 9.38 (bs, 1H), 8.91 (s, 1H), 8.21 (d, J=8.2 Hz, 1H), 7.98 (d, J=8.2 Hz, 1H), 7.70 (d, J=2.5 Hz, 1H), 7.41 (d, J=2.5 Hz, 1H), 4.30 (s, 2H), 3.59-3.45 (m, 4H), 3.20 (q, J=6.7 Hz, 4H), 1.31 (s, 9H) and 1.27 (t, J=1.27 Hz, 6H).

Example 64

2-(Aminomethyl)-4-(tert-butyl)-6-(6-(trifluoromethyl)pyridin-3-yl)phenol hydrochloride

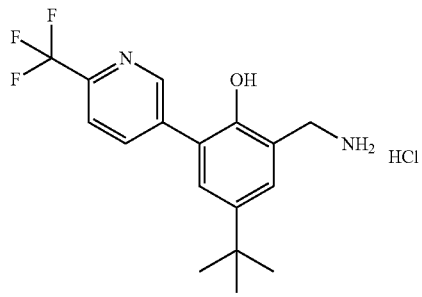 [SMILES: CC(C)(C)c1cc(CN)c(O)c(-c2ccc(C(F)(F)F)nc2)c1 ; Cl]

Step 1: 5-(tert-Butyl)-2-hydroxy-3-(6-(trifluoromethyl)pyridin-3-yl)benzaldehyde oxime Following the patent procedure of C. G. Luca (US 20050137168), hydroxylamine hydrochloride (355 mg, 5.11 mmol) was added to a solution of 5-(tert-butyl)-2-hydroxy-3-(6-(trifluoromethyl)pyridin-3-yl)benzaldehyde (from Example 47, Step 1) (1.5 g, 4.64 mmol) and sodium acetate (419 mg, 5.11 mmol) in ethanol (15 mL). The reaction was stirred at room temperature for 16 hours. The mixture was partitioned between water and ethyl acetate and the organic phase separated, dried ($Na_2SO_4$), filtered and the solvent removed under reduced pressure. The residue was purified using flash chromatography on silica eluting with a solvent gradient of 0 to 100% ethyl acetate in hexanes to give 5-(tert-butyl)-2-hydroxy-3-(6-(trifluoromethyl)pyridin-3-yl)benzaldehyde oxime (1.3 g, 83% yield).

HPLC/MS $R_t$=7.2 min, m/z 339.2 (M+H$^+$); analysis calculated for $C_{12}H_{12}F_3N_2O$: C, 60.35; H, 5.06; N, 8.28. found: C, 60.07; H, 4.86; N, 8.06. $^1$H NMR (500 MHz, DMSO-d$_6$) δ 11.68 (s, 1H), 10.72 (s, 1H), 8.97 (d, J=2.1 Hz, 1H), 8.50 (s, 1H), 8.27 (dd, J=8.2, 2.1 Hz, 1H), 7.97 (d, J=8.2 Hz, 1H), 7.57 (d, J=2.4 Hz, 1H), 7.44 (d, J=2.4 Hz, 1H), and 1.31 (s, 9H).

Step 2: 2-(Aminomethyl)-4-(tert-butyl)-6-(6-(trifluoromethyl)pyridin-3-yl)phenol hydrochloride Following the patent procedure of C. G. Luca (US 20050137168), zinc (1.9 g, 29.3 mmol) was added to a stirred solution of 5-(tert-butyl)-2-hydroxy-3-(6-(trifluoromethyl)pyridin-3-yl)benzaldehyde oxime (1.1 g, 3.25 mmol) in acetic acid (10 mL) at 65° C. After 1 hour, the reaction was cooled, filtered and the zinc cake was rinsed with acetic acid (5 mL). The filtrate was concentrated under reduced pressure and the residue was taken up in a 1N solution of aqueous HCl and again the solvent was removed under reduced pressure. The mixture was then azeotropically dried with ethanol (10 mL), and toluene (2×10 mL), and finally the residue was triturated with ether in which it was slightly soluble initially to give 2-(aminomethyl)-4-(tert-butyl)-6-(6-(trifluoromethyl)pyridin-3-yl)phenol hydrochloride (416 mg, 35%).

HPLC/MS $R_t$=3.4 min, m/z 325.2 (M+H$^+$); $^1$H NMR (500 MHz, DMSO-d$_6$) δ 9.29 (s, 1H), 8.88 (d, J=1.7 Hz, 1H), 8.29 (bs, 3H), 8.18 (dd, J=8.0, 1.7 Hz, 1H), 7.98 (d, J=8.0 Hz, 1H), 7.55 (d, J=2.4 Hz, 1H), 7.36 (d, J=2.4 Hz, 1H), 4.10 (d, J=5.0 Hz, 2H), and 1.31 (s, 9H).

Example 65

2-(((1-Aminopropan-2-yl)amino)methyl)-4-(tert-butyl)-6-(6-(trifluoromethyl)pyridin-3-yl)phenol dihydrochloride

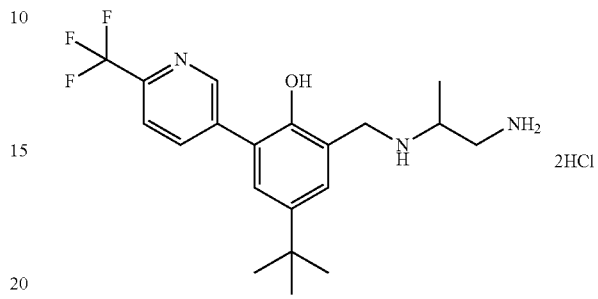

The free base of 2-(aminomethyl)-4-(tert-butyl)-6-(6-(trifluoromethyl)pyridin-3-yl)phenol hydrochloride (Example 64), was prepared by partitioning the hydrochloride salt (560 mg, 1.55 mmol) between ethyl acetate and a saturated aqueous sodium bicarbonate solution. The organic phase was separated, dried ($Na_2SO_4$), filtered and the solvent removed under reduced pressure. The residue was redissolved in a solution of tert-butyl (2-oxopropyl)carbamate in ethanol (5 mL) and stirred for three days. Sodium borohydride (290 mg, 7.75 mmol) was added portionwise and the reaction mixture stirred at room temperature for one hour. The reaction was quenched with saturated aqueous ammonium chloride solution (1 mL) and the reaction mixture partitioned between ethyl acetate and a saturated aqueous sodium bicarbonate solution. The organic phase was separated, dried ($Na_2SO_4$), filtered and the solvent was removed under reduced pressure. The residue was purified using flash chromatography on silica eluting with a solvent gradient of 0-100% ethyl acetate in hexanes to give tert-butyl (2-((5-(tert-butyl)-2-hydroxy-3-(6-(trifluoromethyl)pyridin-3-yl)benzyl)amino)propyl)carbamate (500 mg, 67%) as a white solid. The carbamate (500 mg, 1.04 mmol) was dissolved in methylene chloride (20 mL) and trifluoroacetic acid (10 mL) added and the reaction was stirred for 16 h. The solvent was removed under reduced pressure, the residue azeotroped twice with toluene (20 mL) and then redissolved in a 1:1 mixture of methylene chloride and trifluoracetic acid (40 mL) and stirred at room temperature for four hours. The solvent was removed under reduced pressure, the residue azeotroped twice with toluene (20 mL) and the residue partitioned between ethyl acetate and saturated aqueous sodium bicarbonate solution. The organic phase was separated, dried ($Na_2SO_4$), filtered and the solvent removed under pressure. The residue was purified using flash chromatography on silica eluting with a solvent gradient of 0 to 100% of (89% methylene chloride, 10% methanol and 1% ammonium hydroxide) in methylene chloride. The purified residue was dissolved in a 1.25 M hydrochloric acid solution in ethanol, the solution stood for 10 minutes, and then the solvent removed under reduced pressure and the residue triturated with diethyl ether to give 2-(((1-aminopropan-2-yl)amino)methyl)-4-(tert-butyl)-6-(6-(trifluoromethyl)pyridin-3-yl)phenol dihydrochloride (150 mg, 32% yield) as a white solid.

HPLC/MS $R_t$=0.9 min, m/z 382.4 (M+H$^+$); $^1$H NMR (500 MHz, DMSO-d$_6$) δ 9.53 (bs, 2H), 9.35 (s, 1H), 8.90 (d, J=1.9 Hz, 1H), 8.43 (bs, 3H), 8.20 (dd, J=8.1, 1.9 Hz, 1H), 7.99 (d, J=8.1 Hz, 1H), 7.73 (d, J=2.6 Hz, 1H) 7.40 (d, J=2.6 Hz, 1H), 4.36-4.22 (m, 2H), 3.68-3.58 (m, 1H), 3.40-3.30 (m, 1H), 3.20-3.09 (m, 1H), 1.45 (d, J=6.7 Hz, 3H), and 1.31 (s, 9H).

Example 66

3-((tert-Butylamino)methyl)-4'-fluoro-5-(6-(trifluoromethyl)pyridin-3-yl)-[1,1'-biphenyl]-4-ol hydrochloride

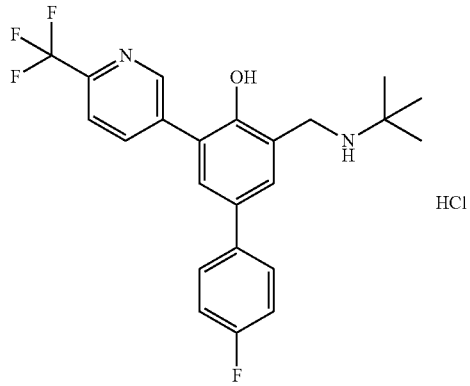 [SMILES: CC(C)(C)NCc1cc(-c2ccc(F)cc2)cc(-c2ccc(C(F)(F)F)nc2)c1O ; Cl]

Step 1: 3-Bromo-4'-fluoro-[1,1'-biphenyl]-4-ol

A solution of bromine (4.57 g, 28.59 mmol) in dichloromethane (20 mL) was added dropwise to a solution of 4-fluoro-4'-hydroxybiphenyl [purchased from TCI] (5.38 g, 28.59 mmol) in dichloromethane (100 mL) and acetonitrile (20 mL) and the reaction mixture stirred at room temperature under nitrogen for 18 hours. The reaction mixture was washed with saturated aqueous sodium hydrogen carbonate solution (200 mL) containing 10% aqueous sodium thiosulfate solution (20 mL), water (200 mL) and saturated brine (200 mL), dried (MgSO$_4$), filtered and concentrated in vacuo to give crude 3-bromo-4'-fluoro-[1,1'-biphenyl]-4-ol (9.0 g) as a tan solid.

HPLC/MS $R_t$=5.84 min, m/z 265.1 and 267.1 (M−H$^-$).

Step 2: 8-Bromo-3-(tert-butyl)-6-(4-fluorophenyl)-3,4-dihydro-2H-benzo[e][1,3]oxazine A mixture of paraformaldehyde (4.29 g, 0.143 mol) and tert-butylamine (15.1 mL, 0.143 mol) in isopropanol (40 mL) was stirred at 80° C. under nitrogen for 1 hour. A solution of 3-bromo-4'-fluoro-[1,1'-biphenyl]-4-ol (~28.59 mmol) in isopropanol (10 mL) was then added and the reaction mixture stirred at 80° C. for 3 days. The reaction mixture was allowed to cool to room temperature, the resulting thick orange slurry diluted with isopropanol (50 mL), stirred for 2 hours then filtered to give a yellow fluffy solid (6.52 g). Methanol (100 mL) was added and the resulting suspension stirred vigorously overnight then filtered to give 8-bromo-3-(tert-butyl)-6-(4-fluorophenyl)-3,4-dihydro-2H-benzo[e][1,3]oxazine (5.35 g, 51% yield) as a cream solid.

HPLC/MS $R_t$=1.86 min, m/z 352.2 and 354.2 (M+H$^+$ of hydrolysed product).

Step 3: 3-(tert-Butyl)-6-(4-fluorophenyl)-8-(6-(trifluoromethyl)pyridin-3-yl)-3,4-dihydro-2H-benzo[e][1,3]oxazine A mixture of 8-bromo-3-(tert-butyl)-6-(4-fluorophenyl)-3,4-dihydro-2H-benzo[e][1,3]oxazine (2.0 g, 5.49 mmol), 2-(trifluoromethyl)pyridine-5-boronic acid [purchased from Frontier Scientific] (1.26 g, 6.59 mmol) and potassium carbonate (1.52 g, 10.98 mmol) in dimethoxyethane (15 mL) and water (5 mL) was purged with nitrogen for 20 minutes. Tetrakis(triphenylphosphine)palladium(0) (317.2 mg, 0.275 mmol) was added and the reaction mixture heated at 80° C. in a sealed vial for 17 hours. The cooled reaction mixture was partitioned between ethyl acetate (80 mL) and 1.0 M aqueous sodium hydroxide solution (80 mL), the organic phase separated, washed with water (80 mL) and saturated brine (80 mL), dried (MgSO$_4$), filtered and concentrated under reduced pressure to give an orange syrup. The crude product was purified by chromatography on silica eluting with a solvent gradient of 0 to 8% methanol (containing 1% aqueous ammonium hydroxide) in dichloromethane to give 3-(tert-butyl)-6-(4-fluorophenyl)-8-(6-(trifluoromethyl)pyridin-3-yl)-3,4-dihydro-2H-benzo[e][1,3]oxazine (0.773 g, 37% yield) as a colorless syrup.

HPLC/MS $R_t$=4.37 min, m/z 419.4 (M+H$^+$ of hydrolysed product).

Step 4: 3-((tert-Butylamino)methyl)-4'-fluoro-5-(6-(trifluoromethyl)pyridin-3-yl)-[1,1'-biphenyl]-4-ol hydrochloride A solution of 3-(tert-butyl)-6-(4-fluorophenyl)-8-(6-(trifluoromethyl)pyridin-3-yl)-3,4-dihydro-2H-benzo[e][1,3] oxazine (0.773 g, 1.796 mmol) in ethanol (80 mL) and 1.0 M aqueous hydrochloric acid (40 mL) was stirred at room temperature for 6 days. The reaction mixture was concentrated under reduced pressure to remove ethanol and the resulting aqueous suspension partitioned between ethyl acetate (100 mL) and saturated aqueous sodium hydrogen carbonate solution (100 mL). The organic phase was separated, washed with water (80 mL) and saturated brine (80 mL), dried (MgSO$_4$), filtered and concentrated under reduced pressure to afford a yellow syrup. The product was purified using flash chromatography on silica eluting with a solvent gradient of 0 to 50% ethyl acetate (containing 2% methanol) in hexanes to give the product as a yellow syrup (0.599 g, 80% yield). The product was dissolved in absolute ethanol (50 mL), 1.25 M hydrochloric acid in ethanol (4.45 mL, 5.565 mmol) added, the mixture stood for 20 minutes then concentrated under reduced pressure to give a yellow solid. The product was dissolved in ethanol (10 mL), diethyl ether (20 mL) added slowly and the resulting suspension stirred vigorously overnight then filtered to afford 3-((tert-butylamino)methyl)-4'-fluoro-5-(6-(trifluoromethyl)pyridin-3-yl)-[1,1'-biphenyl]-4-ol hydrochloride (0.5948 g, 73% yield) as a white solid.

HPLC/MS $R_t$=4.40 min, m/z 419.5 (M+H$^+$); analysis calculated for $C_{23}H_{22}F_4N_2O$ HCl: C, 60.73; H, 5.10; N, 6.16; Cl, 7.79. found: C, 60.62; H, 4.95; N, 6.03; Cl, 7.84.

Example 67

3-((tert-Butylamino)methyl)-3'-fluoro-5-(6-(trifluoromethyl)pyridin-3-yl)-[1,1'-biphenyl]-4-ol hydrochloride

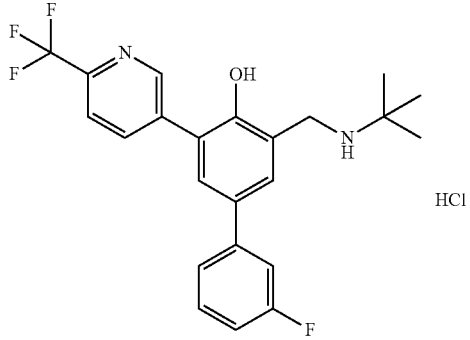 [SMILES: CC(C)(C)NCc1cc(-c2cccc(F)c2)cc(-c2ccc(C(F)(F)F)nc2)c1O ; Cl]

Step 1: 3-Bromo-3'-fluoro-[1,1'-biphenyl]-4-ol

A solution of bromine (887 mg, 5.55 mmol) in dichloromethane (10 mL) was added dropwise to a solution of 4-(3-fluorophenyl)phenol [purchased from Combi-Blocks] (1.044 g, 5.55 mmol) in dichloromethane (10 mL) and acetonitrile (5 mL) at 0° C. under nitrogen. The reaction mixture was then stirred at 0° C. to room temperature for 17 hours. The reaction mixture was partitioned between ethyl acetate (100 mL) and saturated aqueous sodium hydrogen carbonate solution (100 mL) containing 10% aqueous sodium thiosulfate solution (10 mL). The organic phase was separated, washed with water (100 mL) and saturated brine (100 mL), dried ($MgSO_4$), filtered and concentrated under reduced pressure to give an orange oil. The crude product was purified by chromatography on silica eluting with a solvent gradient of 0 to 15% ethyl acetate (containing 2% methanol) in hexanes to give 3-bromo-3'-fluoro-[1,1'-biphenyl]-4-ol (1.56 g, quant.) as a colorless oil.

HPLC/MS $R_t$=5.85 min, m/z 265.0 and 267.0 (M−H)⁻.

Step 2: 3-Bromo-3'-fluoro-4-((2-methoxyethoxy)methoxy)-1,1'-biphenyl

2-Methoxyethoxymethylchloride (0.67 mL, 5.83 mmol) was added dropwise to a solution of 3-bromo-3'-fluoro-[1,1'-biphenyl]-4-ol (~5.55 mmol) and diisopropylethylamine (1.93 mL, 11.1 mmol) in dry dichloromethane (20 mL) at room temperature under nitrogen. The reaction mixture was stirred at room temperature under nitrogen for 3 days, 1.0 M aqueous sodium hydroxide (20 mL) added and the biphasic mixture stirred vigorously for 20 minutes. The reaction mixture was partitioned between ethyl acetate (100 mL) and 1.0 M aqueous sodium hydroxide solution (100 mL), the organic phase separated, washed with water (75 mL) and saturated brine (75 mL), dried ($MgSO_4$), filtered and concentrated under reduced pressure to give an orange oil. The crude product was purified by chromatography on silica eluting with a solvent gradient of 0 to 10% ethyl acetate (containing 2% methanol) in hexanes to give 3-bromo-3'-fluoro-4-((2-methoxyethoxy)methoxy)-1,1'-biphenyl (1.57 g, 80% yield) as a colorless oil.

HPLC/MS $R_t$=6.95 min.

Step 3: 5-(3'-Fluoro-4-((2-methoxyethoxy)methoxy)-[1,1'-biphenyl]-3-yl)-2-(trifluoromethyl)pyridine A mixture of 3-bromo-3'-fluoro-4-((2-methoxyethoxy)methoxy)-1,1'-biphenyl (1.56 g, 4.39 mmol), 2-(trifluoromethyl)pyridine-5-boronic acid [purchased from Frontier Scientific] (1.09 g, 5.709 mmol) and potassium carbonate (0.91 g, 6.59 mmol) in dimethoxyethane (15 mL) and water (5 mL) was purged with nitrogen for 20 minutes. Tetrakis(triphenylphosphine)palladium(0) (253.8 mg, 0.22 mmol) was added and the reaction mixture heated at 80° C. in a sealed vial for 2 days. The cooled reaction mixture was partitioned between ethyl acetate (80 mL) and 1.0 M aqueous sodium hydroxide solution (80 mL), the organic phase separated, washed with water (80 mL) and saturated brine (80 mL), dried ($MgSO_4$), filtered and concentrated under reduced pressure to give a yellow syrup. The crude product was purified by chromatography on silica eluting with a solvent gradient of 0 to 20% ethyl acetate (containing 2% methanol) in hexanes to give 5-(3'-fluoro-4-((2-methoxyethoxy)methoxy)-[1,1'-biphenyl]-3-yl)-2-(trifluoromethyl)pyridine (1.62 g, 88% yield) as a yellow syrup.

HPLC/MS $R_t$=7.40 min, m/z 422.2 (M+H⁺).

Step 4: 3'-Fluoro-3-(6-(trifluoromethyl)pyridin-3-yl)-[1,1'-biphenyl]-4-ol

A solution of 5-(3'-fluoro-4-((2-methoxyethoxy)methoxy)-[1,1'-biphenyl]-3-yl)-2-(trifluoromethyl)pyridine (1.61 g, 3.82 mmol) in methanol (100 mL) and 1.0 M aqueous hydrochloric acid (50 mL) was stirred at 60° C. for 2 days. The cooled reaction mixture was concentrated under reduced pressure to remove methanol, and the resulting aqueous suspension partitioned between ethyl acetate (100 mL) and saturated aqueous sodium hydrogen carbonate solution (100 mL). The organic phase was separated, washed with water (75 mL) and saturated brine (75 mL), dried ($MgSO_4$), filtered and concentrated under reduced pressure to give a cream solid. The crude product was purified by chromatography on silica eluting with a solvent gradient of 0 to 50% ethyl acetate (containing 2% methanol) in hexanes to give 3'-fluoro-3-(6-(trifluoromethyl)pyridin-3-yl)-[1,1'-biphenyl]-4-ol (1.04 g, 81% yield) as a white crystalline solid.

HPLC/MS $R_t$=6.55 min, m/z 334.2 (M+H⁺).

Step 5: 3-((tert-Butylamino)methyl)-3'-fluoro-5-(6-(trifluoromethyl)pyridin-3-yl)-[1,1'-biphenyl]-4-ol hydrochloride A mixture of paraformaldehyde (0.46 g, 15.30 mmol) and tert-butylamine (1.615 mL, 15.30 mmol) in isopropanol (10 mL) was stirred at 80° C. under nitrogen for 1 hour.

A solution of 3'-fluoro-3-(6-(trifluoromethyl)pyridin-3-yl)-[1,1'-biphenyl]-4-ol (1.02 g, 3.06 mmol) in isopropanol (20 mL) was then added and the reaction mixture stirred at 80° C. for 2 days. The cooled reaction mixture was concentrated under reduced pressure and the residue azeotroped with isopropanol (30 mL) to give a yellow syrup. The crude product was partitioned between ethyl acetate (80 mL) and 1.0 M aqueous sodium hydroxide solution (100 mL), the organic phase separated, washed with water (80 mL) and saturated brine (80 mL), dried ($MgSO_4$), filtered and concentrated under reduced pressure to give a yellow syrup (1.55 g). The crude 3,4-dihydro-2H-benzo[e][1,3]oxazine (1.55 g) was dissolved in ethanol (100 mL), 1.0 M aqueous hydrochloric acid solution (50 mL) was added and the reaction mixture stirred at room temperature for 7 days. The reaction mixture was concentrated under reduced pressure to remove ethanol, the resulting aqueous suspension partitioned between ethyl acetate (80 mL) and saturated aqueous sodium hydrogen carbonate solution (80 mL). The organic phase was separated, washed with water (80 mL) and saturated brine (80 mL), dried ($MgSO_4$), filtered and concentrated under reduced pressure to give a yellow solid. The crude product was purified by chromatography on silica eluting with a solvent gradient of 0 to 40% ethyl acetate (containing 2% methanol) in hexanes to give the product as a cream solid (1.18 g, 92% yield). The product was dissolved in absolute ethanol (50 mL), 1.25 M hydrochloric acid in ethanol (9.06 mL, 11.32 mmol) added, the mixture stood for 20 minutes then concentrated under reduced pressure to give a yellow foam. The product was dissolved in ethanol (5 mL), diethyl ether (30 mL) added slowly and the resulting suspension stirred vigorously overnight then filtered to afford 3-((tert-butylamino)methyl)-3'-fluoro-5-(6-(trifluoromethyl)pyridin-3-yl)-[1,1'-biphenyl]-4-ol hydrochloride (1.07 g, 77% yield) as a white solid.

HPLC/MS $R_t$=5.86 min, m/z 419.1 (M+H⁺); analysis calculated for $C_{23}H_{22}F_4N_2O$ HCl: C, 60.73; H, 5.10; N, 6.16; Cl, 7.79. found: C, 60.95; H, 4.96; N, 6.11; Cl, 7.91.

Example 68

2-((tert-Butylamino)methyl)-4-fluoro-6-(6-(trifluoromethyl)pyridin-3-yl)phenol hydrochloride

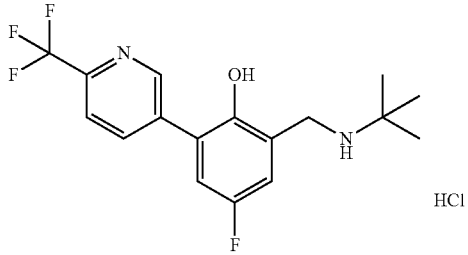 [SMILES: CC(C)(C)NCc1cc(F)cc(-c2ccc(C(F)(F)F)nc2)c1O ; Cl]

Step 1: 2-Bromo-4-fluoro-1-((2-methoxyethoxy)methoxy)benzene was prepared as a colorless oil using the same procedure as described in Example 67, Step 2, replacing 3-bromo-3'-fluoro-[1,1'-biphenyl]-4-ol with 2-bromo-4-fluorophenol [purchased from Combi-Blocks].

HPLC/MS $R_t$=5.27 min.

Step 2: 5-(5-Fluoro-2-((2-methoxyethoxy)methoxy)phenyl)-2-(trifluoromethyl)pyridine was prepared as a colorless oil using the same procedure as described in Example 67, Step 3, replacing 3-bromo-3'-fluoro-4-((2-methoxyethoxy)methoxy)-1,1'-biphenyl with 2-bromo-4-fluoro-1-((2-methoxyethoxy)methoxy)benzene.

HPLC/MS $R_t$=6.02 min, m/z 346.3 (M+H⁺).

Step 3: 4-Fluoro-2-(6-(trifluoromethyl)pyridin-3-yl)phenol was prepared as a white crystalline solid using the same procedure as described in Example 67, Step 4, replacing 5-(3'-fluoro-4-((2-methoxyethoxy)methoxy)-[1,1'-biphenyl]-3-yl)-2-(trifluoromethyl)pyridine with 5-(5-fluoro-2-((2-methoxyethoxy)methoxy)phenyl)-2-(trifluoromethyl)pyridine.

HPLC/MS $R_t$=5.19 min, m/z 258.1 (M+H⁺).

Step 4: 2-((tert-Butylamino)methyl)-4-fluoro-6-(6-(trifluoromethyl)pyridin-3-yl)phenol hydrochloride was prepared as a white solid using the same procedure as described in Example 67, Step 5, replacing 3'-fluoro-3-(6-(trifluoromethyl)pyridin-3-yl)-[1,1'-biphenyl]-4-ol with 4-fluoro-2-(6-(trifluoromethyl)pyridin-3-yl)phenol.

HPLC/MS $R_t$=2.03 min, m/z 343.1 (M+H⁺); analysis calculated for $C_{17}H_{18}F_4N_2O$ HCl: C, 53.90; H, 5.06; N, 7.40; Cl, 9.36. found: C, 53.87; H, 5.29; N, 7.11; Cl, 9.28.

Example 69

2-((tert-Butylamino)methyl)-4-chloro-6-(6-(trifluoromethyl)pyridin-3-yl)phenol hydrochloride

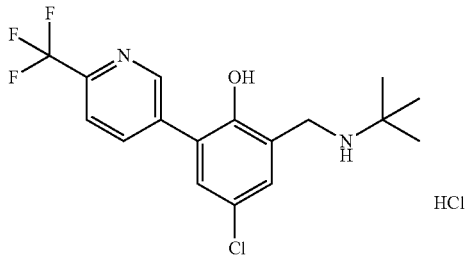 [SMILES: CC(C)(C)NCc1cc(Cl)cc(-c2ccc(C(F)(F)F)nc2)c1O ; Cl]

Step 1: 2-Bromo-4-chloro-1-((2-methoxyethoxy)methoxy)benzene was prepared as a colorless oil using the same procedure as described in Example 67, Step 2, replacing 3-bromo-3'-fluoro-[1,1'-biphenyl]-4-ol with 2-bromo-4-chlorophenol [purchased from Combi-Blocks].

HPLC/MS $R_t$=6.00 min.

Step 2: 5-(5-Chloro-2-((2-methoxyethoxy)methoxy)phenyl)-2-(trifluoromethyl)pyridine was prepared as a colorless oil using the same procedure as described in Example 67, Step 3, replacing 3-bromo-3'-fluoro-4-((2-methoxyethoxy)methoxy)-1,1'-biphenyl with 2-bromo-4-chloro-1-((2-methoxyethoxy)methoxy)benzene.

HPLC/MS $R_t$=6.62 min, m/z 362.0 and 364.0 (M+H⁺).

Step 3: 4-Chloro-2-(6-(trifluoromethyl)pyridin-3-yl)phenol was prepared as a white solid using the same procedure as described in Example 67, Step 4, replacing 5-(3'-fluoro-4-((2-methoxyethoxy)methoxy)-[1,1'-biphenyl]-3-yl)-2-(trifluoromethyl)pyridine with 5-(5-chloro-2-((2-methoxyethoxy)methoxy)phenyl)-2-(trifluoromethyl)pyridine.

HPLC/MS $R_t$=5.79 min, m/z 274.0 and 276.0 (M+H⁺).

Step 4: 2-((tert-Butylamino)methyl)-4-chloro-6-(6-(trifluoromethyl)pyridin-3-yl)phenol hydrochloride was prepared as a white solid using the same procedure as described in Example 67, Step 5, replacing 3'-fluoro-3-(6-(trifluoromethyl)pyridin-3-yl)-[1,1'-biphenyl]-4-ol with 4-chloro-2-(6-(trifluoromethyl)pyridin-3-yl)phenol.

HPLC/MS $R_t$=3.54 min, m/z 359.1 and 361.1 (M+H⁺); analysis calculated for $C_{17}H_{18}ClF_3N_2O$ HCl: C, 51.66; H, 4.85; N, 7.09; Cl, 17.94. found: C, 51.78; H, 4.84; N, 7.05; Cl 18.15.

Example 70

3-((tert-Butylamino)methyl)-4'-chloro-5-(6-(trifluoromethyl)pyridin-3-yl)-[1,1'-biphenyl]-4-ol hydrochloride

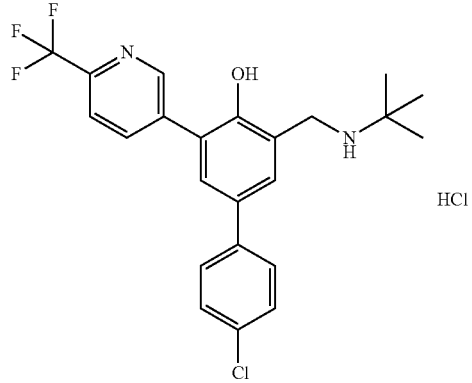 [SMILES: CC(C)(C)NCc1cc(-c2ccc(Cl)cc2)cc(-c2ccc(C(F)(F)F)nc2)c1O ; Cl]

Step 1: 3-Bromo-4'-chloro-[1,1'-biphenyl]-4-ol was prepared as a white solid using the same procedure as described in Example 67, Step 1, replacing 4-(3-fluorophenyl)phenol with 4-(4-chlorophenyl)phenol.

HPLC/MS $R_t$=6.47 min, m/z 281.0 and 283.0 (M−H)⁻.

Step 2: 3-Bromo-4'-chloro-4-((2-methoxyethoxy)methoxy)-1,1'-biphenyl was prepared as a colorless syrup using the same procedure as described in Example 67, Step 2, replacing 3-bromo-3'-fluoro-[1,1'-biphenyl]-4-ol with 3-bromo-4'-chloro-[1,1'-biphenyl]-4-ol.

HPLC/MS $R_t$=7.60 min.

Step 3: 5-(4'-Chloro-4-((2-methoxyethoxy)methoxy)-[1,1'-biphenyl]-3-yl)-2-(trifluoromethyl)pyridine was prepared as a yellow syrup using the same procedure as described in Example 67, Step 3, replacing 3-bromo-3'-fluoro-4-((2- methoxyethoxy)methoxy)-1,1'-biphenyl with 3-bromo-4'-chloro-4-((2-methoxyethoxy)methoxy)-1,1'-biphenyl.

HPLC/MS R$_t$=7.90 min, m/z 438.0 and 440.0 (M+H$^+$).

Step 4: 4'-Chloro-3-(6-(trifluoromethyl)pyridin-3-yl)-[1,1'-biphenyl]-4-ol was prepared as a white solid using the same procedure as described in Example 67, Step 4, replacing 5-(3'-fluoro-4-((2-methoxyethoxy)methoxy)-[1,1'-biphenyl]-3-yl)-2-(trifluoromethyl)pyridine with 5-(4'-chloro-4-((2-methoxyethoxy)methoxy)-[1,1'-biphenyl]-3-yl)-2-(trifluoromethyl)pyridine.

HPLC/MS R$_t$=7.11 min, m/z 350.3 and 352.3 (M+H$^+$).

Step 5: 3-((tert-Butylamino)methyl)-4'-chloro-5-(6-(trifluoromethyl)pyridin-3-yl)-[1,1'-biphenyl]-4-ol hydrochloride was prepared as a hygroscopic white solid using the same procedure as described in Example 67, Step 5, replacing 3'-fluoro-3-(6-(trifluoromethyl)pyridin-3-yl)-[1,1'-biphenyl]-4-ol with 4'-chloro-3-(6-(trifluoromethyl)pyridin-3-yl)-[1,1'-biphenyl]-4-ol.

HPLC/MS R$_t$=7.60 min, m/z 435.1 and 437.1 (M+H$^+$); analysis calculated for C$_{23}$H$_{22}$ClF$_3$N$_2$O HCl H$_2$O: C, 56.45; H, 5.15; N, 5.72; Cl, 14.49. found: C, 56.09; H, 5.14; N, 5.71, Cl 14.63.

Example 71

3-((tert-Butylamino)methyl)-4-hydroxy-5-(6-(trifluoromethyl)pyridin-3-yl)benzonitrile hydrochloride

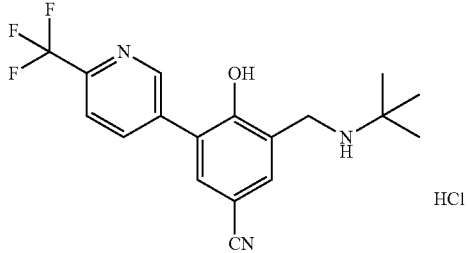 [SMILES: CC(C)(C)NCc1cc(C#N)cc(-c2ccc(C(F)(F)F)nc2)c1O ; Cl]

Step 1: 3-Bromo-4-((2-methoxyethoxy)methoxy)benzonitrile was prepared as a colorless syrup using the same procedure as described in Example 67, Step 2, replacing 3-bromo-3'-fluoro-[1,1'-biphenyl]-4-ol with 3-bromo-4-hydroxybenzonitrile [purchased from Combi-Blocks].

HPLC/MS R$_t$=4.59 min, m/z 286.1 and 288.1 (M+H$^+$).

Step 2: 4-((2-Methoxyethoxy)methoxy)-3-(6-(trifluoromethyl)pyridin-3-yl)benzonitrile was prepared as a yellow syrup using the same procedure as described in Example 67, Step 3, replacing 3-bromo-3'-fluoro-4-((2-methoxyethoxy)methoxy)-1,1'-biphenyl with 3-bromo-4-((2-methoxyethoxy)methoxy)benzonitrile.

HPLC/MS R$_t$=5.61 min, m/z 353.0 (M+H$^+$).

Step 3: 4-Hydroxy-3-(6-(trifluoromethyl)pyridin-3-yl)benzonitrile was prepared as a white solid using the same procedure as described in Example 67, Step 4, replacing 5-(3'-fluoro-4-((2-methoxyethoxy)methoxy)-[1,1'-biphenyl]-3-yl)-2-(trifluoromethyl)pyridine with 4-((2-methoxyethoxy)methoxy)-3-(6-(trifluoromethyl)pyridin-3-yl)benzonitrile.

HPLC/MS R$_t$=4.70 min, m/z 265.0 (M+H$^+$).

Step 4: 3-((tert-Butylamino)methyl)-4-hydroxy-5-(6-(trifluoromethyl)pyridin-3-yl)benzonitrile hydrochloride was prepared as a white solid using the same procedure as described in Example 67, Step 5, replacing 3'-fluoro-3-(6-(trifluoromethyl)pyridin-3-yl)-[1,1'-biphenyl]-4-ol with 4-hydroxy-3-(6-(trifluoromethyl)pyridin-3-yl)benzonitrile.

HPLC/MS R$_t$=2.56 min, m/z 438.5 (M+H$^+$); analysis calculated for C$_{24}$H$_{34}$F$_3$N$_3$O 2HCl: C, 56.47; H, 7.11; N, 8.23; Cl, 13.89. found: C, 56.46; H, 6.99; N, 8.21; Cl, 14.01.

HPLC/MS R$_t$=2.41 min, m/z 350.1 (M+H$^+$); analysis calculated for C$_{18}$H$_{18}$F$_3$N$_3$O HCl: C, 56.04; H, 4.96; N, 10.89, Cl 9.19. found: C, 56.22; H, 5.11; N, 10.91, Cl 9.25.

Example 72

2-((tert-Butylamino)methyl)-4-(methylsulfonyl)-6-(6-(trifluoromethyl)pyridin-3-yl)phenol hydrochloride

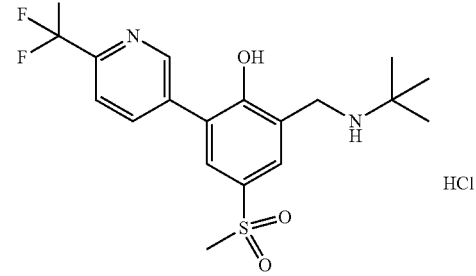

Step 1: 2-Bromo-4-(methylsulfonyl)phenol

A solution of bromine (9.28 g, 0.058 mol) in dichloromethane (20 mL) was added dropwise to a mixture of 4-methylsulfonylphenol (10 g, 0.058 mol) and sodium acetate (7.15 g, 0.087 mol) in dichloromethane (200 mL) and acetic acid (20 mL) at room temperature under nitrogen over 1 hour. The reaction mixture was washed with saturated aqueous sodium hydrogen carbonate solution (2×500 mL), precipitated solid was removed by filtration, and saturated brine (300 mL), dried (MgSO$_4$), filtered and concentrated under reduced pressure to give a white solid (4.3 g). Water (100 mL) was added to the solid product and the resulting suspension stirred vigorously overnight then filtered to give a white solid (3.64 g). The crude product was purified by chromatography on silica eluting with a solvent gradient of 40 to 50% ethyl acetate (containing 2% methanol) in hexanes to give 2-bromo-4-(methylsulfonyl)phenol (2.3 g, 16% yield) as a white solid.

HPLC/MS R$_t$=1.42 min, m/z 249 and 251 (M−H)$^-$.

Step 2: 2-Bromo-1-((2-methoxyethoxy)methoxy)-4-(methylsulfonyl)benzene was prepared as a colorless syrup using the same procedure as described in Example 67, Step 2, replacing 3-bromo-3'-fluoro-[1,1'-biphenyl]-4-ol with 2-bromo-4-(methylsulfonyl)phenol.

HPLC/MS R$_t$=3.31 min.

Step 3: 5-(2-((2-Methoxyethoxy)methoxy)-5-(methylsulfonyl)phenyl)-2-(trifluoromethyl)pyridine was prepared as an olive solid using the same procedure as described in Example 67, Step 3, replacing 3-bromo-3'-fluoro-4-((2-methoxyethoxy)methoxy)-1,1'-biphenyl with 2-bromo-1-((2-methoxyethoxy)methoxy)-4-(methylsulfonyl)benzene.

HPLC/MS R$_t$=4.65 min, m/z 406.0 (M+H$^+$).

Step 4: 4-(Methylsulfonyl)-2-(6-(trifluoromethyl)pyridin-3-yl)phenol was prepared as a cream solid using the same procedure as described in Example 67, Step 4, replacing 5-(3'-fluoro-4-((2-methoxyethoxy)methoxy)-[1,1'-biphenyl]-3-yl)-2-(trifluoromethyl)pyridine with 5-(2-((2-methoxyethoxy)methoxy)-5-(methylsulfonyl)phenyl)-2-(trifluoromethyl)pyridine.

HPLC/MS R$_t$=3.59 min, m/z 318.1 (M+H$^+$).

Step 5: 2-((tert-Butylamino)methyl)-4-(methylsulfonyl)-6-(6-(trifluoromethyl)pyridin-3-yl)phenol hydrochloride was prepared as a white solid using the same procedure as described in Example 67, Step 5, replacing 3'-fluoro-3-(6-(trifluoromethyl)pyridin-3-yl)-[1,1'-biphenyl]-4-ol with 4-(methylsulfonyl)-2-(6-(trifluoromethyl)pyridin-3-yl)phenol.

HPLC/MS $R_t$=1.89 min, m/z 403.0 (M+H$^+$); analysis calculated for $C_{18}H_{21}F_3N_2O_3S$ HCl: C, 49.26; H, 5.05; N, 6.38; Cl, 8.08. found: C, 49.24; H, 5.32; N, 6.08; Cl, 7.80.

Example 73

4-(tert-Butyl)-2-(1-(tert-butylamino)ethyl)-6-(6-(trifluoromethyl)pyridin-3-yl)phenol hydrochloride

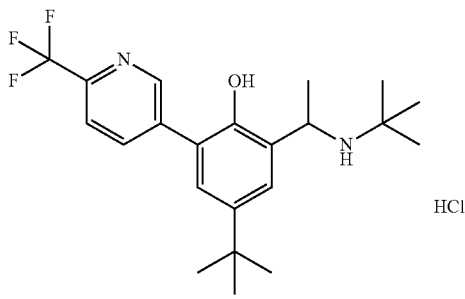 [SMILES: CC(NC(C)(C)C)c1cc(C(C)(C)C)cc(-c2ccc(C(F)(F)F)nc2)c1O ; Cl]

Step 1: 3-Bromo-5-(tert-butyl)-2-(methoxymethoxy)benzaldehyde

To a stirred solution of 3-bromo-5-(tert-butyl)-2-hydroxybenzaldehyde (5.80 g, 22.6 mmol) (Intermediate 8) and potassium carbonate (4.10 g, 29.4 mmol) in N,N-dimethylformamide (50 mL) at room temperature was added chloromethyl methyl ether (2.01 mL, 27.1 mmol) and the reaction mixture stirred for 3 days. The reaction mixture was partitioned between ethyl acetate and saturated aqueous sodium bicarbonate solution. The organic phase was separated, dried (Na$_2$SO$_4$), filtered, and the solvent removed under reduced pressure to give 3-bromo-5-(tert-butyl)-2-(methoxymethoxy)benzaldehyde (7.00 g, 100%+DMF) as a yellow oil.

HPLC/MS $R_t$=6.97 min, m/z 269.1 and 271.1 (M+H$^+$—OCH$_3$). $^1$H NMR (400 MHz, DMSO-d$_6$) δ 10.18 (d, J=0.4 Hz, 1H), 7.99 (d, J=2.4 Hz, 1H), 7.73 (d, J=7.73 Hz, 1H), 5.16 (s, 2H), 3.54 (s, 3H), and 1.29 (s, 9H).

Step 2: 5-(tert-Butyl)-2-(methoxymethoxy)-3-(6-(trifluoromethyl)pyridin-3-yl)benzaldehyde To a degassed (argon) solution of 3-bromo-5-(tert-butyl)-2-(methoxymethoxy)benzaldehyde (4.0 g, 13.3 mmol) and 2-(trifluoromethyl)pyridine-5-boronic acid [purchased from Frontier Scientific] (2.79 g, 14.6 mmol) in 2M aqueous sodium carbonate solution (26.7 mL, 53.2 mmol) and dimethoxy ethane (80 mL) was added tetrakis(triphenylphosphine)palladium(0) (770 mg, 0.665 mmol), the mixture was degassed for five minutes and then heated at 80° C. for 16 hours. The cooled reaction mixture was partitioned between ethyl acetate and saturated aqueous sodium bicarbonate solution. The organic phase was separated, dried (Na$_2$SO$_4$), filtered and concentrated under reduced pressure to give an orange syrup. The product was purified using flash chromatography on silica eluting with a solvent gradient of 0 to 100% ethyl acetate in hexanes to give the 5-(tert-butyl)-2-(methoxymethoxy)-3-(6-(trifluoromethyl)pyridin-3-yl)benzaldehyde (3.7 g, 76% yield) as a grey-green solid.

HPLC/MS $R_t$=7.23 min, m/z 368.3 (M+H$^+$).

Step 3: 1-(5-(tert-Butyl)-2-(methoxymethoxy)-3-(6-(trifluoromethyl)pyridin-3-yl)phenyl)ethan-1-ol To a solution of 5-(tert-butyl)-2-(methoxymethoxy)-3-(6-(trifluoromethyl)pyridin-3-yl)benzaldehyde (1.0 g, 2.72 mmol) in THF (15 mL) at −78° C. under argon was added a 3 M solution of methyl magnesium bromide in diethyl ether (1.0 mL, 3.0 mmol). The reaction mixture was stirred at −78° C. for 10 minutes and then the solution poured onto brine cooled to 0° C. forming a gel. The mixture was partitioned between ethyl acetate and saturated aqueous ammonium chloride solution. The organic phase was separated, dried (Na$_2$SO$_4$), filtered, and the solvent removed under reduced pressure to give 1-(5-(tert-butyl)-2-(methoxymethoxy)-3-(6-(trifluoromethyl)pyridin-3-yl)phenyl)ethan-1-ol (660 mg, 63% yield) as a tan oil.

HPLC/MS $R_t$=6.58 min, m/z 384.4 (M+H$^+$).

Step 4: 1-(5-(tert-Butyl)-2-(methoxymethoxy)-3-(6-(trifluoromethyl)pyridin-3-yl)phenyl)ethan-1-one To a solution of 1-(5-(tert-butyl)-2-(methoxymethoxy)-3-(6-(trifluoromethyl)pyridin-3-yl)phenyl)ethan-1-ol (529 mg, 1.38 mmol) and sodium bicarbonate (1.16 g, 13.8 mmol) in methylene chloride (40 mL) was added Dess Martin periodinane (3.00 g, 6.90 mmol) and the reaction stirred for 1 hour. The reaction mixture was poured onto a 1:1 mixture of saturated aqueous sodium sulfite solution (50 mL) and water (50 mL). The resulting mixture was extracted with ethyl acetate (150 mL). The organic phase was washed with 1 N aqueous sodium hydroxide solution (50 mL), and water (50 mL), an emulsion formed and saturated brine (100 mL) was added to separate layers. The organic phase was dried (MgSO$_4$), filtered and the solvent removed under reduced pressure. The residue was purified using flash chromatography on silica eluting with a solvent gradient of 0 to 100% ethyl acetate in hexanes to give 1-(5-(tert-butyl)-2-(methoxymethoxy)-3-(6-(trifluoromethyl)pyridin-3-yl)phenyl)ethan-1-one (526 mg, 100% yield) as a white solid.

HPLC/MS $R_t$=7.23 min, m/z 382.3 (M+H$^+$). $^1$H NMR (400 MHz, DMSO-d$_6$) δ 8.90 (d, J=2.5 Hz, 1H), 8.24 (dd, J=8.1, 1.6 Hz, 1H), 8.00 (d, J=8.1 Hz, 1H), 7.65 (d, J=2.6 Hz, 1H), 4.62 (s, 2H), 2.89 (s, 3H), 2.60 (s, 3H), and 1.31 (s, 9H).

Step 5: 1-(5-(tert-Butyl)-2-hydroxy-3-(6-(trifluoromethyl)pyridin-3-yl)phenyl)ethan-1-one To a solution of 1-(5-(tert-butyl)-2-(methoxymethoxy)-3-(6-(trifluoromethyl)pyridin-3-yl)phenyl)ethan-1-one (440 mg, 1.15 mmol) in methanol (5 mL) was added para-toluenesulfonic acid (330 mg, 1.72 mmol) and the reaction mixture heated to 40° C. After 30 minutes the reaction mixture was partitioned between ethyl acetate and saturated aqueous sodium bicarbonate solution. The organic phase was separated, dried (Na$_2$SO$_4$), filtered and purified by flash chromatography on silica eluting with 0-100% ethyl acetate in hexanes to yield 1-(5-(tert-butyl)-2-hydroxy-3-(6-(trifluoromethyl)pyridin-3-yl)phenyl)ethan-1-one (338 mg, 87%) as a cream colored solid.

HPLC/MS $R_t$=7.75 min, m/z 338.3 (M+H$^+$).

Step 6: 4-(tert-Butyl)-2-(1-(tert-butylamino)ethyl)-6-(6-(trifluoromethyl)pyridin-3-yl)phenol hydrochloride A solution of 1-(5-(tert-butyl)-2-hydroxy-3-(6-(trifluoromethyl)pyridin-3-yl)phenyl)ethan-1-one (310 mg, 0.92 mmol) in tert-butylamine (4 mL) was heated to 55° C. for 3 days, cooled to room temperature and sodium borohydride (170 mg, 4.59 mmol) was added. The reaction mixture was stirred for 30 minutes and then quenched by the slow addition of concentrated hydrochloric acid (0.4 mL, 4.7 mmol) at 0° C.

The reaction mixture was partitioned between ethyl acetate and saturated aqueous sodium bicarbonate solution. The organic phase was separated, dried (Na$_2$SO$_4$), filtered and the solvent removed under reduced pressure. The residue was purified using flash chromatography on silica gel eluting with 0-100% ethyl acetate in hexanes to yield 230 mg of product which was dissolved in a 1.25 M solution of HCl in ethanol (5 mL) and stirred for 30 minutes. The solvent was removed under reduced pressure and the solid triturated with diethyl ether to give 4-(tert-butyl)-2-(1-(tert-butylamino)ethyl)-6-(6-(trifluoromethyl)pyridin-3-yl)phenol hydrochloride (170 mg, 43%) as a white solid.

HPLC/MS R$_t$=4.2 min, m/z 395.4 (M+H$^+$); analysis calculated for C$_{22}$H$_{29}$F$_3$N$_2$O—HCl: C, 61.32; H, 7.02; N, 6.50; Cl, 8.23. found: C, 61.23; H, 7.18; N, 6.49; Cl, 8.36. $^1$H NMR (400 MHz, DMSO-d$_6$) δ 9.26 (s, 1H), 8.98 (d, J=9.0 Hz, 1H), 8.85 (s, 1H), 8.73 (bs, 1H), 8.16 (d, J=8.2 Hz, 1H), 7.95 (d, J=8.2 Hz, 1H), 7.82 (s, 1H), 7.28 (d, J=1.4 Hz, 1H), 4.90 (bs, 1H), 1.63 (d, J=6.6 Hz, 3H), 1.28 (s, 9H), and 1.21 (s, 9H).

Example 74

4-((tert-Butylamino)methyl)-6-(4-chlorophenyl)-6'-(trifluoromethyl)-[2,3'-bipyridin]-3-ol 1.1hydrochloride

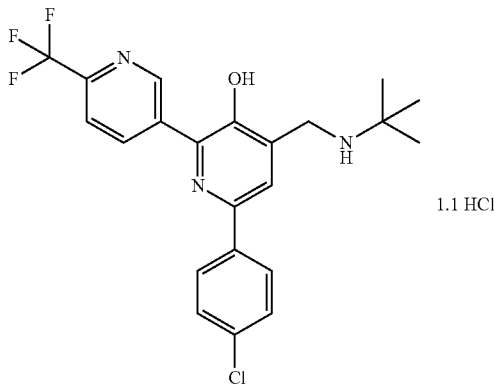 [SMILES: CC(C)(C)NCc1cc(-c2ccc(Cl)cc2)nc(-c2ccc(C(F)(F)F)nc2)c1O ; "1.1 HCl"]

1.1 HCl

Step 1: 2-Bromo-6-(4-chlorophenyl)pyridin-3-ol

A mixture of 2-bromo-6-iodopyridin-3-ol (0.65 g, 2.167 mmol), 4-chlorobenzeneboronic acid (339 mg, 2.167 mmol) and potassium carbonate (749 mg, 5.419 mmol) in dimethoxyethane (15 mL) and water (5 mL) was purged with nitrogen for 20 minutes. Tetrakis(triphenylphosphine)palladium(0) (125.2 mg, 0.108 mmol) was added and the reaction mixture heated to 80° C. in a sealed vial for 15 hours. The cooled reaction mixture was partitioned between ethyl acetate (50 mL) and saturated aqueous ammonium chloride solution (50 mL), the organic phase separated, washed with water (50 mL) and saturated brine (50 mL), dried (MgSO$_4$), filtered and concentrated under reduced pressure to give a yellow syrup. The crude product was purified by chromatography on silica eluting with a solvent gradient of 0 to 40% ethyl acetate in hexanes to give 2-bromo-6-(4-chlorophenyl)pyridin-3-ol (0.319 g, 52% yield) as a yellow crystalline solid.

HPLC/MS R$_t$=5.86 min, m/z 284.0, 286.0 and 288.0 (M+H$^+$).

Step 2: 6-(4-Chlorophenyl)-6'-(trifluoromethyl)-[2,3'-bipyridin]-3-ol

A mixture of 2-bromo-6-(4-chlorophenyl)pyridin-3-ol (0.319 g, 1.12 mmol), 2-(trifluoromethyl)pyridine-5-boronic acid [purchased from Frontier Scientific] (277.8 mg, 1.46 mmol) and potassium carbonate (386.7 mg, 2.798 mmol) in dimethoxyethane (15 mL) and water (5 mL) was purged with nitrogen for 20 minutes. Tetrakis(triphenylphosphine)palladium(0) (64.7 mg, 0.056 mmol) was added and the reaction mixture heated to 80° C. in a sealed vial for 15 hours. The cooled reaction mixture was partitioned between ethyl acetate (50 mL) and saturated aqueous ammonium chloride solution (50 mL), the organic phase separated, washed with water (50 mL) and saturated brine (50 mL), dried (MgSO$_4$), filtered and concentrated under reduced pressure to give a yellow solid. The crude product was purified by chromatography on silica eluting with a solvent gradient of 0 to 50% ethyl acetate in hexanes to give 6-(4-chlorophenyl)-6'-(trifluoromethyl)-[2,3'-bipyridin]-3-ol (0.234 g, 60% yield) as a cream solid.

HPLC/MS R$_t$=7.08 min, m/z 351.1 and 353.1 (M+H$^+$).

Step 3: 4-((tert-Butylamino)methyl)-6-(4-chlorophenyl)-6'-(trifluoromethyl)-[2,3'-bipyridin]-3-ol 1.1hydrochloride A mixture of paraformaldehyde (98.5 g, 3.28 mmol) and tert-butylamine (0.35 mL, 3.28 mmol) in isopropanol (3 mL) was stirred at 80° C. under nitrogen for 1 hour 20 minutes. A solution of 6-(4-chlorophenyl)-6'-(trifluoromethyl)-[2,3'-bipyridin]-3-ol (230 mg, 0.656 mmol) in isopropanol (5 mL) was then added and the reaction mixture stirred at 80° C. for 25 days. Additional paraformaldehyde (98.5 g, 3.28 mmol) and tert-butylamine (0.35 mL, 3.28 mmol) were added on days 7, 11 and 16. The cooled reaction mixture was concentrated under reduced pressure and the residue partitioned between ethyl acetate (60 mL) and water (60 mL). The organic phase was separated, washed with saturated brine (60 mL), dried (MgSO$_4$), filtered and concentrated under reduced pressure to give an orange syrup (0.26 g). The crude 3,4-dihydro-2H-benzo[e][1,3]oxazine (0.26 g) was dissolved in ethanol (20 mL), 1.0 M aqueous hydrochloric acid solution (10 mL) added and the reaction mixture stirred at room temperature for 4 days. The reaction mixture was concentrated under reduced pressure to remove ethanol, the resulting oily aqueous suspension partitioned between ethyl acetate (60 mL) and saturated aqueous sodium bicarbonate solution (60 mL). The organic phase was separated, washed with water (60 mL) and saturated brine (60 mL), dried (MgSO$_4$), filtered and concentrated under reduced pressure to give an orange syrup. The crude product was purified by chromatography on silica eluting with a solvent gradient of 0 to 100% ethyl acetate in hexanes to give the product as a cream solid (0.191 g, 67% yield). The product was dissolved in absolute ethanol (20 mL), 1.25 M hydrochloric acid in ethanol (2.1 mL, 2.63 mmol) added, the mixture stood for 20 minutes then concentrated under reduced pressure to give a yellow syrup. The product was dissolved in ethanol (3 mL), diethyl ether (20 mL) added slowly and the resulting suspension stirred vigorously overnight then filtered to afford 4-((tert-butylamino)methyl)-6-(4-chlorophenyl)-6'-(trifluoromethyl)-[2,3'-bipyridin]-3-ol 1.1hydrochloride (0.134 g, 43% yield) as a hygroscopic off-white solid.

HPLC/MS $R_f$=7.16 min, m/z 436.0 and 438.1 (M+H$^+$); analysis calculated for $C_{22}H_{21}ClF_3N_3O$ 1.1HCl 0.4H$_2$O: C, 54.69; H, 4.78; N, 8.70; Cl, 15.41. found: C, 54.74; H, 4.54; N, 8.57; Cl, 15.30.

Example 75

3,6-di-tert-Butyl-8-(6-(trifluoromethyl)pyridin-3-yl)-3,4-dihydro-2H-benzo[e][1,3]oxazine

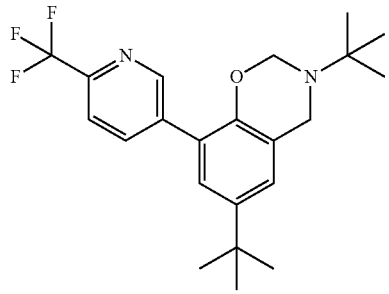 [SMILES: CC(C)(C)c1cc2c(c(-c3ccc(C(F)(F)F)nc3)c1)OCN(C(C)(C)C)C2]

The free base of 4-(tert-butyl)-2-((tert-butylamino)methyl)-6-(6-(trifluoromethyl)pyridin-3-yl)phenol hydrochloride (Example 1) was made by partitioning a solution of the hydrochloride salt (2.44 g, 5.85 mmol) between ethyl acetate and saturated aqueous sodium bicarbonate solution, the organic phase was separated, dried (MgSO$_4$), filtered and concentrated under reduced pressure.

The benzoxazine was synthesized following a procedure described by Cimarelli (Cimarelli, C., Palmieri, G. and Volpini, E. *Tetrahedron,* 2001, 57(28), 6089).

4-(tert-Butyl)-2-((tert-butylamino)methyl)-6-(6-(trifluoromethyl)pyridin-3-yl)phenol (2.00 g, 5.26 mmol) was added to a 37% aqueous solution of formaldehyde (0.47 mL, 5.78 mmol) in THF (6 mL) and the reaction mixture stirred at room temperature for 16 hours. The solvent was removed under reduced pressure and the solid was recrystallized by heating 1.1 g of product in methanol (10 mL) then cooling to room temperature to yield a first crop of 3,6-di-tert-butyl-8-(6-(trifluoromethyl)pyridin-3-yl)-3,4-dihydro-2H-benzo[e][1,3]oxazine (588 mg, 29%) as a white crystalline solid.

HPLC/MS $R_f$=4.4 min, m/z 381.4 (M+H$^+$ of hydrolysed product); $^1$H NMR (400 MHz, DMSO-d$_6$) δ 8.88 (d, J=1.9 Hz, 1H), 8.18 (dd, J=8.1, 1.9 Hz, 1H), 7.93 (d, J=8.1 Hz, 1H), 7.22 (d, J=2.3 Hz, 1H), 7.20 (d, J=2.3 Hz, 1H), 4.94 (s, 2H), 4.14 (s, 2H), 1.28 (s, 9H), and 1.14 (s, 9H).

*Plasmodium falciparum* Assay in Vitro

The potential for antimalarial activity against *Plasmodium falciparum* was determined by measuring the incorporation of tritiated hypoxanthine into parasitized red blood cells.

Compound Preparation and Administration

Stock solutions of the test compounds and the reference drug chloroquine (CQ) (Sigma Chemicals C-6628, Lot #059H0919) were prepared in silanized glass vials with AquaSil™ (Pierce, USA) to minimize absorption of the compounds to glassware. All test compounds were dissolved in DMSO (Sigma Cat No. #D8418) to 1 mM concentration, whereas CQ was dissolved in 50% methanol at a concentration of 1.6 mg/ml (base). Stock solutions were stored at −20° C.

Continuous In Vitro Cultivation of *Plasmodium falciparum*

*P. falciparum* Laboratory Lines

The *P. falciparum* laboratory adapted strains utilized in this project (Table 1) were in vitro cultured and routinely maintained in RPMI-1640-LPLF complete medium, which contained low concentrations of para-amino benzoic acid (0.0005 mg/L) and folic acid (0.01 mg/L).

TABLE 1

*Plasmodium falciparum* strains used in this project.

| Strain | Origin | Drug Resistance Profile |
|---|---|---|
| D6 | Sierra-Leone, Africa | Sensitive to chloroquine and pyrimethamine |
| W2 | Indochina | Resistant to chloroquine and pyrimethamine |

The low concentration of folic acid in RPMI-1640-LPLF prevents inhibition of the compound if its activity targets the parasite's folate metabolic pathway. Parasites were cultured in human red blood cells (RBCs) in vitro at 37° C. in special gas mixture (5% O$_2$, 5% CO$_2$ and 90% N$_2$) as described Trager and Jensen (1979 *Science* 193:673-675).

Preparation of Cultivation Medium

Base cultivation medium consisted of 10.4 g/L RPMI-1640-LPLF powder (Gibco BRL), 5.97 g/L HEPES buffer (MP Biomedicals, USA), 2.0 g/L D-glucose (BDH chemicals, Australia), 0.05 g/L hypoxanthine (Sigma, USA) and 40 mg/L gentamycin (Pfizer, Australia). The pH of the medium was adjusted to 6.9 and the solution was filtered using 0.2 μm pore size (AcroCap, Gelman Science, USA). Complete medium was prepared by adding sodium bicarbonate solution (final concentration, 0.21%) and drug-free heat-inactivated human plasma, pooled from various blood types, obtained from the Australian Red Cross Blood Service (Brisbane) (final concentration, 10%) to the base RPMI-1640-LPLF. For [$^3$H]-hypoxanthine inhibition growth assay, RPMI-1640-LPLF complete medium which lacked [$^3$H]-hypoxanthine ([$^3$H]-RPMI-1640-LPLF) was used to prevent uptake of hypoxanthine by parasites, as radioactive hypoxanthine uptake is measured as a surrogate marker of growth. All complete medium was used within three days of preparation. See DE (Para) SOP 002 for methodology.

Preparation of Red Blood Cells

Red blood cells (RBC) were required for *P. falciparum* parasites to proliferate in vitro. 0 (Rh+) type blood was obtained from the Australian Red Cross Blood Service. The RBC were washed twice in phosphate-buffered saline (PBS) and once in [$^3$H]-RPMI-1640-LPLF complete medium by centrifugation at 1,500×g for 5 min. Following the final wash, the haematocrit was measured as the percent of RBC to total culture volume. The haematocrit was adjusted to 50% by removing or adding [$^3$H]-RPMI-LPLF complete medium. See DE (Para) SOP 003 for methodology.

Continuous Cultivation of *P. falciparum* and Obtaining Synchronous Parasite Cultures for Drug Susceptibility Assays All *P. falciparum* strains were grown in RPMI-1640-LPLF complete medium at 4% haematocrit and 1% to 8% parasitaemia at 37° C. in sealed flasks in a gas mixture of 5% O$_2$, 5% CO$_2$ and 90% N$_2$ (BOC Gases, Brisbane, Australia). For drug susceptibility assays cultures were routinely synchronized when the majority of parasites (>85%) were at early trophozoite (ring) stage. Synchronization involved removing the more mature erythrocytic parasite stages by lysis, resulting in the retention only of early trophozoite (ring) stages. Synchronization was performed by re-suspending the infected red blood cell (iRBC) pellet in 5 to 10 times its volume of 5% D-sorbitol (Bacto Laboratories Pty. Ltd., Australia) for 5 min (Lambros and Vanderberg, 1979 *J Parasitol* 65: 418-420). The mixture was centrifuged (1,500 rpm for 5 min) and the supernatant removed. The iRBC were washed twice using PBS buffer and once using [$^3$H]-RPMI-LPLF plain medium. Following synchronization, a new culture was prepared with an initial parasitaemia of 1% in RPMI-LPLF complete medium. See DE (Para) SOP 008 for methodology.

Evaluation of In Vitro Antimalarial Activity of Test Compounds

[$^3$H]-Hypoxanthine Growth Inhibition Assay

The in vitro antimalarial activities of test compounds and reference compounds were assessed by exposing *P. falciparum* strains to ten serially diluted two-fold concentrations of each compound. The highest concentration of a compound on the plate ranged from 200 nM to 20,000 nM depending on its antimalarial activity. The stock solutions of the test compounds (made in DMSO) were diluted accordingly in complete [$^3$H]-media, containing 10% heat-inactivated plasma.

Parasite growth was measured by uptake of tritiated [$^3$H]-hypoxanthine into newly synthesized parasitic DNA. The [$^3$H]-hypoxanthine growth inhibition assay (Desjardins et al., 1979 *Antimicrobial Agents Chemother* 16: 710-718) was used to evaluate the in vitro antimalarial activity of the compounds. Briefly, synchronized parasite cultures (>90% rings, 4 to 8 h post invasion) in [$^3$H]-RPMI-LPLF complete medium with 1% parasitaemia and 2% haematocrit were exposed to the compounds at ten two-fold concentrations. Uninfected RBCs at 2% haematocrit were used as background controls. The plates were incubated in the gas mixture at 37° C. for approximately 24 h, followed by the addition of 0.2 µCi of $^3$H-hypoxanthine to each well and a further 24 h of incubation, and then frozen at −20° C. Plates were thawed and harvested using Tomtech Harvester 96 Mach III and radioactive counts were obtained using Wallac TriLux 1450 Microbeta Liquid Scintillation Counter (Perkin Elmer, USA). All assays were performed in triplicate for each strain and at least on two separate occasions.

Determination of In Vitro Inhibitory Concentrations of the Test Compounds

Tritiated hypoxanthine uptake data were analyzed in Graphpad Prism V5.0 software (GraphPad Software Inc. USA). The concentrations of the test compounds and chloroquine were transformed into logarithmic values. After subtracting the background values, the data from drug-treated wells were normalized against drug-free control wells. Non-linear regression analysis was carried out of the compound's concentration versus parasitic hypoxanthine incorporation. The in vitro antimalarial activity the compound is defined as inhibitory concentrations (IC$_{50}$) and that cause 50% inhibition of parasite growth as determined by measuring [$^3$H]-hypoxanthine incorporation.

In Vitro Antimalarial Activity of the Test Compounds

The in vitro antimalarial activities (expressed as IC$_{50}$) of the test compounds against the D6 and W2 lines of *P. falciparum* are shown in Table 2.

TABLE 2

In vitro antimalarial activities (IC$_{50}$) of test compounds and chloroquine against *P. falciparum* strains of D6 and W2.

| Example Number | D6 IC$_{50}$ (nM) | W2 IC$_{50}$ (nM) |
|---|---|---|
| Example 1 | 13 | 4 |
| Example 2 | 45 | 25 |
| Example 3 | 26 | 22 |
| Example 4 | 144 | 200 |
| Example 5 | 37 | 25 |
| Example 6 | 31 | 13 |
| Example 7 | 18 | 9 |
| Example 8 | 109 | 94 |
| Example 9 | 94 | 48 |
| Example 10 | 25 | 11 |
| Example 11 | 350 | 398 |
| Example 12 | 23 | 14 |
| Example 13 | 73 | 85 |
| Example 14 | 23 | 14 |
| Example 15 | 24 | 16 |
| Example 16 | 26 | 11 |
| Example 17 | 30 | 25 |
| Example 18 | 25 | 12 |
| Example 19 | ND | ND |
| Example 20 | 21 | 9 |
| Example 21 | 17 | 8 |
| Example 22 | 64 | 24 |
| Example 23 | 19 | 12 |
| Example 24 | ND | ND |
| Example 25 | 20000 | 20000 |
| Example 26 | 1333 | 598 |
| Example 27 | 6858 | 3442 |
| Example 28 | 357 | 111 |
| Example 29 | 192 | 68 |
| Example 30 | 67 | 42 |
| Example 31 | 5478 | 2269 |
| Example 32 | 38 | 11 |
| Example 33 | 10 | 3 |
| Example 34 | 8 | 2 |
| Example 35 | 549 | 144 |
| Example 36 | 779 | 401 |
| Example 37 | 5000 | 5000 |
| Example 38 | 7000 | 5000 |
| Example 39 | 73 | 42 |
| Example 40 | 231 | 79 |
| Example 41 | 10 | 3 |
| Example 42 | ND | ND |
| Example 43 | 158 | 100 |
| Example 44 | 11 | 6 |
| Example 45 | 275 | 106 |
| Example 46 | 2101 | 1973 |
| Example 47 | 43 | 31 |
| Example 48 | 5 | 5 |
| Example 49 | 244 | 214 |
| Example 50 | 297 | 160 |
| Example 51 | 46 | 24 |
| Example 52 | 23 | 14 |
| Example 53 | 3656 | 2292 |
| Example 54 | 6321 | 6120 |
| Example 55 | 2502 | 4000 |
| Example 56 | 104 | 117 |
| Example 57 | 34 | 29 |
| Example 58 | 1024 | 541 |
| Example 59 | 87 | 97 |
| Example 60 | 134 | 175 |
| Example 61 | 44 | 32 |
| Example 62 | 133 | 223 |
| Example 63 | 9 | 7 |
| Example 64 | 216 | 202 |
| Example 65 | 394 | 210 |
| Example 66 | 70 | 41 |
| Example 67 | 100 | 53 |
| Example 68 | 221 | 126 |
| Example 69 | 239 | 130 |
| Example 70 | 90 | 48 |
| Example 71 | 93082 | 50677 |
| Example 72 | 125056 | 81587 |
| Example 73 | 1861 | 2742 |
| Example 74 | 54 | 23 |
| Example 75 | 20 | 12 |
| Chloroquine | 12 | 133 |

Plasmodium berghei Assay in Vivo

In vivo antimalarial activity was tested in male or female Charles River CD-1 mice that were 4-5 weeks old and weighed 20-25 g They were housed in groups of 3 or 4 in standard plastic cages with wire tops, Bed-o-Cob® bedding, 12 hr/day of light, and maintained at 75° F. They were fed a standard Ralston Purina mouse chow and the cages and bottles were changed twice a week. Test compounds were ground in a mortar and pestle and diluted with enough vehicle to give a volume of 10 mL/kg of mouse weight. The oral doses were prepared in 0.5% hydroxyethylcellulose (Union Carbide Corp. WP 4400)/0.1% Tween-80 (Fisher Scientific T164-500). The amount of drug was calculated on the free base weight. The mice were infected intraperitoneally on day 0 with $5 \times 10^4$ erythrocytes parasitized with Plasmodium berghei (KBG-173 strain) from a donor mouse having a parasitemia between 5-10%. On days 3, 4 and 5 the test compounds were administered bid, spaced 6 hr apart, by oral gavage to the mice. Activity was measured by survival, with full activity defined as all animals living at day 31. Partial activity is defined as days of increased survival versus the infected non-treated controls. Results of the testing is shown in Table 3. This in vivo model is a modification of the Thompson Test. For further description see Ager, A. L, Jr. Rodent Malaria Models. In Handbook of Experimental Pharmacology: Antimalarial Drugs. 1. 68/1; Peters, W., Richards, W. H. G., Eds.: Springer-Verlag: Berlin, 1984, pp. 231-33.

| Compound | Dose in mg/kg/day | Number of mice alive at day 31 | Average Days Survival (Value in parentheses for the non-treated control) |
|---|---|---|---|
| Example 1 | 64 | 7/7 | >31* (8.7) |
|  | 32 | 7/7 | >31* (9.1) |
|  | 16 | 7/7 | >31* (9.1) |
|  | 8 | 7/7 | >31* (9.1) |
|  | 4 | 7/7 | >31* (9.1) |
|  | 2 | 5/7 | >27 (9.1) |
| Example 33 | 64 | 7/7 | >31* (8.1) |
|  | 32 | 7/7 | >31* (8.1) |
|  | 16 | 7/7 | >31* (8.1) |
|  | 8 | 7/7 | >31* (8.1) |
|  | 4 | 6/7 | >30 (8.1) |
| Example 34 | 64 | 7/7 | >31* (8.1) |
|  | 32 | 7/7 | >31* (8.1) |
|  | 16 | 7/7 | >31* (8.1) |
|  | 8 | 7/7 | >31* (8.1) |
|  | 4 | 6/7 | >28 (8.1) |
| Example 41 | 64 | 7/7 | >31* (8.7) |
|  | 32 | 7/7 | >31* (9.1) |
|  | 16 | 7/7 | >31* (9.1) |
|  | 8 | 7/7 | >31* (9.1) |
|  | 4 | 7/7 | >31* (9.1) |
| Example 44 | 64 | 7/7 | >31* (8.1) |
|  | 32 | 7/7 | >31* (8.1) |
|  | 16 | 7/7 | >31* (8.1) |
|  | 8 | 7/7 | >31* (8.1) |
|  | 4 | 7/7 | >31* (8.1) |
| Example 58 | 64 | 7/7 | >31* (7.4) |
|  | 32 | 6/7 | >26 (7.4) |
|  | 16 | 3/7 | >23.8 (7.4) |
|  | 8 | 3/7 | >20 (7.4) |
|  | 4 | 1/7 | >17.5 (7.4) |
| Example 66 | 64 | 6/7 | >7 (7.4) |
|  | 32 | 6/7 | >24 (7.4) |
|  | 16 | 7/7 | >31* (7.4) |
|  | 8 | 6/7 | >26 (7.4) |
|  | 4 | 1/7 | >21.3 (7.4) |
| Example 70 | 64 | 7/7 | >31* (7.3) |
|  | 32 | 7/7 | >31* (7.3) |
|  | 16 | 4/7 | >19 (7.3) |
|  | 8 | 5/7 | >21.5 (7.3) |
|  | 4 | 3/7 | >19.5 (7.3) |
| Example 75 | 64 | 7/7 | >31* (7.4) |
|  | 32 | 7/7 | >31* (7.4) |
|  | 16 | 7/7 | >31* (7.4) |
|  | 8 | 4/7 | >25 (7.4) |
|  | 4 | 4/7 | >22 (7.4) |
| Chloroquine | 128 | 4/7 | >21.3 (8.6) |
|  | 64 | 2/7 | >18.6 (8.6) |
|  | 16 | 1/7 | >18.8 (8.6) |
|  | 4 | 0/7 | 10.3 (8.6) |

*>31 means all animals survived to the end of the experiment. A > sign in front of a number <31 means some of the animals survived the 31 day experiment.

Effect on Cloned hERG Potassium Channels Expressed in Mammalian Cells

Drug-induced prolongation of the electrocardiographic QT interval (long QT syndrome) has been associated with an increased risk of a serious ventricular arrhythmia, torsade de pointes (Brown and Rampe, Pharmaceutical News 2000, 7, 15-20). Inhibition of $I_{Kr}$, a potassium current that controls cardiac action potential repolarization, is the most common cause of QT prolongation by non-cardiac drugs (Brown and Rampe, Pharmaceutical News 2000, 7, 15-20; Weirich and Antoni, Basic Res. Cardiol. 1998, 93 Suppl 1, 125-132; Yap and Camm, Clin. Exp. Allergy 1999, 29 Suppl 3, 174-181). The cardiac potassium channel, hERG, is responsible for a rapid delayed rectifier current (I) in human ventricles (Curran et al., Cell 1995, 80, 795-803; Sanguinetta et al., Cell 1995, 81, 299-307). Drugs that inhibit hERG have the potential to prolong the cardiac action potential and the QT interval, and possibly cause torsade de pointes.

For in vitro testing, the functional hERG assay using conventional patch clamp electrophysiology is considered the gold standard for assessment of drug interactions with the hERG potassium channel (Yao et al., Br. J. Pharmacol. 2008, 154, 1446-1456). In this assay, hERG channels are expressed in a human embryonic kidney (HEK293) cell line that lacks endogenous $I_{Kr}$.

The data is usually classified into the following bands:
hERG inhibition>20% at a concentration:
1 µM or less, high risk,
1-10 µM, medium risk,
10-100 µM, low risk,
Above 100 µM, no risk.

Objective

The objective of this study was to examine the in vitro effects of test articles on the hERG (human ether-à-go-go-related gene) potassium channel current (a surrogate for $I_{Kr}$, the rapidly activating delayed rectifier cardiac potassium current).

Test and Control Articles
Formulations

All chemicals used in solution preparation were purchased from Sigma-Aldrich (St. Louis, Mo.) unless otherwise noted and were of ACS reagent grade purity or higher. Stock solutions of the test article and the positive control were prepared in dimethyl sulfoxide (DMSO) and stored frozen. Test article and positive control concentrations were prepared fresh daily by diluting stock solutions into a HEPES-buffered physiological saline (HB-PS) solution (composition in mM): NaCl, 137; KCl, 4.0; $CaCl_2$, 1.8; $MgCl_2$, 1; HEPES, 10; Glucose, 10; pH adjusted to 7.4 with NaOH (prepared weekly and refrigerated until use). Since previous results have shown that ≤0.3% DMSO does not affect channel current, all test and control solutions contained 0.3% DMSO.

Positive Control Article

Stock solutions of the positive control article were prepared in batches, aliquoted for individual use, stored frozen and used within one month.
Name: Cisapride
Source: Tocris
Molecular Weight (g/mol) 484.0
Storage Conditions (bulk): Room temperature desiccated, protected from light
Rationale for Selection: Previous results have shown that 90 nM cisapride inhibits hERG potassium current by approximately 80%.

Test Article and Positive Control Carrier
Name: Dimethylsulfoxide (DMSO)
Source: Sigma-Aldrich
Molecular Weight (g/mol): 78.13
Storage Conditions: Room temperature
Rationale for Selection: Previous results have shown that 0.3% DMSO does not affect hERG potassium current.

Vehicle Control
Name: HB-PS+0.3% DMSO
Source: ChanTest Corporation
Storage Conditions Refrigerated
Rationale for Selection: HB-PS provides appropriate ionic composition for in vitro hERG potassium current recording Test System
Cells were maintained in tissue culture incubators per ChanTest SOP. Stocks were maintained in cryogenic storage. Cells used for electrophysiology were plated in plastic culture dishes.
HEK/hERG
Organism: *Homo sapiens*
Designation: 293
Tissue: Kidney; Transformed with adenovirus 5 DNA; Transfected with human-ether-a-go-go cDNA
Morphology: Epithelial
Age Stage Embryo
Source Strain: ATCC, Manassas, Va.
Source Substrain ChanTest Corporation, Cleveland, Ohio Cell Culture Procedures
HEK293 cells were stably transfected with hERG cDNA. Stable transfectants were selected by coexpression with the G418-resistance gene incorporated into the expression plasmid. Selection pressure was maintained by including G418 in the culture medium. Cells were cultured in Dulbecco's Modified Eagle Medium/Nutrient Mixture F-12 (D-MEM/F-12) supplemented with 10% fetal bovine serum, 100 U/mL penicillin G sodium, 100 µg/mL streptomycin sulfate and 500 µg/mL G418.

Test Method
Treatment Groups
All experiments were performed at room temperature. Each cell acted as its own control.
Concentration-Response Test Group
Experiments were performed as outlined in the section entitled Experimental Procedures. Concentrations were selected to evaluate the concentration-response relationship of each test article based on the initial results or the solubility limits in vehicle. Each concentration was tested in at least three cells (n≥3).
Positive Control Group
The positive control, 90 nM cisapride, was applied to two cells (n=2).
Electrophysiology
Cells were transferred to the recording chamber and superfused with vehicle control solution. Micropipette solution for whole cell patch clamp recordings was composed of (mM): potassium aspartate, 130; $MgCl_2$, 5; EGTA, 5; ATP, 4; HEPES, 10; pH adjusted to 7.2 with KOH. Pipette solution was prepared in batches, aliquoted, stored frozen, and a fresh aliquot was thawed each day. Patch pipettes were made from glass capillary tubing using a P-97 micropipette puller (Sutter Instruments, Novato, Calif.). A commercial patch clamp amplifier was used for whole cell recordings. Before digitization, current records were low-pass filtered at one-fifth of the sampling frequency.

Experimental Procedures

Onset and steady state inhibition of hERG current was measured using a pulse pattern with fixed amplitudes (conditioning prepulse: +20 mV for 2 s; test pulse: −50 mV for 2 s) repeated at 10 s intervals, from a holding potential of −80 mV. Peak tail current was measured during the 2 s step to −50 mV.

Each test article at 10 µM was applied to at least 3 cells (n≥3). Based on these results and solubility limits, additional nominal concentrations were selected to evaluate each concentration-response relationship.

One or more test article concentrations were applied sequentially (without washout between test substance concentrations) in ascending order, to each cell (n≥3). A steady state was maintained for at least 30 s before applying test article or positive control. Peak current was measured until a new steady state was achieved.

Data Analysis
Data acquisition and analyses were performed using the suite of pCLAMP (version 8.2) programs (MDS-AT, Sunnyvale, Calif.) and were reviewed by the Study Director.

Steady state was defined by the limiting constant rate of change with time (linear time dependence). The steady state before and after test article application was used to calculate the percentage of current inhibited at each concentration. Concentration-response data for Example 1 and 4-(tert-butyl)-2-(tert-butylaminomethyl)-6-(4-chlorophenyl)phenol, WR-194,965, were fit to an equation of the form:

$$\% \text{ Inhibition} = \{1 - 1/[1 + ([\text{Test}]/IC_{50})^N]\} * 100$$

Where [Test] was the test article concentration, $IC_{50}$ was the test article concentration at half-maximal inhibition, N was the Hill coefficient and % Inhibition was the percentage of current inhibited at each test article concentration. Nonlinear least squares fits were solved with the Solver add-in for Excel 2003 (Microsoft, WA) and the $IC_{50}$ was calculated.

Results

Table 3

Descriptive Statistics of Inhibition of hERG Current by 4-(tert-butyl)-2-((tert-butylamino)methyl)-6-(6-(trifluoromethyl)pyridin-3-yl)phenol hydrochloride, Example 1

Mean percentage of current inhibited at each concentration of Example 1 (Mean), standard deviation (SD), standard error of the mean (SEM), and number of cells (N).

| Concentration (µM) | Mean | SD | SEM | N |
|---|---|---|---|---|
| 3 | 18.4% | 0.2% | 0.1% | 3 |
| 10 | 48.5% | 4.5% | 2.6% | 3 |
| 30 | 84.0% | 2.8% | 1.6% | 3 |
| 100 | 98.2% | 0.4% | 0.2% | 3 |

The IC$_{50}$ for the inhibitory effect of Example 1 on hERG potassium current was determined to be 9.8 μM with a Hill coefficient of 1.4.

Table 4

Descriptive Statistics of Inhibition of hERG Current by 4-(tert-butyl)-2-((tert-butylamino)methyl)-6-(2-(trifluoromethyl)pyrimidin-5-yl)phenol hydrochloride, Example 33

Mean percentage of current inhibited at each concentration of Example 33 (Mean), standard deviation (SD), standard error of the mean (SEM), and number of cells (N).

| Concentration (μM) | Mean | SD | SEM | N |
|---|---|---|---|---|
| 3 | 4.1% | 0.2% | 0.1% | 3 |
| 10 | 12.9% | 3.0% | 1.5% | 4 |
| 30 | 24.3% | 0.5% | 0.3% | 3 |

The IC$_{50}$ for the inhibitory effect of Example 33 on hERG potassium current could not be determined but was estimated to be greater than 10 μM as 30 μM was not in solution. The mean reduction of amplitude of the outward tail currents was 12.9% (N=4) at 10 μM.

Table 5

Descriptive Statistics of Inhibition of hERG Current by 4-(tert-butyl)-2-((tert-butylamino)methyl)-6-(5-fluoro-6-(trifluoromethyl)pyridin-3-yl)phenol hydrochloride, Example 34

Mean percentage of current inhibited at each concentration of Example 34 (Mean), standard deviation (SD), standard error of the mean (SEM), and number of cells (N).

| Concentration (μM) | Mean | SD | SEM | N |
|---|---|---|---|---|
| 1 | 2.6% | 1.0% | 0.6% | 3 |
| 3 | 11.3% | 2.4% | 1.4% | 3 |
| 10 | 15.9% | 3.1% | 1.6% | 4 |

The IC$_{50}$ for the inhibitory effect of Example 34 on hERG potassium current could not be determined but was estimated to be greater than 10 μM as 30 μM was not in solution. The mean reduction of amplitude of the outward tail currents was 15.9% (N=4) at 10 μM.

Table 6

Descriptive Statistics of Inhibition of hERG Current by 4-(tert-butyl)-2-(tert-butylaminomethyl)-6-(4-chlorophenyl)phenol, WR-194,965

Mean percentage of current inhibited at each concentration of 4-(tert-butyl)-2-(tert-butylaminomethyl)-6-(4-chlorophenyl)phenol, WR-194,965, (Mean) standard deviation (SD), standard error of the mean (SEM), and number of cells (N).

| Concentration (μM) | Mean | SD | SEM | N |
|---|---|---|---|---|
| 0.3 | 12.8% | 4.7% | 2.4% | 4 |
| 1 | 47.5% | 3.4% | 1.7% | 4 |
| 3 | 80.3% | 4.0% | 2.0% | 4 |
| 10 | 97.2% | 1.6% | 0.9% | 3 |

The IC$_{50}$ for the inhibitory effect of 4-(tert-butyl)-2-(tert-butylaminomethyl)-6-(4-chlorophenyl)phenol, WR-194,965, on hERG potassium current was determined to be 1.1 μM with a Hill coefficient of 1.4.

As shown, the compounds of the present invention possess potent antimalarial activity and greatly reduced toxicity when administered to mammalian subjects.

It is to be understood that while the invention has been described in conjunction with the preferred specific embodiments thereof, that the foregoing description and the examples that follow are intended to illustrate and not limit the scope of the invention. It will be understood by those skilled in the art that various changes may be made and equivalents may be substituted without departing from the scope of the invention, and further that other aspects, advantages and modifications will be apparent to those skilled in the art to which the invention pertains. In addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

The disclosures of each patent, patent application, and publication cited or described in this document are hereby incorporated herein by reference, each in its entirety, for all purposes.

What is claimed:

1. A compound of Formula I:

wherein:
$R^1$ is heteroaryl attached through a carbon atom of the heteroaryl ring, optionally substituted with 1, 2, or 3 $R^5$;
A, B and D are independently are CH or $CR^2$, provided that at least one of A, B, or D is $CR^2$;
each $R^2$ is independently $C_{1-10}$ alkyl, $C_{1-10}$ haloalkyl, halo, cyano, $C_{3-10}$ cycloalkyl, —$SO_2C_{1-6}$ alkyl, $C_{6-10}$ aryl optionally substituted with 1, 2, or 3 $R^5$, or heteroaryl attached through a carbon atom of the heteroaryl ring optionally substituted with 1, 2, or 3 $R^5$;
$R^3$ and $R^{3a}$ are independently hydrogen or $C_{1-10}$ alkyl;
$R^4$ and $R^{4a}$ independently are hydrogen, $C_{1-10}$ alkyl, $C_{1-10}$ haloalkyl, $C_{3-10}$ cycloalkyl, $C_{1-10}$alk$C_{3-10}$cycloalkyl, or $C_{1-10}$alkNR$^7$R$^{7a}$, wherein $R^7$ and $R^{7a}$ are independently H or $C_{1-10}$alkyl, or
$R^4$ and $R^{4a}$ together with the nitrogen through which they are attached, form a heterocyclic ring of 4 to 7 ring atoms, where one carbon ring atom may be optionally replaced with NR⁶ or O, and where any carbon ring atom may be optionally substituted with $C_{1-6}$ alkyl or $C_{1-6}$ alkoxy;

each $R^5$ is independently halo, cyano, hydroxy, $C_{1-10}$ alkyl, $C_{1-10}$ haloalkyl, $C_{1-10}$ alkoxy, $C_{1-10}$ haloalkoxy, $C_{3-10}$ cycloalky, $C_{3-10}$ cycloalkoxy, amino, $C_{1-10}$ alkylamino, $C_{1-10}$ dialkylamino, $C_{3-10}$ cycloalkyamino, pyrrolidinyl, $C_{1-10}$ alkylsulfonyl, sulfamoyl, $C_{1-10}$ alkylsulfamoyl or $C_{1-10}$ dialkylsulfamoyl; and $R^6$ is $C_{1-10}$ alkyl or acetyl;

or a pharmaceutically acceptable salt, enantiomer, or diastereoisomer thereof.

2. The compound according to claim 1 wherein A and D are CH, and B is $CR^2$.

3. The compound according to claim 1 wherein $R^3$ and $R^{3a}$ are H.

4. The compound according to claim 1 wherein $R^4$ is tert-butyl and $R^{4a}$ is H.

5. The compound according to claim 1 wherein:
$R^2$ is tert-butyl, $C_{6-10}$ aryl optionally substituted with 1, 2, or 3 $R^5$, or heteroaryl attached through a carbon atom of the heteroaryl ring optionally substituted with 1, 2, or 3 groups of $R^5$.

6. The compound according to claim 1 wherein $R^2$ is tert-butyl.

7. The compound according to claim 1 wherein $R^1$ is pyridyl, pyrimidinyl, pyrazinyl, or thienyl attached through a carbon atom of the heteroaryl ring, optionally substituted with 1, 2, or 3 $R^5$.

8. The compound according to claim 1 wherein $R^1$ is thiophenyl, quinolinyl, isoquinolinyl, benzofuranyl, benzothiophenyl, or pyrazolyl each optionally substituted with 1, 2, or 3 $R^5$.

9. The compound according to claim 1 wherein:
A and D are CH, and B is $CR^2$;
$R^3$ and $R^{3a}$ are H;
$R^4$ is tert-butyl and $R^{4a}$ is H;
$R^2$ is tert-butyl, $C_{6-10}$ aryl optionally substituted with 1, 2, or 3 groups of $R^5$, or heteroaryl attached through a carbon atom of the heteroaryl ring optionally substituted with 1, 2, or 3 $R^5$,
$R^1$ is pyridyl, pyrimidinyl, pyrazinyl, or thienyl, attached through a carbon atom of the heteroaryl ring, optionally substituted with 1, 2, or 3 $R^5$.

10. The compound according to claim 1 wherein:
A and D are CH, and B is $CR^2$;
$R^3$ and $R^{3a}$ are H;
$R^4$ is tert-butyl and $R^{4a}$ is H;
$R^2$ is tert-butyl;
$R^1$ is pyridyl, pyrimidinyl, pyrazinyl, or thienyl attached through a carbon atom of the heteroaryl ring optionally substituted with 1, 2, or 3 $R^5$.

11. The compound according to claim 1 that is:

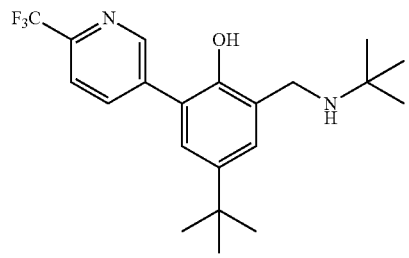 [SMILES: CC(C)(C)NCc1cc(C(C)(C)C)cc(-c2ccc(C(F)(F)F)nc2)c1O]

4-(tert-butyl)-2-((tert-butylamino)methyl)-6-(6-(trifluoromethyl)pyridin-3-yl)phenol;

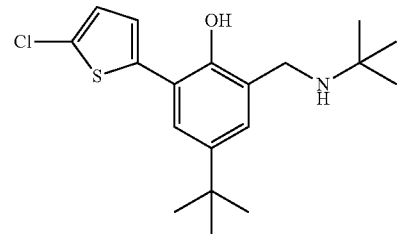 [SMILES: CC(C)(C)NCc1cc(C(C)(C)C)cc(-c2ccc(Cl)s2)c1O]

4-(tert-butyl)-2-((tert-butylamino)methyl)-6-(5-chlorothiophen-2-yl)phenol;

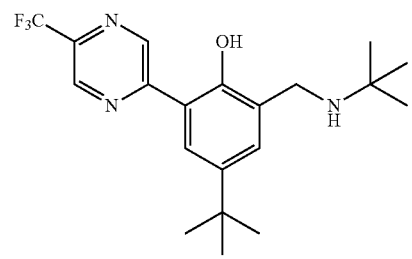 [SMILES: CC(C)(C)NCc1cc(C(C)(C)C)cc(-c2cnc(C(F)(F)F)cn2)c1O]

4-(tert-butyl)-2-((tert-butylamino)methyl)-6-(5-(trifluoromethyl)pyrazin-2-yl)phenol;

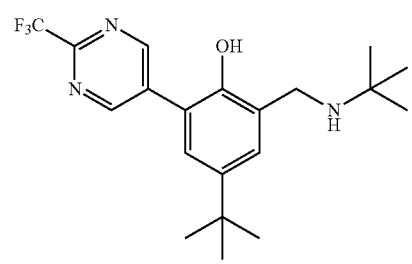 [SMILES: CC(C)(C)NCc1cc(C(C)(C)C)cc(-c2cnc(C(F)(F)F)nc2)c1O]

4-(tert-butyl)-2-((tert-butylamino)methyl)-6-(2-(trifluoromethyl)pyrimidin-5-yl)phenol;

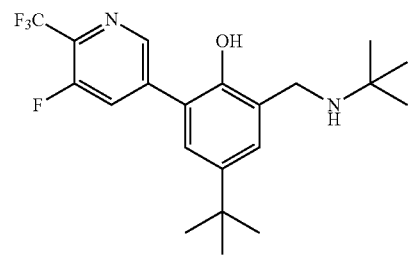 [SMILES: CC(C)(C)NCc1cc(C(C)(C)C)cc(-c2cnc(C(F)(F)F)c(F)c2)c1O]

4-(tert-butyl)-2-((tert-butylamino)methyl)-6-(5-fluoro-6-(trifluoromethyl)pyridin-3-yl)phenol;

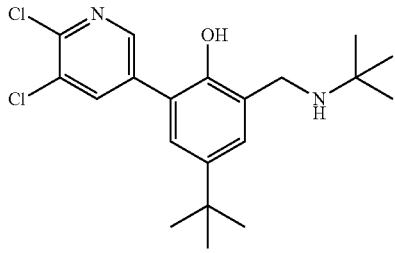 [SMILES: CC(C)(C)NCc1cc(C(C)(C)C)cc(-c2cnc(Cl)c(Cl)c2)c1O]

4-(tert-butyl)-2-((tert-butylamino)methyl)-6-(5,6-dichloropyridin-3-yl)phenol; or

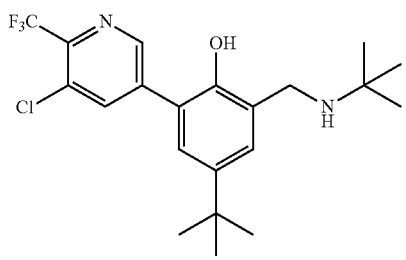 [SMILES: CC(C)(C)NCc1cc(C(C)(C)C)cc(-c2cnc(C(F)(F)F)c(Cl)c2)c1O]

4-(tert-butyl)-2-((tert-butylamino)methyl)-6-(5-chloro-6-(trifluoromethyl)pyridin-3-yl)phenol;

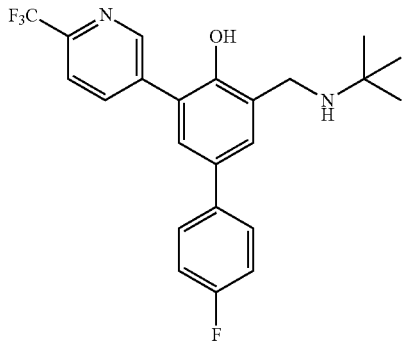 [SMILES: CC(C)(C)NCc1cc(-c2ccc(F)cc2)cc(-c2ccc(C(F)(F)F)nc2)c1O]

3-((tert-butylamino)methyl)-4'-fluoro-5-(6-(trifluoromethyl)pyridin-3-yl)-[1,1'-biphenyl]-4-ol; or

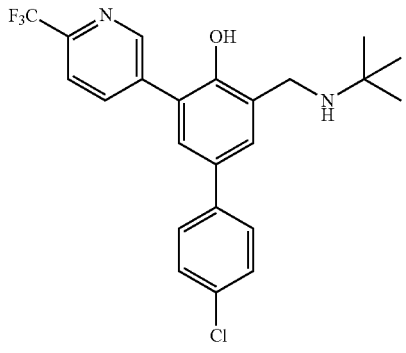 [SMILES: CC(C)(C)NCc1cc(-c2ccc(Cl)cc2)cc(-c2ccc(C(F)(F)F)nc2)c1O]

3-((tert-Butylamino)methyl)-4'-chloro-5-(6-(trifluoromethyl)pyridin-3-yl)-[1,1'-biphenyl]-4-ol;
or a pharmaceutically acceptable salt thereof.

12. The compound according to claim 1 that is a compound of formula IA:

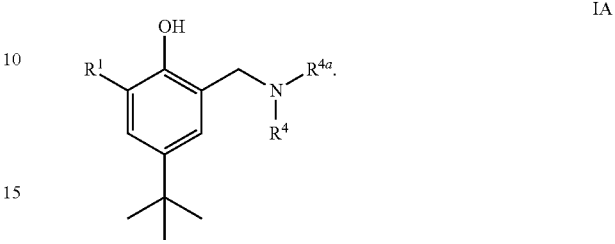

IA

13. The compound according to claim 12, wherein $R^1$ is pyridyl, thiophenyl, quinolinyl, isoquinolinyl, benzofuranyl, benzothiophenyl, pyrazolyl, pyrazinyl, or pyrimidinyl, each optionally substituted with 1, 2, or 3 $R^5$.

14. The compound according to claim 12, wherein $R^1$ is thiophenyl, benzofuranyl, benzothiophenyl, pyrazolyl, pyrazinyl, or pyrimidinyl, each optionally substituted with 1, 2, or 3 $R^5$.

15. The compound according to claim 12, wherein $R^4$ and $R^{4a}$ are independently hydrogen or $C_{1-6}$ alkyl.

16. The compound according to claim 12, wherein $R^4$ and $R^{4a}$ together with the nitrogen through which they are attached, form a heterocyclic ring of 4 to 7 ring atoms.

17. The compound according to claim 12, wherein the compound of formula IA is:

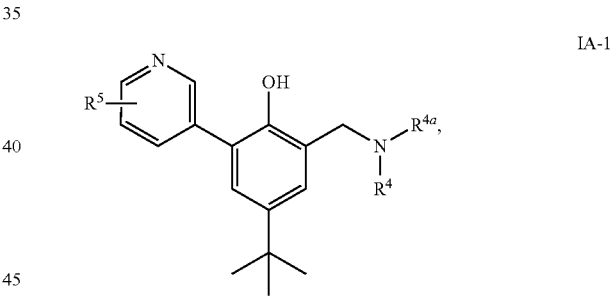

IA-1

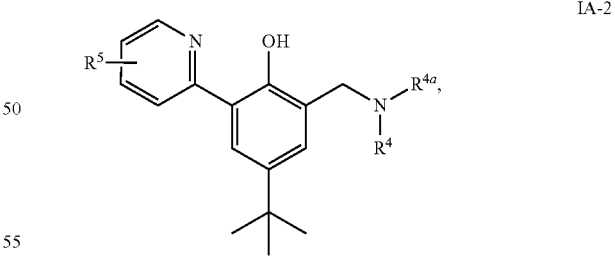

IA-2

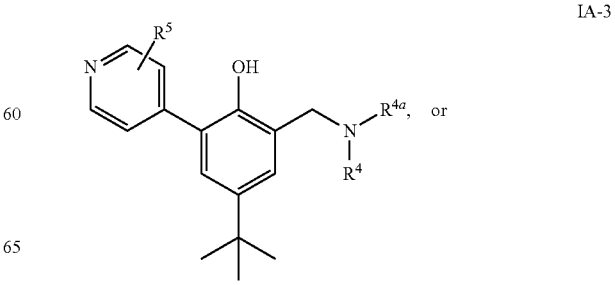

IA-3

-continued

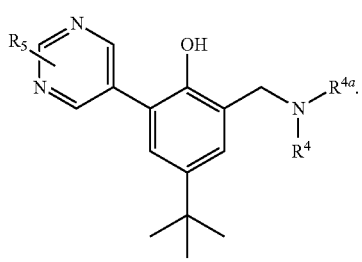

18. The compound according to claim 12, wherein the compound of formula IA is:

IA-4

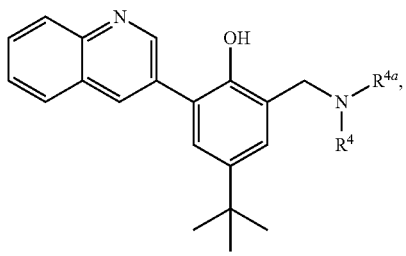

IA-5

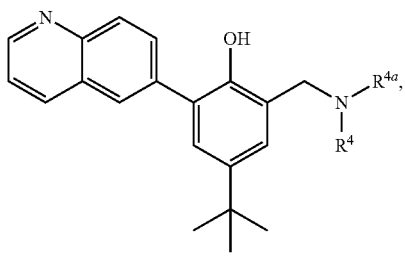

IA-6

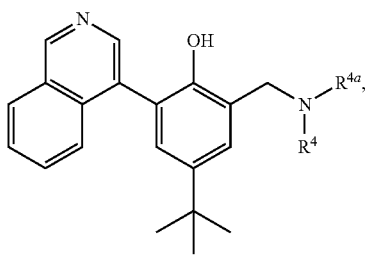

-continued

IA-7

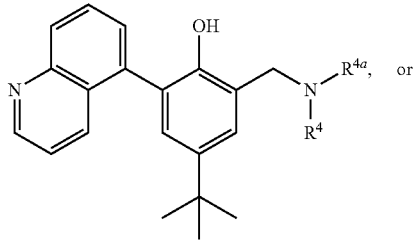

IA-8

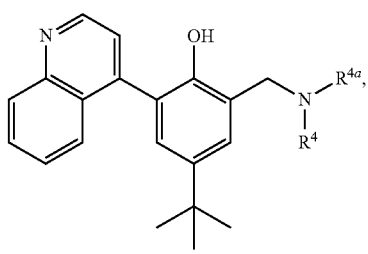

wherein each quinolinyl or isoquinolinyl of IA-4, IA-5, IA-6, IA-7, or IA-8 is optionally substituted with 1, 2, or 3 $R^5$.

19. The compound according to claim 12, wherein each $R^5$ is independently —$CF_3$, F,

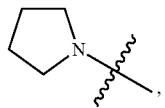 [SMILES: *N1CCCC1]

Cl, Br, —$NH_2$, —$OC_{1-6}$alkyl, —CN, —$N(CH_3)_2$, $C_{1-10}$alkyl, $C_{1-10}$alkylsulfonyl, or —$C_{3-6}$cycloalkyl.

20. A pharmaceutical composition comprising a compound according to claim 1 and a pharmaceutically acceptable carrier or diluent.

21. A method for treating malaria in a patient comprising administering to the patient a compound according to claim 1.

22. The method according to claim 21 wherein the compound of Formula I is co-administered with at least one agent that is Amodiaquine, Arteether, Arteflene, Artemether, Artemisinin, Artesunate, Atovaquone, Chloroquine, Clindamycin, Dihydroartemisinin, Doxycycline, Halofantrine, Lumefantrine, Mefloquine, Pamaquine, Piperaquine, Primaquine, Proguanil, Pyrimethamine, Pyronaridine, Quinine, Tafenoquin, or a combination thereof.

\* \* \* \* \*